US007320785B2

(12) United States Patent
Greengard et al.

(10) Patent No.: US 7,320,785 B2
(45) Date of Patent: Jan. 22, 2008

(54) COMPOSITIONS AND METHODS FOR MODULATION OF DARPP-32 PHOSPHORYLATION

(75) Inventors: Paul Greengard, New York, NY (US); Per Svenningsson, New York, NY (US); Sergey V. Rakhilin, Yorktown, NY (US); Natalia Starkova, New York, NY (US)

(73) Assignee: The Rockefeller University, New York, NY (US)

( * ) Notice: Subject to any disclaimer, the term of this patent is extended or adjusted under 35 U.S.C. 154(b) by 546 days.

(21) Appl. No.: 10/218,137

(22) Filed: Aug. 12, 2002

(65) Prior Publication Data

US 2003/0171255 A1  Sep. 11, 2003

Related U.S. Application Data

(60) Provisional application No. 60/311,641, filed on Aug. 10, 2001.

(51) Int. Cl.
*A61K 49/00* (2006.01)
*G01N 33/53* (2006.01)
*G01N 33/567* (2006.01)

(52) U.S. Cl. .................. 424/9.2; 424/9.1; 435/7.2; 435/7.21

(58) Field of Classification Search ............... 435/7.2, 435/4, 7.21; 424/9.2, 9.1
See application file for complete search history.

(56) References Cited

U.S. PATENT DOCUMENTS

| | | | |
|---|---|---|---|
| 5,902,815 | A | 5/1999 | Olney et al. |
| 6,166,008 | A | 12/2000 | Johnson et al. |
| 6,410,556 | B1 | 6/2002 | Andersen et al. |
| 2002/0042357 | A1 | 4/2002 | Hanson et al. |
| 2002/0103185 | A1 | 8/2002 | Sanner et al. |

FOREIGN PATENT DOCUMENTS

WO    PCT/US02/25455    12/2002

OTHER PUBLICATIONS

Desdouits et al. (Feb. 1998). Dephosphorylation of SER-137 in DARPP-32 by protein phosphatases 2A and 2C: different roles in vitro and in striatonigral neurons. Biochemical Journal, 330, 211-216.*
Weintraub et al (2005). MOvement disorders. 20, 1161-1169.*
Perilstein et al. (1991). J. Clin Psych. 52, 169-170. Abstract only.*
Zajecka et al (1991). J. Clin. Psych. 52, 66-68.Abstract only.*
Kafka (1991). Br. J.Psychiatry. 158, 844-847.Abstract only.*
Lorifice (1991). J. Clin. Psych. 52, 41 (abstract only).*
Bianchi (1990). Am. J. Psych. (abstract only).*
Ferguson et al. (1999). Int. J. Eating Disord. 25, 11-17.*
Gigli et al (1994). Seizure. 3, 221-224. (abstract only).*
Grabowski et al (1995) J. Clin Psychopharm. 15, 163-164. (abstract only).*
Mei lai et al (2005). Microbiology. 151, 1159-1167.*
Barnes et al., "A Review of Central 5-HT Receptors and Their Function," (1999), Neuropharmacology, 38:1083-1152.
Barria et al., "Regulatory Phosphorylation of AMPA-Type Glutamate Receptors by CaM-KII During Long-Term Potentiation," (1997), Science, 276:2042-2045.
Beasley et al., "Fluoxetine: A Review of Receptor and Functional Effects and Their Clinical Implications," (1992), Psychopharmacology, 107:1-10.
Bibb et al., "Phosphorylation of DARPP-32 By Cdk5 Modulates Dopamine Signaling In Neurons," (1999), Nature 402: 669-671.
Bristow et al., "Evidence For Accelerated Desenstitisation of 5-HT$_{2c}$ Receptors Following Combined Treatment with Fluoxetine and the 5-HT$_{1a}$ Receptor Antagonist, WAY 100,635 In The Rat," (2000), Neuropharmacology, 39:1222-1236.
Desdouits et al., "Dephosphorylation of Ser-137 in DARPP-32 By Protein Phosphatases 2A and 2C: Different roles *in vitro* and in Striatonigral Neurons," (1998), J. Biochem, 330:211-216.
Desdouits et al., "Dopamine- and cAMP-Regulated Phosphoprotein DARPP-32: Phosphorylation of Ser-137 By Casein Kinase I Inhibits Dephosphorylation of Thr-34 By Calcineurin," (1995), PNAS, 92:2682-2685.
Desdouits et al., "Phosphorylation of DARPP-32, a Dopamine- and cAMP-regulated Phosphoprotein, by Casein Kinase I *in Vitro*, and *in Vivo*," (1995), The Journal of Biological Chemistry, 270:8772-8778.
Duman et al., "A Molecular and Cellular Theory of Depression," (1997), Arch Gen Psychiatry, 54:597-606.
Fienberg et al., "DARPP-32: Regulator of the Efficacy of Dopaminergic Neurotransmission," (1998), Science, 281:838-842.
Fleischhacker et al., "A Multicenter Double-Blind Study of Three Different Doses of the New cAMP-Phosphodiesterase Inhibitor Rolipram In Patients With Major Depressive Disorder," (1992), Neuropsychobiology, 26:59-64.

(Continued)

*Primary Examiner*—David Romeo
*Assistant Examiner*—Steven Standley
(74) *Attorney, Agent, or Firm*—Hoxie & Associates LLC

(57) ABSTRACT

The present invention provides methods and compositions for modulating the phosphorylation of DARPP-32 in a serotonergic receptor intracellular signaling pathway. The invention provides methods and compositions for modulating the activities of DARPP-32, casein kinase 1 (CK1), cyclin-dependent kinase 5 (Cdk5), AMPA receptors, protein phosphatase-1 (PP-1), protein phosphatase 2C (PP2C), protein phosphatase 2B (PP2B) and/or protein phosphatase 2A (PP2A) in cells or tissues. The invention provides methods of treating serotonergic intracellular signaling pathway disorders, e.g., depression. The invention provides methods of treating dopamine-related disorders. The invention provides methods of identifying agents that modulate the activities of serotonergic receptor intracellular signaling molecules, DARPP-32, casein kinase 1, cyclin-dependent kinase 5, AMPA receptors, protein phosphatase-1, protein phosphatase 2C, protein phosphatase 2B and/or protein phosphatase 2A, for use in such treatments. The invention also provides methods of modulating phosphorylation-dependent activation of AMPA receptors for use in such treatments.

4 Claims, 20 Drawing Sheets

OTHER PUBLICATIONS

Figure 1:
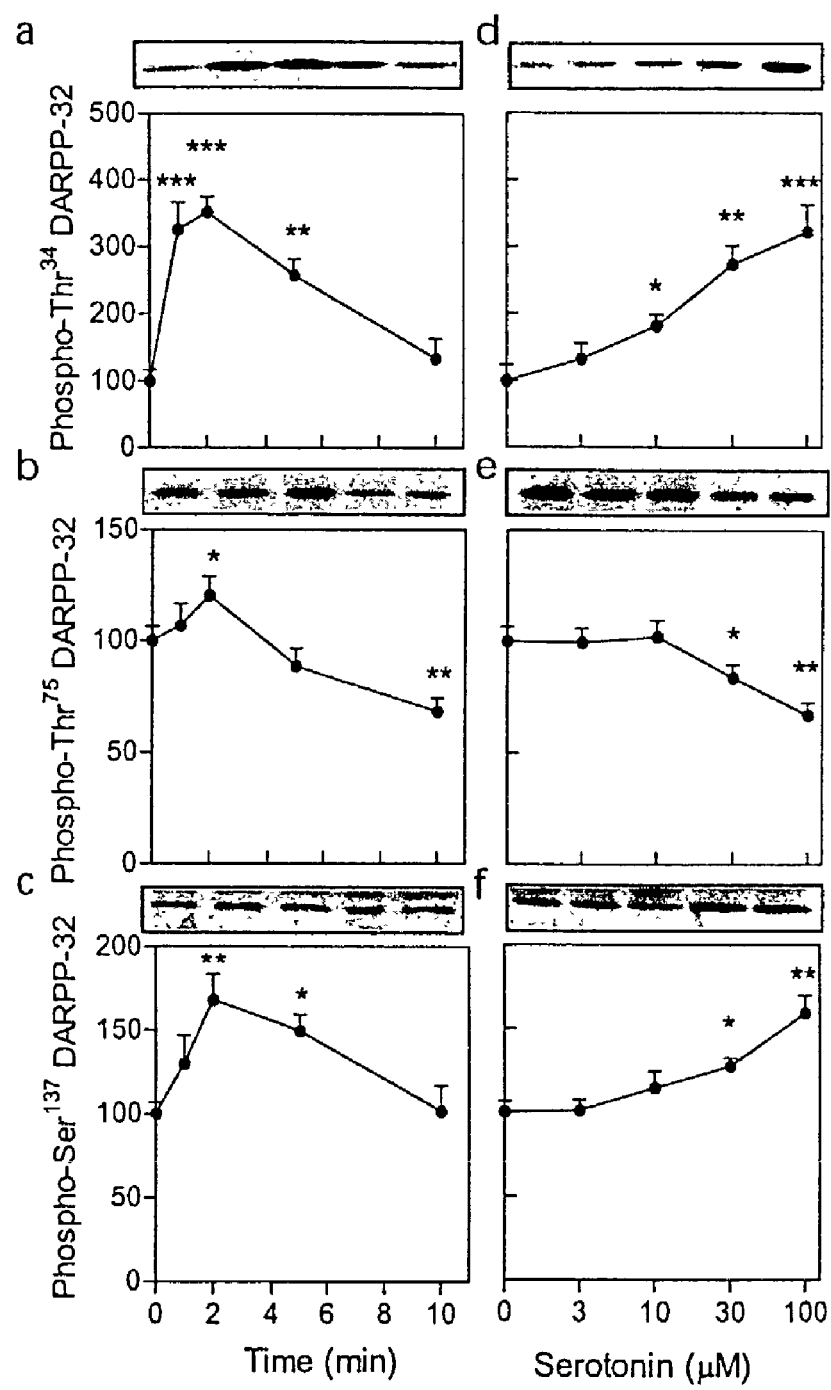

Fukunaga et al., "Dephosphorylation of Autophosphorylated $Ca^{2+}$/Calmodulin-Dependent Protein Kinase II by Protein Phosphatase," (1993), The Journal of Biological Chemistry, 268:133-137.

Greengard et al., "Beyond the Dopamine Receptor: The DARPP-32/Protein Phosphatase-1 Cascade," (1999), Nature, 23:435-447.

Greengard et al., "Enhancement of the Glutamate Response by cAMP-Dependent Protein Kinase in Hippocampal Neurons," (1991), Science, 253:1135-1138.

Greengard et al., "The Neurobiology of Slow Synaptic Transmission," (2001), Science, 294:1024-1030.

Gross et al., "Casein Kinase I: Spatial Organization and Positioning of a Multifunctional Protein Kinase Family," (1998), Cell Signal, 10:699-711.

Guitart et al., "Chronic Administration of Lithium or Other Antidepressants Increases Levels of DARPP-32 in Rat Frontal Cortex," (1992), Journal of Neurochemistry, 59:1164-1167.

Hanada et al., "Regulation of the TAKI Signaling Pathway by Protein Phosphatase 2C," (2001), The Journal of Biological Chemistry, 276:5753-5759.

Hemmings et al., "DARPP-32 A Dopamine- and Adenosine 3':5'-Monophospate-Regulated Phosphoprotein:Regional, Tissue, and Phylogenetic Distribution," (1986), The Journal of Neuroscience, 6:1469-1481.

Hemmings, et al., "DARPP-32, A Dopamine-Regulated Neuronal Phosphoprotein, Is A Potent Inhibitor Of Protein Phosphatase-1," (1998), Nature, 310:503-508.

Hishiya et al., "Protein Phosphatase 2C Inactivates F-Actin Binding of Human Platelet Meosin," (1999), The Journal of Biological Chemistry, 274:26705-26712.

Horowski et al., "Clinical Effects of the Neurotropic Selective cAMP Phosphodiestersase Inhibitor Rolipram In Depressed Patients: Global Evaluation of the Preliminary Reports," (1985), current Therapeutic Research, 38:23-29.

Ivkovic et al., "Brain-Derived Neurotrophic Factor Regulates Maturation of the DARPP-32 Phenotype In Striatal Medium Spiny Neurons: Studies IN VIVO and IN VITRO," (1997), Neuroscience, 79:509-516.

Kusakawa et al., "Calpain-Dependent Proteolytic Cleavage of the p35 Cyclin Dependent Kinase 5 Activator to p25," (2000), The Journal of Biological Chemistry 275:17166-17172.

Lee et al., "Neurotoxicity Induces Cleavage of p35 to p25 By Calpin," (2000), Nature, 405:360-364.

Li et al., "Antidepressant-Like Actions of an AMPA Receptor Potentiator (LY392098)," (2001) Neuropharmacology, 40:1028-1033.

Liu et al., "Regulation Of Cyclin-Dependent Kinase 5 and Casein Kinase 1 By Metabotropic Glutamate Receptors," (2001), PNAS, 98:11062-11068.

Manji et al., "The Cellular Neurobiology of Depression," (2001), Nature Medicine, 7:541-547.

Marley et al., "The Cloning Expression And Tissue Distribution of Human PP2cβ," (1998), FEBS Letters, 431:121-124.

Moine et al., "D1 and D2 Dopamine Receptor Gene Expression in the Rat Striatum: Sensitive cRNA Probes Demonstrate Prominent Segregation of D1 and D2 mRNA's in District Neuronal Populations of the Dorsal and Ventral Striatum," (1995), The Journal of Comparative Neurology, 355:418-426.

Murphy et al., "Brain Serotonin Neurotransmission: An Overview and Update With an Emphasis on Serotonin Subsystem Heterogeneity, Multiple Receptors, Interactions With Other Neurotransmitter Systems, and Consequent Implications For Understanding the Actions of Serotonergic Drugs," (1998), J. Clin. Psychiatry, 59(Suppl 15):4-12.

Nath et al., "Processing of cdk5 Activator p35 To Its Truncated Form (p25) By Calpain In Acutely Injured Neuronal Cells," (2000), Biochemical and Biophysical Research Communications, 274:16-21.

Nishi et al., "Bidirectional Regulation of DARPP-32 Phosphorylation By Dopamine," (1997), The Journal of Neuroscience, 17:8147-8155.

Ouimet et al., "DARPP-32, A Dopamine-And Adenosine 3':5'-Monophosphate-Regualted Phosphoprotein Enriched In Dopamine-innervated Brain Regions," (1984), The Journal of Neuroscience, 4:111-124.

Patrick et al., "Conversion of p35 to p25 Deregulates Cdk5 Activity and Promotes Neurodegeneration," (1999), Nature, 402:615-622.

Popoli et al., "Second Messenger-Regulated Protein Kinase in the Brain: Their Functional Role and the Action of Antidepressant Drugs," (2000), Journal of Neurochemistry, 43:411-422.

Roche et al., "Characterization of Multiple Phosphorylation Sites on the AMPA Recepton FluR1 Subunit," (1996), Neuron, 16:1179-1188.

Siucack et al., "Antidepressant-Like Effect of Brain-Derived Neurotrophic Factor (BDNF)," (1997), Pharmacology Biochemistry and Behavior, 56:131-137.

Skolnick et al., "Current Perspectives On The Development of Non-Biogenic Amine-Based Antidepressants," (2001), Pharmacological Research, 43:411-422.

Snyder et al., "Regulation of phosphorylation of the GluR1 AMPA Receptor in the Neostriatum by Dopamine and Psychostimulants In Vivo," (2000), The Journal of Neuroscience, 20:4480-4488.

Snyder et al., "Phosphorylation of DARPP-32 and Protein Phosphatase Inhibitor-1 In Rat Choroid Plexus: Regulation By Factors Other Than Dopamine," (1992), The Journal of Neuroscience, 12:3071-3083.

Svenningsson et al., "DARPP-32 Mediates Serotonergic Neurotransmission In The Forebrain," (2002), PNAS, 99:3188-3193.

Svenningsson et al., "Involvment of Striatal and Extrastriatal DARPP-32 In Biochemical and Behavioral Effects of Fluoxetine," (2002), PNAS, 99:3182-3187.

Travis et al., "PP2cγ: A Human Protein Phosphatase With A Unique Acidic Domain," (1997), FEBS Letters, 412:415-419.

Walaas et al., "A Dopamine- and Cyclic AMP-Regulated Phosphoprotein Enriched In Dopamine-Innervated Brain Regions," (1983), Nature, 301:69-71.

Yan et al., "Protein Phosphatase I Modulation of Neostriatal AMPA Channels: Regulation By DARPP-32 and Spinophilin," (1999), Nature Neuroscience, 2:13-17.

Svenningsson et al., "Involvement of striatal and extrastriatal DARPP-32 in biochemical and behavioral effects of fluoxetine (Prozac)," (Mar. 5, 2002), Laboratory of Molecular and Cellular Neuroscience, The Rockefeller University, vol. 99 pp. 3142-3187.

Cai et al., Serotonin 5-$HT_{1A}$ Receptors Regulate AMPA Receptor Channels through Inhibiting Ca2+/Calmodulin-dependent Kinase II in Prefrontal Cortical Pyramidal Neurons*, (2002), The Journal of Biological Chemistry, vol. 277, No. 39, pp. 36553-36562.

Bauman et al., "Cocaine and Antidepressant-Sensitive Biogenic Amine Transporters Exist in Regulated Complexes with Protein Phosphatase 2A", (Oct. 15, 2000), The Journal of Neuroscience, pp. 7571-7578.

* cited by examiner

```
alpha     1  ----------------------------------------------------------
beta      1  ----------------------------------------------------------
gamma     1  ----------------------------------------------------------
delta     1  ------------MDLFGDLPEPERAPRPSAGKEAQEGPVLFEDLPPTSSTDSGSGGPLLFDGLPPAGSGNSG
NERPP     1  ------------MLTRVKSAVANFMGGIMAGSSGSEHGGSGCGGSDLPLRFPYGRPEFLGLSQDEVECSA alpha     1  ---------------MGAPLDKPKMERHNAQ---------GQGNG----LRYGLSSMQGWRVEMEDAHTAVIG
beta      1  ---------------MCAPLDEPKTEKHNAH---------GAGNG----LRYGLSSMQGWRVEMEDAHTAVVG
gamma     1  ---------------MGAVDSQPNTVKCSGD---------GVGAPRLPLPYGFSAMQGWRVSMEDAHNCKPE
delta    61  SLATSGSQVVKNEGKGARRKAPEEEKNGGEELVEKKVCKASSVIFGLKGYVAERKGEREEMQDAHVILND
NERPP    59  DSHARPILILKETRRLPWATGYAEVINACKSTHNEDQASCEVLTVKKKVGTIESTPNRNSKRRSSLPNGH
                                                                    △  ** alpha    46  LPNGLE-------TWSFPAVYDGHAGSQVAKYGCEHHLDHIIMNQ----DFK-----------
beta     46  TPHGLE-------DWSFPAVYDGHAGSRVANYCSTHHLEHIITNE----DFR-----------
gamma    49  LDH----------ETAMPSVYDGHGCEEVALICAKYLPDIHKDQK----AKKEGKLQKALGDAFLAIDAKL
delta   131  ETQECNPPSSLITRVSYPAVYDGHGCIRASKFAAQNLHQNLIRKFPKG---------------
NERPP   129  GLQLKENSESREGISCHYNSLFDGHAGSGAAVVRSRLLQRHIIQQLQDIVEILKN--------
                          ** alpha    87  ----------------------------------------------------------
beta     87  ----------------------------------------------------------
gamma   106  TTEEVIKELAQIAGRPTEDEDDKEKVADEDDVDNEEAALLHEEATMTIEELLTRYGQNCQKGPPHTKSGT
delta   179  ----------------------------------------------------------
NERPP   183  ---------------------------------------------------------- alpha    87  -------------GSAG-------APSVEN------------------------
beta     87  -------------AADKSGPALEPSVEN------------------------
gamma   176  GIGEDPEPQGLNGERGPEDPSRETPSQENGPTAKGYTGPSSNSDEGTEAGQIGEPGTATGEAGPSCSSAS
delta   179  -------------DVISVEKT-----------------------------
NERPP   183  -------------SAILPPTCLGEEQESTPAHG---------------RTLTRA alpha    97  --VKNGIRTGFLEIDEHMRVMSEKKHG------------------------
beta    102  --VKTQIRTGFLKIDEYMRNFSDLRNG------------------------
gamma   246  DKLPRVAKSKPFEDSRDESDEVEEEDDSEECSEDRDGYSSEEAENEKDEDDTEEAEEDDDEE---MHVP
delta   187  --VKRCLLDTRKHTDEEFLKQASSQKP------------------------
NERPP   209  ASLRGGVGAPGSPSTPPTRFFTERKIPHECLVIG-----------ALESAFKEMDLQ alpha   122  --------KDRSGSTAVGVLISPQHTYFINCGDSRQLLCRNRK------VHFPTQDHKFSNPLEKERIQN
beta    127  --------MDRSGSTAVGVMISPTHIYFINCGDSRAVLCRNGQ------VCFSTQDHKFCKPMEKERIQN
gamma   313  GMEGKEEPGSDSGTTAVVALIRGKQDIVANAGDSRCVVSEAGK------ALDMSYDHKPSDEYELARIKN
delta   212  --------AWKDQSTATCVLAVDNHILYLANLGDSRAILCRYNEESQKHBAALSLRKELNPTQYEERMRIQK
NERPP   255  IERERSRYNISGGCTALIVVCLLGKLYVANAGDSRAEIIRNGEIIPMSSEFTPETERQRLQYLAFMQPHL alpha   178  AG------------------------------GSVMIQ-RVNGSLAVSRALGDF
beta    183  AG------------------------------GSVMIQ-RVNGSLAVSRALGDY
gamma   377  AG------------------------------CKVTMDGRVNGQLNLSRAFGDH
delta   274  AG------------------------------CNVRDG-RVLGVLEVSRFIGDG
NERPP   325  LGNEFTHLEPPRRVQRKELGKRMLYRDFNMTGWAYKTIEDDDLKFPLIYGEGKKARVMATIGVTRGLGDH alpha   201  DYKCVHGKGQTEQLVSPEPEVHDIERSEEDDQ---GIILACDGIWDVMCNEELCDFVRSRLEVIQDLEKV
beta    206  DYKCVDGKGQTEQLVSPEPEVYEILRAEEDE----GVVLACDGIWDVMSNEELCEFVNSRLEVSPDLENV
gamma   401  FYKRNKNLPLQEQMISALPDIKVLTLT-DDBE---GMVDACDGIWNVMSSQEVVDEIQSKISQRDENGEL
delta   297  QYKRCG-------VTSVPDIRRCQITPNDE----FIDLACDGLFKVFTPEEAVNLILSCLE-------
NERPP   395  DLKVHDSNIYIKPFLSSAPEVRVYDLSKYEHGADDVLILATDGCLWDVLSDEEVAEALTQFLPNCDPDDPH alpha   268  CNEVVDTCLYKGSRDNMSVIDICFPNAPKVSAEDVKKAELDKYPGNRVEEPIKKQGE-GVPDLVEVMRT
beta    272  CNWVVDTCLHRGSRDNMSIVLVCFANAFKVSDEAVKRDLELDKHLESRVEEIMQKSGEEGMFDLAHVMRL
gamma   467  R---------LLSSIVEELLDQCLAPDTSGDGTGCDNMTCIITCFKPRNTVELQPESGKRKLEEVLST
delta   347  ----------DEKIQTREGKPAVDARYEAACKRLANEAVQRGSADNVTLVVV
NERPP   465  R-----------YTLAHQPLVMRARGVIKDEGWRESNDRLDSEDDISVYVEPL alpha   337  LASENIPSLPPGGELASKRNVIEAVYNRLNPYKNDDTDSASTDDMW---
beta    342  USAENIPNLPPGGGLAGKSNVIEAVYSRLNPNKDNGGAGDLEDSLVAL
gamma   526  EGAE---------------------ENGNSDKKK-AKRD-----
delta   389  RIGH----------------------------
NERPP   507  IHGNKES-------------------------
```

FIG. 13A

A.

B.

C.

D.

Figure 17C:
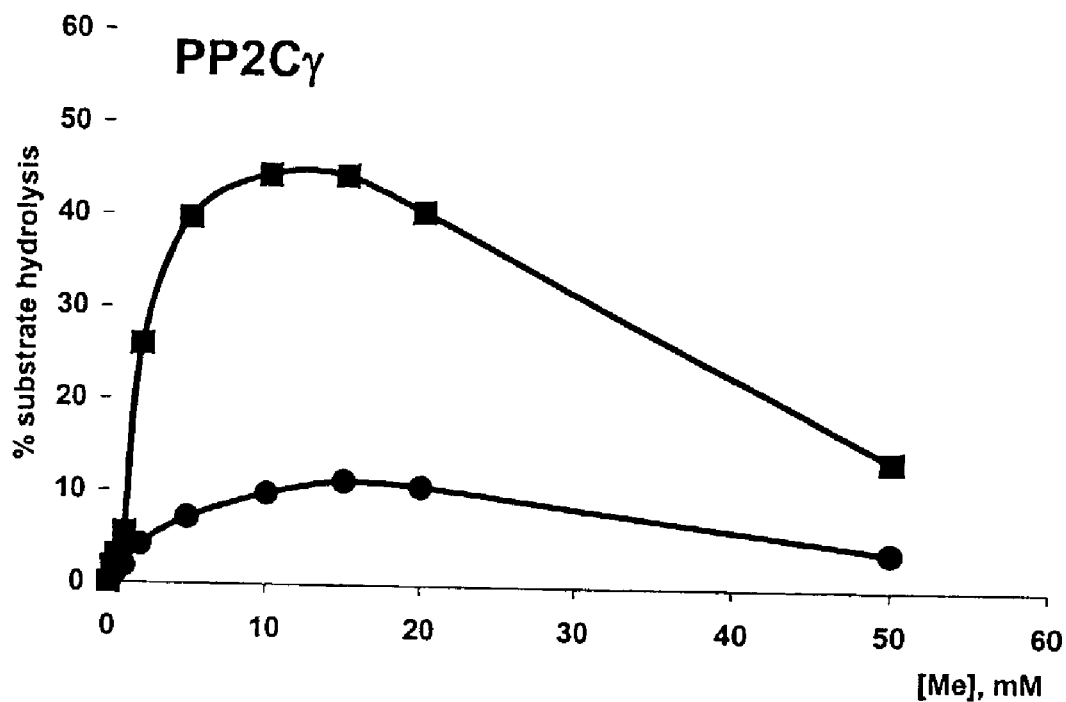

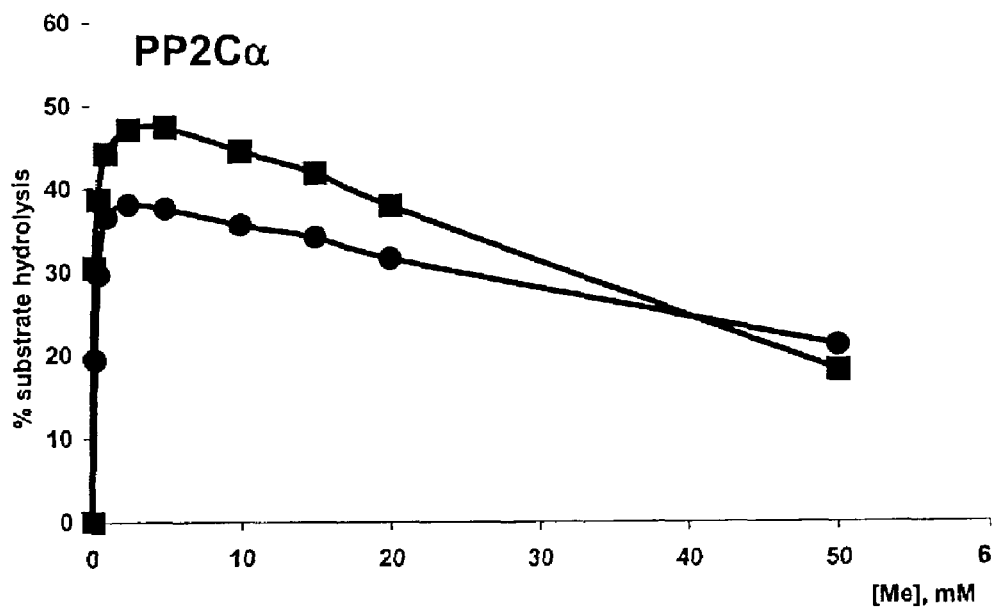
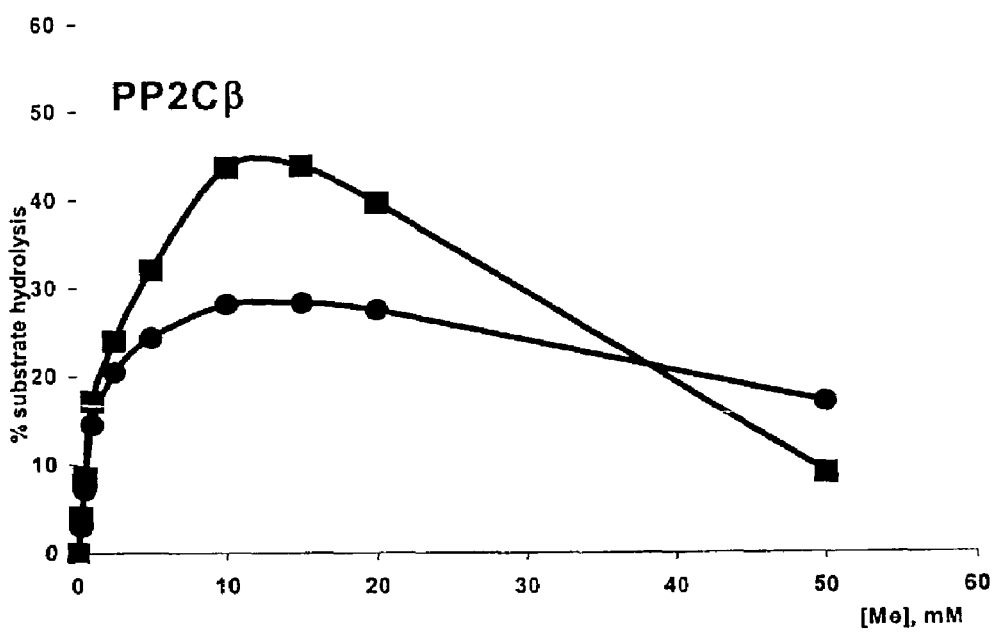
FIGS. 17A-B

C.

COMPOSITIONS AND METHODS FOR MODULATION OF DARPP-32 PHOSPHORYLATION

RELATED APPLICATIONS

This application claims benefit, under 35 U.S.C. § 119(e), of U.S. provisional application No. 60/311,641, filed on Aug. 10, 2001, which is incorporated herein by reference in its entirety.

This invention was made with Government support under grant numbers MH-40899 and DA10044, awarded by the National Institute of Mental Health. The United States Government has certain rights in the invention.

1. TECHNICAL FIELD

The present invention relates to methods and compositions for modulating the phosphorylation of DARPP-32 in a serotonergic receptor intracellular signaling pathway. The present invention relates to methods and compositions for modulating the activities of DARPP-32, casein kinase 1 (CK1), cyclin-dependent kinase 5 (Cdk5), AMPA receptors, protein phosphatase-1 (PP-1), protein phosphatase 2C (PP2C), protein phosphatase 2B (PP2B) and/or protein phosphatase 2A (PP2A) in cells or tissues. The present invention relates to methods of treating serotonergic intracellular signaling pathway disorders, e.g., depression. The present invention also relates to methods of treating dopamine-related disorders. The present invention relates to methods of identifying agents that modulate the activities of serotonergic receptor intracellular signaling molecules, DARPP-32, casein kinase 1 (CK1), cyclin-dependent kinase 5 (Cdk5), AMPA receptors, protein phosphatase-1 (PP-1), protein phosphatase 2C (PP2C), protein phosphatase 2B (PP2B) and/or protein phosphatase 2A (PP2A), for use in such treatments. The present invention also relates to methods of modulating phosphorylation-dependent activation of AMPA receptors for use in such treatments.

2. BACKGROUND OF THE INVENTION

Depression is among the most debilitating psychiatric disorders, yet few pharmacological approaches exist for treating depression. Tricyclic antidepressants, which inhibit serotonin and noradrenaline reuptake transporters, and monoamine oxidase inhibitors, which inhibit the major catabolic enzyme for monoamine neurotransmitters, have been available for over 50 years. Another treatment strategy that has been utilized for many years is electroconvulsive seizure therapy. More recently, selective serotonin reuptake inhibitors have been developed. Nevertheless, today's treatments are sub-optimal, with only approximately 50% of all patients demonstrating complete remission, although more (up to 80%) show partial responses (Nestler et al., 2002; Neuron 34, 13-25). There therefore exists an urgent need for novel strategies for the treatment of depression.

Serotonergic pathways in the brain have been well-established as critical for regulation of mood and depletion of serotonin in brain cells has been associated with production of behavioral depression (Cooper et al. 1991. The Biochemical Basis of Neuropharmacology, 6th Edition. Oxford university Press: New York, pages 338-366). As a result, pharmacological research has focused on development of compounds that alter serotonergic function as a way to treat depression. Serotonin (also known as 5-HT or 5HT) acts on neuronal tissue to elicit its responses through the actions of specific receptors. Serotonin released from a presynaptic neuron acts at specific receptors on the postsynaptic neuron. Most of the current treatment paradigms for depression involves modulation of serotonergic neurotransmission through the usage of agents that alter the level of serotonin in the synaptic cleft.

Fifteen types of serotonin receptors have been identified in mammalian CNS tissue, cloned and pharmacologically characterized (Barnes et al., 1999, Neuropharmacology 38, 1083-1152). They are divided into seven different subclasses: 5-HT1A-F, 5-HT2A-C, 5-HT3A-B, 5-HT4, 5-HT5, 5-HT6 and 5-HT7 receptors. All of them are metabotropic receptors, with the exception of 5-HT3 receptors, which are ionotropic. These serotonin receptors act via the following second messenger systems: 5-HT1-class receptors and 5-HT5A and B receptors decrease cAMP formation; 5-HT2-class receptors increase inositol triphosphate and diacylglycerol formation; 5-HT3 receptors increase $Na^+$ and $Ca^{2+}$ influx; and 5-HT4, 5-HT6, and 5-HT7 receptors increase cAMP formation. Thus, serotonin can activate multiple second messenger systems, and as a consequence, the action of most anti-depressants is rather non-specific.

So far, there are no specific agonist or antagonists that act at any of the serotonin receptors that have shown a better therapeutic profile than the currently employed anti-depressants. This indicates that an altered activity at multiple serotonin receptors may be needed for anti-depressants to achieve their effects and that the antidepressant properties are achieved by the integration of several neurotransmitter-mediated intracellular signaling cascades within the postsynaptic neuron.

Proteins that integrate the effects of multiple serotonin receptors may therefore be involved in the anti-depressant efficacy of tricyclic antidepressants, selective serotonin reuptake inhibitors and/or monoamine oxidase inhibitors. One such protein, DARPP-32, (Dopamine- and cAMP-regulated phosphoprotein, Mr 32,000) was discovered as a major target for dopamine and cAMP in the brain (Walaas et al. 1983. Nature 301:69-71). DARPP-32 is enriched in the two major projection areas for dopaminergic neurons, the prefrontal cortex and the striatum. Prefrontal cortex and the striatum receive a moderate to high serotonergic innervation (Steinbusch, 1981, Neuroscience 6, 557-618), which is further increased when the levels of dopamine in this region are decreased (Rozas et al., 1998, Neurosci. Lett. 245, 151-154). Several serotonin receptors, most notably 5-HT1B, 5-HT1E, 5-HT2A, 5-HT2C, 5-HT3, 5-HT4, and 5-HT6, are expressed in striatum (Barnes et al., 1999, Neuropharmacology 38, 1083-1152).

Over the past years it has been established that DARPP-32 plays an obligatory role in the biochemical, electrophysiological, transcriptional, and behavioral effects of dopamine (Greengard, P. et al. 1999. Neuron 23:435-447). Dopamine, via D1 receptor-mediated activation of protein kinase A (PKA), phosphorylates DARPP-32 at Thr34 and thereby converts DARPP-32 into a potent inhibitor of protein phosphatase-1 (PP-1) (Walaas et al. 1983. Nature 301:69-71; Hemmings et al. 1984. Nature 310:503-505). Phospho-DARPP-32 is dephosphorylated by PP2B (also termed calcineurin). Additional kinases and phosphatases have been shown to phosphorylate DARPP-32 at distinct sites and to regulate its function.

Casein Kinase 1 (CK1) was one of the first serine/threonine protein kinases to be isolated and characterized (Gross, S. D. and R. A. Anderson. 1998. Cell Signal 10:699-671). It is a ubiquitous enzyme that can be found in the nucleus and the cytosol of cells and bound to the cytoskeleton or to cell membranes. In the central nervous system (CNS), CK1 appears to play a role in regulation of circadian rhythm (Camacho, F. et al. 2001. FEBS Lett. 489:159-165) and intracellular trafficking (Murakami, A. et al. 1999. J. Biol. Chem. 274:3804-3810; Panek, H. R. et al. 1997. EMBO J. 16:4194-4204; Wang, X. et al. 1996. Mol. Cell. Biol. 16:5375-5385). In the neostriatum, CK1 has been found to phosphorylate DARPP-32 at Ser137 (Desdouits, F. et al. 1995. J. Biol. Chem. 270:8772-8778). Phosphorylation of Ser137 influences the ability of phospho-Thr34 to be dephosphorylated by PP2B (Desdouits, F. et al. 1995. Proc. Natl. Acad. Sci. USA 92:2682-2685; Desdouits, F. et al. 1998. Biochem. J. 330:211-216). PP2C is also involved in this complex and in regulating the state of DARPP-32 phosphorylation at Thr34, since PP2C decreases phosphorylation of DARPP-32 at the Ser137 site (Desdouits et al. 1998. Biochem. J. 330:211-216).

In addition to PP2B, PP2C and CK1, cyclin-dependent kinase 5 (cdk5) and PP2A are also involved in regulating the state of phosphorylation of DARPP-32. Cdk5 was originally identified as a homologue of $p34^{cdc2}$ protein kinase. Subsequent studies have shown that unlike cdc2, cdk5 kinase activity is not detected in dividing cells. Instead, the active form of cdk5 is present only in differentiated neurons, where it associates with a neuron-specific 35 kDa regulatory subunit, termed p35. Cdk5/p35 plays a variety of roles in the developing and adult nervous system. Recent studies have linked mis-regulation of cdk5 to Alzheimer's disease (Kusakawa, G. et al. 2000. J. Biol. Chem. 275:17166-17172; Lee, M. S. et al. 2000. Nature 405:360-364; Nath, R. et al. 2000. Biochem. Biophys. Res. Commun. 274:16-21; Patrick, G. N. et al. 1999. Nature 402:615-622). In these studies, conversion of p35 to p25 by the action of calpain causes prolonged activation and altered localization of cdk5. In turn, cdk5/p25 can hyperphosphorylate tau, disrupt cytoskeletal structure and promote apoptosis of primary neurons.

Recent studies have also shown that cdk5 phosphorylates DARPP-32 at Thr75 (Nishi, A. et al. 2000. Proc. Natl. Acad. Sci. USA 97:12840-12845; Bibb, J. A. et al. 1999. Nature 402:669-671). DARPP-32 phosphorylated at Thr75 is an inhibitor of PKA (Bibb et al. 1999. Nature 402:669-671). Phosphorylation of DARPP-32 at Thr75 by cdk5, by inhibiting PKA, decreases phosphorylation of Thr34 in DARPP-32 by PKA and plays an important modulatory role in the DARPP-32/PP1 cascade (Bibb, J. A. et al. 1999. Nature 402:669-671). Phospho-Thr75 is dephosphorylated by PP2A. The available evidence indicates that dopamine decreases phosphorylation of DARPP-32 at Thr75 by activating PKA which, in turn, activates PP2A and thereby increases the efficacy of the DARPP-32/PP1 signaling cascade (Nishi et al. 2000. Proc. Natl. Acad. Sci. USA 97:12840-12845).

Another study has linked the total levels of DARPP-32 with the pharmacological activity of certain anti-depressant compounds (Guitart, X. and E. J. Nestler. 1992. J. Neurochem. 59:1164-1167). These researchers demonstrated that chronic administration of lithium, imipramine, and tranylcypromine in rats produced significant increases in frontal cortex levels of DARPP-32 immunoreactivity, while administration of haloperidol, morphine, and cocaine were without effects on DARPP-32 immunoreactivity. Lithium is used for treatment of manic-depressive illness, while imipramine and tranylcypromine are anti-depressants. Imipramine acts by inhibiting norepinephrine re-uptake while tranylcypromine is a monoamine oxidase inhibitor.

Although research has focused on specific agonists and antagonists for these receptors and the way that serotonergic function is then modulated by these agonists and antagonists, little is known about the variety of intracellular signaling pathways linked to serotonin activity or about drugs that may be used to treat disorders related to the function of serotonergic intracellular signaling pathways. Therefore, there is an urgent need to provide new drug assays that can be used to develop novel drugs that can be used to treat disorders related to function of serotonergic intracellular signaling pathways.

2.1. Protein Phosphatase-2C ("PP2C")

PP2C belongs of a large family of Ser/Thr phosphatases. However, it is a highly exceptional member of this family. PP2C does not possess any significant homology to other phosphatases in the family, such as PP-1, protein phosphatase 2A (PP2A), or calcineurin (PP2B). Unlike most of these phosphatases, it contains a single polypeptide chain and is not sensitive to any known Ser/Thr phosphatase inhibitors, e.g., okadaic acid (Bialojan and Takai, 1988, Biochem. J. 256, 283-290), calyculin (Hishiya et al., 1999, J. Biol. Chem. 274, 26705-26712) or microcystin (MacKintosh et al., 1990, FEBS Lett. 264, 187-192). Hence, PP2C has been categorized in separate subfamily from other Ser/Thr phosphatases (Price and Mumby, 1999, Curr. Opin. Neurobiol. 9, 336-342).

In the past decade, the PP2C subfamily of phosphatases has diversified owing to the discovery of array of isoforms, cloned from a variety of tissues and designated as alpha, beta, gamma, delta and NERPP (Tamura et al., 1989, Proc. Natl. Acad. Sci. USA 86, 1796-1800; Wenk et al., 1992, FEBS Lett. 297, 135-138; Marley et al., 1998, FEBS Lett. 431, 121-124; Travis and Welsh, 1997, FEBS Lett. 412, 415-419; Tong et al., 1998, J. Biol. Chem. 273, 35282-35290; Labes et al., 1998, Cell. Mol. Biol. (Noisy-le-grand) 41, 917-923). Although these isoforms differ significantly in primary amino acid sequence, metal dependence, and localization, all of them share a few common features. All isoforms contain several conservative domains, required for phosphate and metal binding (Das et al., 1996, EMBO J. 15, 6798-6809). Presence of $Mg^{2+}$ or $Mn^{2+}$ ions is essential for enzymatic activity of all isoforms, except for delta, which is strictly $Mn^{2+}$-dependent, when expressed in vitro (Tong et al., 1998, J. Biol. Chem. 273, 35282-35290).

Although exact mechanisms that regulate PP2C activity have not been identified yet, it is clear that PP2C plays a role in cell cycle progression (Cheng et al., 1999, Trends Biochem. Sci. 22, 245-251), stress signaling pathways (Takekawa et al., 1998, EMBO J. 17, 4744-4752; Takekawa et al, 2000, EMBO J. 19, 6517-6526; Hanada et al., 2001, J. Biol. Chem. 276, 5753-5759), and formation of the actin cytoskeleton (Hishiya et al., 1999, J. Biol. Chem. 274, 26705-26712). Overexpression of PP2C causes drastic morphological changes and eventually results in apoptosis (Tong et al., 1998, J. Biol. Chem. 273, 35282-35290).

Since PP2C is widely expressed in brain, it is likely to play an important role in the regulation of synaptic activity. However, very few neuronal substrates of PP2C have been characterized to date. One probable substrate of PP2C is cAMP-dependent protein kinase II (CAMK II), which is dephosphorylated by PP2C at the site of autophosphorylation (Fukunaga et al., 1993, J. Biol. Chem. 268, 133-137; Strack et al., 1997, J. Biol. Chem. 272, 13467-13470). Another neuronal substrate of PP2C is DARPP 32. This protein is highly abundant in striatonigral neurons (estimated concentration, 50 μM) and has multiple serine/threonine phosphorylation sites (Greengard, 2001, Science 294, 1024-1030). When phosphorylated at Thr34 by protein kinase A (PKA), it becomes a potent inhibitor of PP-1 (Hemmings et al., 1984, Nature 310, 503-505). When Thr75 is phosphorylated, DARPP 32 evolves into a strong inhibitor of PKA (Bibb et al., 1999, Nature 402, 669-671). Thus, DARPP 32 plays a dual role of a kinase/phosphatase inhibitor depending upon its phosphorylation state at Thr34 and Thr75. Stimulation of metabotropic glutamate receptors activates casein kinase 1 (CK1), which phosphorylates Ser137 residue of DARPP 32 (Liu et al., 2001, Proc. Natl. Acad. Sci. USA 98, 11062-11068). Phosphorylation of Ser137 inhibits dephosphorylation of Thr34 by calcineurin (PP2B) (Desdouits et al., 1998, Biochem. J. 330, 211-216). PP2C isolated from rat liver dephosphorylates Ser137, thus indirectly affecting activity of PP-1 (Desdouits et al., 1998, Biochem. J. 330, 211-216).

Surprisingly little is known about the regulation of CK1, Cdk5, AMPA receptor, PP-1, PP2C, PP2B or PP2A by first messengers and other signaling events. Therefore, there is a need in the art to provide new methods of screening that can be used to develop novel compositions or drugs that can be used to treat diseases or disorders related to the regulation of serotonergic intracellular signaling molecules, CK1, Cdk5, AMPA receptor, PP-1, PP2C, PP2B or PP2A. Furthermore, there is a need to develop treatments for such diseases or disorders that are due, at least in part, to an aberration or dysregulation of an intracellular signaling pathway regulated by CK1, Cdk5, AMPA receptor, PP-1, PP2C, PP2B or PP2A. The present invention provides such methods and compositions.

Citation or identification of any reference in Section 2, or in any other section of this application, shall not be considered an admission that such reference is available as prior art to the present invention.

3. SUMMARY OF THE INVENTION

The present invention provides a method for modulating casein kinase 1 ("CK1" or "CK1"), cyclin-dependent kinase 5 ("Cdk5, " "cdk5" or "CDK5"), protein phosphatase 1 ("PP-1"), AMPA receptor ("AMPA"), protein phosphatase-2C ("PP2C"), protein phosphatase-2B ("PP2B") or protein phosphatase-2A ("PP2A") activity in a cell or tissue of interest, comprising contacting the cell or tissue of interest with an effective amount of a compound that alters the activity of a serotonergic receptor (5-HTR) intracellular signaling molecule, wherein contact of the cell or tissue with the compound results in a modulation of the activity of CK1, Cdk5, AMPA receptor, PP-1, PP2C, PP2B and/or PP2A. In certain embodiments, contact of said cell or tissue with the compound results in a modulation of the activity of PP2C and/or PP2A and in other embodiments, the compound binds to PP2C and/or PP2A.

The present invention provides a method for modulating activity of AMPA receptors comprising administering (for example, to an individual, patient or animal) an effective amount of a compound of the invention, for example, a compound identified by the methods of the invention, wherein the compound modulates the activity of CK1, Cdk5, PP-1, PP2C, PP2B and/or PP2A and wherein modulation of CK1, Cdk5, PP-1, PP2C, PP2B and/or PP2A activity results in an alteration in the activity of AMPA receptors in the neuron. In a specific embodiment, AMPA receptors are in an excitable cell, e.g., a neuron. In another embodiment, the method involves administration of a 5-HTR agonist or antagonist in order to modulate activity of CK1, Cdk5, PP-1, PP2C, PP2B and/or PP2A and thereby alter activity of the AMPA receptors.

The present invention provides, in vivo, in situ, and in vitro, methods of identifying an agent, drug or compound for modulating the activity of CK1, Cdk5, AMPA receptor, PP-1, PP2C, PP2B and/or PP2A in a cell or tissue of interest. In certain embodiments, the method comprises identifying an agent to be tested for an ability to treat a 5-HTR-related or DA-related disorder. Such methods can be used alone or in conjunction with each other. In one embodiment, the method comprises determining a first level of CK1, Cdk5, AMPA receptor, PP-1, PP2C, PP2B and/or PP2A activity in a cell or tissue of interest; contacting the cell or tissue with a test compound; and determining a second level of CK1, Cdk5, AMPA receptor, PP-1, PP2C, PP2B and/or PP2A activity in the cell or tissue, wherein a difference in the first level and the second level of CK1, Cdk5, AMPA receptor, PP-1, PP2C, PP2B and/or PP2A activity is indicative of the ability of the test compound to modulate CK1, Cdk5, AMPA receptor, PP-1, PP2C, PP2B and/or PP2A activity.

In another embodiment, the method comprises determining a first level of CK1, Cdk5, PP-1, PP2C, PP2B and/or PP2A activity in a cell or tissue of interest; determining a first level of AMPA receptor activity in the cell or tissue; contacting the cell or tissue with a test compound; determining a second level of CK1, Cdk5, PP-1, PP2C, PP2B and/or PP2A activity in the cell or tissue; and determining a second level of AMPA receptor activity in the cell or tissue, wherein a difference in the first level and the second level of CK1, Cdk5, PP-1, PP2C, PP2B and/or PP2A activity, respectively and a difference in the first level and the second level of AMPA receptor activity are indicative of the ability of the test compound to modulate the activity of AMPA receptors.

In another embodiment, the invention provides a method for treating a 5-HT-related or DA-related disorder in a patient in need thereof comprising administering to the patient an agent that increases the phosphorylation of Thr34-phosphorylated DARPP-32 or Ser137-phosphorylated DARPP-32, or that decreases the phosphorylation of Thr75-phosphorylated DARPP-32, wherein the agent increases the activity of a serotonergic intracellular signaling pathway molecule.

The present invention also provides in vivo methods of identifying agents that can modulate the activity of an serotonergic intracellular signaling pathway via modulation of CK1, Cdk5, AMPA receptor, PP-1, PP2C, PP2B and/or PP2A activity. Such methods can be employed alone or in conjunction with in vitro and in situ methods as disclosed herein. One such method comprises administering the agent to a non-human mammal. The amount (and/or rate) of activation of CK1, Cdk5, AMPA receptor, PP-1, PP2C, PP2B and/or PP2A is then determined. An agent is identified as capable of modulating the activity of a serotonergic intracellular signaling pathway via modulation of CK1, Cdk5, AMPA receptor, PP-1, PP2C, PP2B and/or PP2A when the amount (and/or rate) of activation is increased or decreased in the presence of the agent relative to in the absence of the agent. In preferred embodiments, the non-human mammal is a rodent. In a more preferred embodiment, the rodent is a mouse.

The invention also provides methods of screening potential agents (or drugs or compounds) in order to select an agent that can potentially ameliorate and/or be used in treatment of a 5-HTR-related disorder, a DA-related disorder, a CK1-related disorder, a Cdk5-related disorder, a AMPA-receptor-related disorder, or a PP-1-, PP2C-, PP2B- and/or PP2A-related disorder.

The present invention also provides methods of identifying agents (or drugs or compounds), e.g., drug screening assays, which drugs may be used in therapeutic methods for the treatment of a 5-HTR-related disorder, a DA-related disorder, a CK1-related disorder, a Cdk5-related disorder, a AMPA-receptor-related disorder, or a PP-1-, PP2C-, PP2B- and/or PP2A-related disorder. In a specific embodiment, the method comprises detecting the increase (or decrease) in the amount of phosphorylation (or dephosphorylation) of Thr34-phosphorylated DARPP-32, Ser137-phosphorylated DARPP-32, or Thr75-phosphorylated DARPP-32.

In another embodiment, the invention provides a method for treating a 5-HT-related or DA-related disorder in a patient in need thereof comprising administering to the patient an agent that alters the phosphorylation of phosphorylated DARPP-32, wherein the agent modulates the activity of CK1, Cdk5, AMPA receptor, PP-1, PP2C, PP2B and/or PP2A.

In another embodiment, the invention provides a method for identifying an agent for use in the treatment of a 5-HT-related or DA-related disorder in a patient in need of such treatment comprising: (a) contacting a potential agent with Cdk5 and Thr75-dephosphorylated DARPP-32; and (b) detecting the amount of phosphorylation of Thr75-dephosphorylated DARPP-32; wherein the agent is identified if a decrease in the phosphorylation of Thr75-dephosphorylated DARPP-32 is detected in the presence of the potential agent.

In another embodiment, the invention provides a method for treating a 5-HT-related or DA-related disorder in a patient in need thereof comprising administering to the patient an agent that decreases the dephosphorylation of Thr34-phosphorylated DARPP-32, wherein the agent decreases PP-1 activity.

In another embodiment, the invention provides a method for identifying an agent for use in the treatment of 5-HT-related or DA-related disorder in a patient in need of such treatment comprising: (a) contacting a potential agent with PP-1 and Thr34-phosphorylated DARPP-32; and (b) detecting the amount of dephosphorylation of Thr34-phosphorylated DARPP-32; wherein the agent is identified if a decrease in the dephosphorylation of Thr34-phosphorylated DARPP-32 is detected in the presence of the potential agent.

In another embodiment, the invention provides a method for treating a 5-HT-related disorder or DA-related in a patient in need thereof comprising administering to the patient an agent that decreases the dephosphorylation of Ser137-phosphorylated DARPP-32, wherein the agent decreases PP2C activity.

In another embodiment, the invention provides a method for identifying an agent for use in the treatment of 5-HT-related or DA-related disorder in a patient in need of such treatment comprising: (a) contacting a potential agent with PP2C and Ser137-phosphorylated DARPP-32; and (b) detecting the amount of dephosphorylation of Ser137-phosphorylated DARPP-32; wherein the agent is identified if an decrease in the dephosphorylation of Ser137-phosphorylated DARPP-32 is detected in the presence of the potential agent.

In another embodiment, the invention provides a method for treating a 5-HT-related or DA-related disorder in a patient in need thereof comprising administering to the patient an agent that inhibits the dephosphorylation of Thr34-phosphorylated DARPP-32, wherein the agent decreases PP2B activity.

In another embodiment, the invention provides a method for identifying an agent for use in the treatment of 5-HT-related disorder or DA-related in a patient in need of such treatment comprising: (a) contacting a potential agent with PP2B and Thr34-phosphorylated DARPP-32; and (b) detecting the amount of dephosphorylation of Thr34-phosphorylated DARPP-32; wherein the agent is identified if a decrease in the dephosphorylation of Thr34-phosphorylated DARPP-32 is detected in the presence of the potential agent.

In another embodiment, the invention provides a method for treating a 5-HT-related or DA-related disorder in a patient in need thereof comprising administering to the patient an agent that increase the dephosphorylation of Thr75-phosphorylated DARPP-32, wherein the agent increases PP2A activity.

In another embodiment, the invention provides a method for identifying an agent for use in the treatment of 5-HT-related or DA-related disorder in a patient in need of such treatment comprising: (a) contacting a potential agent with PP2A and Thr75-phosphorylated DARPP-32; and (b) detecting the amount of dephosphorylation of Thr75-phosphorylated DARPP-32; wherein the agent is identified if an increase in the dephosphorylation of Thr75-phosphorylated DARPP-32 is detected in the presence of the potential agent.

In another embodiment, the invention provides a method for regulating phosphorylation-dependent activation of AMPA receptors in a cell comprising administering an effective amount of a compound that modulates activity of CK1, Cdk5, PP-1, PP2C, PP2B and/or PP2A, wherein modulation of the activity of CK1, Cdk5, PP-1, PP2C, PP2B and/or PP2A results in an alteration in the phosphorylation-dependent activation of AMPA receptors in the cell.

The present invention also provides compositions for modulating the activity of CK1, Cdk5, AMPA receptor, PP-1, PP2C, PP2B and/or PP2A.

The present invention further provides methods for performing rational drug design to develop drugs that can modulate activity of CK1, Cdk5, AMPA receptor, PP-1, PP2C, PP2B and/or PP2A and thereby ameliorate a 5-HTR-related disorder, a CK1-related disorder, a Cdk5-related disorder, a AMPA-receptor-related disorder, or a PP-1-, PP2C-, PP2B- and/or PP2A-related disorder.

In one embodiment, the invention provides methods of identifying a compound that modulates the activity of casein kinase 1 in a cell or tissue of interest comprising: (a) determining a first level of casein kinase 1 activity in said cell or tissue; (b) contacting said cell or tissue with a test compound; and (c) determining a second level of casein kinase 1 activity in said cell or tissue, wherein a difference in said first level and said second level of casein kinase 1 activity is indicative of the ability of said test compound to modulate casein kinase 1 activity, and wherein modulation of casein kinase 1 activity is regulated by modulation of the activity of a 5-HTR intracellular signaling pathway.

In one embodiment, the invention provides methods of identifying a compound that modulates the activity of cyclin-dependent kinase 5 in a cell or tissue of interest comprising: (a) determining a first level of cyclin-dependent kinase 5 activity in said cell or tissue; (b) contacting said cell or tissue with a test compound; and (c) determining a second level of cyclin-dependent kinase 5 activity in said cell or tissue, wherein a difference in said first level and said second level of cyclin-dependent kinase 5 activity is indicative of the ability of said test compound to modulate cyclin-dependent kinase 5 activity, and wherein modulation of cyclin-dependent kinase 5 activity is regulated by modulation of the activity of a 5-HTR intracellular signaling pathway.

In one embodiment, the invention provides methods of identifying a compound that modulates the activity of AMPA receptors in a cell or tissue of interest comprising: (a) determining a first level of AMPA receptor activity in said cell or tissue; (b) contacting said cell or tissue with a test compound; and (c) determining a second level of AMPA receptor activity in said cell or tissue, wherein a difference in said first level and said second level of AMPA receptor activity is indicative of the ability of said test compound to modulate AMPA receptor activity, and wherein modulation of AMPA receptor activity is regulated by modulation of the activity of a 5-HTR intracellular signaling pathway.

In one embodiment, the invention provides methods of identifying a compound that modulates the activity of PP-1 in a cell or tissue of interest comprising: (a) determining a first level of PP-1 activity in said cell or tissue; (b) contacting said cell or tissue with a test compound; and (c) determining a second level of PP-1 activity in said cell or tissue, wherein a difference in said first level and said second level of PP-1 activity is indicative of the ability of said test compound to modulate PP-1 activity, and wherein modulation of PP-1 activity is regulated by modulation of the activity of a 5-HTR intracellular signaling pathway.

In one embodiment, the invention provides methods of identifying a compound that modulates the activity of PP2C in a cell or tissue of interest comprising: (a) determining a first level of PP2C activity in said cell or tissue; (b) contacting said cell or tissue with a test compound; and (c) determining a second level of PP2C activity in said cell or tissue, wherein a difference in said first level and said second level of PP2C activity is indicative of the ability of said test compound to modulate PP2C activity, and wherein modulation of PP2C activity is regulated by modulation of the activity of a 5-HTR intracellular signaling pathway.

In one embodiment, the invention provides methods of identifying a compound that modulates the activity of PP2B in a cell or tissue of interest comprising: (a) determining a first level of PP2B activity in said cell or tissue; (b) contacting said cell or tissue with a test compound; and (c) determining a second level of PP2B activity in said cell or tissue, wherein a difference in said first level and said second level of PP2B activity is indicative of the ability of said test compound to modulate PP2B activity, and wherein modulation of PP2B activity is regulated by modulation of the activity of a 5-HTR intracellular signaling pathway.

In one embodiment, the invention provides methods of identifying a compound that modulates the activity of PP2A in a cell or tissue of interest comprising: (a) determining a first level of PP2A activity in said cell or tissue; (b) contacting said cell or tissue with a test compound; and (c) determining a second level of PP2A activity in said cell or tissue, wherein a difference in said first level and said second level of PP2A activity is indicative of the ability of said test compound to modulate PP2A activity, and wherein modulation of PP2A activity is regulated by modulation of the activity of a 5-HTR intracellular signaling pathway.

The present invention also provides diagnostic and therapeutic methods for the treatment of a 5-HTR-related disorder, a CK1-related disorder, a Cdk5-related disorder, a AMPA-receptor-related disorder, or a PP-1-, PP2C-, PP2B- and/or PP2A-related disorder, including, but not limited the use of compositions or compounds of the invention in the treatment of a 5-HTR-related disorder, a CK1-related disorder, a Cdk5-related disorder, a AMPA-receptor-related disorder, or a PP-1-, PP2C-, PP2B- and/or PP2A-related disorder.

In one aspect, the invention provides a method for treating a neuronal condition characterized by modulation of a serotonergic intracellular signaling pathway comprising administering to a subject in need of such treatment an effective amount of a compound of the present invention to modulate CK1, Cdk5, AMPA receptor, PP-1, PP2C, PP2B and/or PP2A activity, and thus increase or decrease AMPA receptor activity and/or the activity of a DA intracellular signaling pathway via modulation of a 5-HTR intracellular signaling pathway.

In certain embodiments, the 5-HTR intracellular signaling pathway comprises: (i) activation of 5-HT4 and 5-HT6 receptors, which increases cAMP activation of PKA phosphorylation of Thr-34; (ii) activation of 5-HT4 and 5-HT6 receptors, which increases cAMP activation of PKA activation of protein phosphatase-2A (PP-2A) dephosphorylation of Thr-75; and/or (iii) activation of 5-HT2 receptors, which increases activation of PLC, which in turn increases calcium activation of CK1 dependent phosphorylation of Ser-137.

Thus any compound identified according to the methods of the invention that affects these interactions may also serve as the basis of a therapeutic treatment for a 5-HTR-related disorder, and therefore, all of the proteins that participate in such interactions may also be used in assays as described herein.

The present invention provides methods for treating a 5-HTR-related disorder, a CK1-related disorder, a Cdk5-related disorder, a AMPA-receptor-related disorder, or a PP-1-, PP2C-, PP2B- and/or PP2A-related disorder in an individual (e.g., a patient) or an animal subject by administering an effective amount of a compound of the invention to modulate CK1, Cdk5, AMPA receptor, PP-1, PP2C, PP2B and/or PP2A activity. In one embodiment, the agent promotes or increases the activity of CK1, Cdk5, AMPA receptor, PP-1, PP2C, PP2B and/or PP2A. In another embodiment, the agent inhibits or decreases the activity of CK1, Cdk5, AMPA receptor, PP-1, PP2C, PP2B and/or PP2A.

In certain embodiments, the invention provides a method for treating a 5-HT-related disorder in a patient in need thereof comprising administering to the patient an agent that modulates the phosphorylation of DARPP-32 at Thr34, Thr75 and/or Ser137, wherein the agent modulates the activity of CK1, Cdk5, AMPA receptor, PP-1, PP2C, PP2B and/or PP2A. In specific embodiments, the agent modulates the activity by binding to CK1, Cdk5, AMPA receptor, PP-1, PP2C, PP2B and/or PP2A.

In certain embodiments, binding is measured under standard art-known physiological conditions.

The invention provides methods of administering an agent (or drug or compound) of the invention that can ameliorate a symptom of a 5-HTR-related disorder, a CK1-related disorder, a Cdk5-related disorder, a AMPA-receptor-related disorder, or a PP-1-, PP2C-, PP2B- and/or PP2A-related disorder, disease and/or condition in a patient or subject exhibiting the symptom. In certain embodiments, the invention provides methods of administering an agent identified by the methods disclosed herein, that can ameliorate a symptom of a 5-HTR-related disorder, a CK1-related disorder, a Cdk5-related disorder, a AMPA-receptor-related disorder, or a PP-1-, PP2C-, PP2B- and/or PP2A-related disorder in a patient or subject exhibiting the symptom. In other embodiments, an agonist of 5-HTR activity can be used to for treating a 5-HTR-related disorder, a CK1-related disorder, a Cdk5-related disorder, a AMPA-receptor-related disorder, or a PP-1-, PP2C-, PP2B- and/or PP2A-related disorder. In yet other embodiments, an antagonist of 5-HTR activity can be used to for treating a 5-HTR-related disorder, a CK1-related disorder, a Cdk5-related disorder, a AMPA-receptor-related disorder, or a PP-1-, PP2C-, PP2B- and/or PP2A-related disorder.

The present invention also provides compositions for modulating the activity of CK1, Cdk5, AMPA receptor, PP-1, PP2C, PP2B and/or PP2A. The invention also provides compositions for modulating the activity of AMPA receptors via modulation of the activity of CK1, Cdk5, AMPA receptor, PP-1, PP2C, PP2B and/or PP2A. The present invention also provides pharmaceutical compositions of the agents (or drugs or compounds) of the invention disclosed herein. The invention encompasses pharmaceutical compositions for regulating CK1, Cdk5, AMPA receptor, PP-1, PP2C, PP2B and/or PP2A activity, and for diagnosing or treating a 5-HTR-related disorder, a CK1-related disorder, a Cdk5-related disorder, a AMPA-receptor-related disorder, or a PP-1-, PP2C-, PP2B- and/or PP2A-related disorder. Because in certain embodiments, a decrease of normal function can produce the development of a phenotype of the above-listed diseases or disorders (e.g., depression), activation of a serotonergic receptor (5-HTR) signaling pathway, or an increase in CK1, Cdk5, AMPA receptor, PP-1, PP2C, PP2B and/or PP2A (e.g., downstream activation) facilitates amelioration of a symptom in individuals exhibiting a symptom of such a disorder (e.g., depression).

The present invention also provides compositions for modulating the activity of a dopaminergic intracellular signaling pathway by modulating a serotonergic intracellular signaling pathway. The present invention also provides pharmaceutical compositions of the agents (or drugs or compounds) of the invention disclosed herein. The invention encompasses pharmaceutical compositions for modulating the activity of a dopaminergic intracellular signaling pathway by modulating a serotonergic intracellular signaling pathway, and for diagnosing or treating a DA-related disorder. Because in certain embodiments, a decrease of normal dopaminergic function can produce the development of a phenotype of a DA-related disorder (e.g., Parkinson's disease), activation of DARPP-32 via a serotonergic intracellular signaling pathway, or by modulating the activity of CK1, Cdk5, AMPA receptor, PP-1, PP2C, PP2B and/or PP2A, can facilitate amelioration of a symptom in individuals exhibiting a symptom of DA-related disorder that is independent of enhanced dopaminergic neurotransmission. Thus according to the invention, agents that enhance serotonergic neurotransmission or the activity of a serotonergic intracellular signaling pathway, or that modulate the activity of CK1, Cdk5, AMPA receptor, PP-1, PP2C, PP2B and/or PP2A, can thus exert ameliorative effects independent of dopamine, and can be used in the treatment of DA-related disorders.

3.1. Definitions

As used herein, the term "modulate" or "modulation" shall have its usual meaning, and encompasses the meanings of the words "enhance," "inhibit," and "mimic." "Modulation" of activity may be either an increase or a decrease in activity.

As used herein, an "agonist" is any compound that acts directly or indirectly through or upon a receptor to produce a pharmacological effect, while an "antagonist" is any compound that blocks the stimulation of a receptor and its resulting pharmacological effect.

As used herein, an "effective amount" of a modulatory compound is an amount that can be determined by one of skill in the art based on data from studies using methods of analysis such as those disclosed herein. Such data may include, but not be limited to, results from IC50 determinations, as discussed below in Section 5.6.

As used herein, a "serotonergic intracellular signaling pathway" is used interchangeably with "serotonergic intracellular signaling cascade," "serotonergic signaling cascade," "5-HT receptor intracellular signaling pathway," "5-HTR intracellular signaling pathway" or analogous abbreviations.

As used herein, the term "DARPP-32" is used interchangeably with "Dopamine- and cyclic AMP (cAMP)-Regulated PhosphoProtein" and "DARPP32" and is a 32 kilodalton cytosolic protein that is selectively enriched in medium-sized spiny neurons in neostriatum. The human, mouse, rat and bovine DARPP-32 amino acid sequences are disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties (see SEQ ID NOS: 1-4, respectively).

As used herein, the term "Thr75 DARPP-32" is used interchangeably with "Thr75 DARPP32, " "thr$^{75}$ DARPP-32", "Threonine-75 DARPP-32" and "threonine-75 DARPP-32" along with analogous abbreviations, and denotes the seventy-fifth amino acid residue in the amino sequence of DARPP-32 as disclosed by Brene et al. (J. Neurosci. 14:985-998 (1994)) having the GenBank Accession of AAB30129.1, which is a threonine residue that, as disclosed herein, can be phosphorylated by Cdk5.

As used herein, the term "phospho-Thr75 DARPP-32, " or analogous abbreviations as disclosed above, denotes the phosphorylated form of Thr75 DARPP-32.

As used herein, the term "Thr34 DARPP-32" is used interchangeably with "Thr34 DARPP32, " "thr$^{34}$ DARPP-32" "Threonine-34 DARPP-32" and "threonine-34 DARPP-32" along with analogous abbreviations and denotes the thirty-fourth amino acid residue of the amino sequence of DARPP-32 as disclosed by Brene et al. (J. Neurosci. 14:985-998 (1994)) having the GenBank Accession No. of AAB30129.1, which is a threonine residue that can be phosphorylated by the cyclic AMP dependent protein kinase (PKA).

As used herein, the term "phospho-Thr34 DARPP-32, " or analogous abbreviations as disclosed above, denotes the phosphorylated form of Thr34 DARPP-32.

As used herein, the term "Ser137 DARPP-32" is used interchangeably with "Ser137 DARPP32, " "ser$^{137}$ DARPP-32", "Serine-137 DARPP-32" and "serine-137 DARPP-32" along with analogous abbreviations and denotes the one-hundred and thirty-seventh amino acid residue of the amino sequence of DARPP-32 as disclosed by Brene et al. (J. Neurosci. 14:985-998 (1994)) having the GenBank Accession No. of AAB30129.1, which is a serine residue that can be phosphorylated by CK1.

As used herein, the term "phospho-Ser137 DARPP-32" or analogous abbreviations as disclosed above, denotes the phosphorylated form of Ser137 DARPP-32.

As used herein, the terms "CK1, " "casein kinase I" or "CKI," are used interchangeably with or "casein kinase 1. " CK1 is a member of the serine/threonine protein kinases. CK1 includes, but is not limited to members of the CK1 (CKI) family of multiple isoforms, which are encoded by at least seven distinct genes (CKIα, β, γi, γ2, γ3, δ, ε; Desdouits, F. et al. 1995. J. Biol. Chem. 270:8772-8778; Gross et al., 1998, Cell Signal 10(10): 699-711; Vielhaber et al., 2001, IUBMB Life 51(2), 73-8).

As used herein, "an analog of CK1" is used interchangeably with "a homolog of CK1" and is a protein kinase that, like CK1, phosphorylates DARPP-32 on Ser137.

As used herein, the term "CK1 phosphorylatable fragment of DARPP-32" is a protein fragment of DARPP-32 that contains a serine residue that, when in the dephosphorylated form, can be phosphorylated by CK1. For human DARPP-32 having the amino acid sequence of SEQ ID NO:1, the serine residue is preferably Ser137 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Ser137. In another embodiment of this type, the peptide fragment comprises 7 consecutive amino acids from SEQ ID NO: 1 including Ser137. In an alternative embodiment the peptide fragment comprises between 10 and 25 consecutive amino acids from SEQ ID NO: 1 including Ser137. All of the peptide fragments can be part of fusion peptides or proteins. A CK1 phosphorylatable fragment of DARPP-32 can be prepared by any method commonly known in the art, e.g., cleaving (such as with a protease) and dephosphorylating the phosphorylated fragment from a larger fragment of phospho-Ser137 DARPP-32 protein or from the full-length phospho-Ser137 DARPP-32 protein. Thus the fragments can be synthesized by either standard peptide synthesis disclosed below, or generated through recombinant DNA technology or by classical proteolysis.

As used herein, the terms "CDK5", "Cdk5" or "cdk5" are used interchangeably with "cyclin-dependent kinase 5," which is also known as neuronal cyclin-dependent-like protein (Nclk) and tau protein kinase II (TPKII). Cdk5 is a member of the cyclin dependent kinases but atypically Cdk5 employs a non-cyclin cofactor called neuronal cyclin-dependent-like kinase 5 associated protein (Nck5a) rather than a cyclin. When the term "Cdk5" is used in descriptions of kinase reactions it should be understood that the active form, i.e., the "Cdk5/Nck5a complex" (disclosed hereinbelow) may be the actual catalytic factor and/or a fragment of Cdk5 that retains at least 10% of the catalytic activity of Cdk5.

As used herein, "an analog of Cdk5" is used interchangeably with "a homolog of Cdk5" and is a protein kinase that, like Cdk5, phosphorylates DARPP-32 on Threonine-75 but not on Threonine-34. One such analog is cdk1.

As used herein, "Nck5a" is used interchangeably with "neuronal cyclin-dependent-like kinase 5 associated protein" and is a non-cyclin cofactor for Cdk5. There are at least two isoforms of Nck5a in the brain (p35 and p39), which may also exist as proteolytic fragments (i.e., p25 and p29, respectively).

As used herein, the term "Cdk5/Nck5a complex" denotes the complex formed between Cdk5 and Nck5a, which is an active form of the Cdk5 kinase.

As used herein, the term "Cdk5 phosphorylatable fragment of DARPP-32" is a protein fragment of DARPP-32 that contains a threonine residue that when in the dephosphorylated form can be phosphorylated by Cdk5. For human DARPP-32 having the amino acid sequence of SEQ ID NO:1, the threonine residue is preferably Thr75 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Thr75. In another embodiment of this type, the peptide fragment comprises 7 consecutive amino acids from SEQ ID NO: 1 including Thr75. In an alternative embodiment the peptide fragment comprises between 10 and 25 consecutive amino acids from SEQ ID NO: 1 including Thr75. All of the peptide fragments can be part of fusion peptides or proteins. A Cdk5 phosphorylatable fragment of DARPP-32 can be prepared by any method commonly known in the art, e.g., cleaving (such as with a protease) and by phosphorylating the dephosphorylated fragment or by cleaving (such as with a protease) the phosphorylated fragment from a larger fragment of phospho-Thr75 DARPP-32 protein or from the full-length phospho-Thr75 DARPP-32 protein. Thus the fragments can be synthesized by either standard peptide synthesis disclosed below, or generated through recombinant DNA technology or by classical proteolysis.

As used herein, the term "PP2C dephosphorylatable fragment of DARPP-32" is a protein fragment of DARPP-32 that contains a serine residue that when in the phosphorylated form can be dephosphorylated by PP2C. For human DARPP-32 having the amino acid sequence of SEQ ID NO:1, the serine residue is preferably Ser137 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Ser137. In another embodiment of this type, the peptide fragment comprises 7 consecutive amino acids from SEQ ID NO: 1 including Ser137. In an alternative embodiment the peptide fragment comprises between 10 and 25 consecutive amino acids from SEQ ID NO: 1 including Ser137. All of the peptide fragments can be part of fusion peptides or proteins. A PP2C dephosphorylatable fragment of DARPP-32 can be prepared by any method commonly known in the art, e.g., cleaving (such as with a protease) and by phosphorylating the dephosphorylated fragment or by cleaving (such as with a protease) the phosphorylated fragment from a larger fragment of phospho-Ser137 DARPP-32 protein or from the full-length phospho-Ser137 DARPP-32 protein. Thus the fragments can be synthesized by either standard peptide synthesis disclosed below, or generated through recombinant DNA technology or by classical proteolysis.

As used herein, the term "PP2B dephosphorylatable fragment of DARPP-32" is a protein fragment of DARPP-32 that contains a threonine residue that when in the phosphorylated form can be dephosphorylated by PP2B. For human DARPP-32 having the amino acid sequence of SEQ ID NO:1, the threonine residue is preferably Thr34 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Thr34. In another embodiment of this type, the peptide fragment comprises 7 consecutive amino acids from SEQ ID NO: 1 including Thr34. In an alternative embodiment the peptide fragment comprises between 10 and 25 consecutive amino acids from SEQ ID NO: 1 including Thr34. All of the peptide fragments can be part of fusion peptides or proteins. A PP2B dephosphorylatable fragment of DARPP-32 can be prepared by any method commonly known in the art, e.g., cleaving (such as with a protease) and by phosphorylating the dephosphorylated fragment or by cleaving (such as with a protease) the phosphorylated fragment from a larger fragment of phospho-Thr34 DARPP-32 protein or from the full-length phospho-Thr34 DARPP-32 protein. Thus the fragments can be synthesized by either standard peptide synthesis disclosed below, or generated through recombinant DNA technology or by classical proteolysis.

As used herein, the term "PP2A dephosphorylatable fragment of DARPP-32" is a protein fragment of DARPP-32 that contains a threonine residue that when in the phosphorylated form can be dephosphorylated by PP2A. For human DARPP-32 having the amino acid sequence of SEQ ID NO:1, the threonine residue is preferably Thr75 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Thr75. In another embodiment of this type, the peptide fragment comprises 7 consecutive amino acids from SEQ ID NO: 1 including Thr75. In an alternative embodiment the peptide fragment comprises between 10 and 25 consecutive amino acids from SEQ ID NO: 1 including Thr75. All of the peptide fragments can be part of fusion peptides or proteins. A PP2A dephosphorylatable fragment of DARPP-32 can be prepared by any method commonly known in the art, e.g., cleaving (such as with a protease) and by phosphorylating the dephosphorylated fragment or by cleaving (such as with a protease) the phosphorylated fragment from a larger fragment of phospho-Thr75 DARPP-32 protein or from the full-length phospho-Thr75 DARPP-32 protein. Thus the fragments can be synthesized by either standard peptide synthesis disclosed below, or generated through recombinant DNA technology or by classical proteolysis.

As used herein, the amount and/or rate of phosphorylation of DARPP-32 or of a phosphorylatable fragment of DARPP-32, as described hereinabove, in a kinase reaction is "significantly changed" when the amount and/or rate of phosphorylation of DARPP-32 or the phosphorylatable fragment of DARPP-32 is increased or decreased by at least about 10-25%, relative to the control reaction. Preferably, a significant change in rate of the phosphorylation of DARPP-32 by a molecule of interest (e.g., CK1 or Cdk5) observed in the presence of a potential modulator is at some point correlated with the Michaelis constants (e.g., the Vmax or Kin) of the reaction. For example, in the case of an inhibitor, a KI can be determined. Thus, in certain embodiments, it may be preferable to study various concentrations of a modulator in a reaction mixture to allow the identification of the potential modulator as a modulator.

As used herein, the amount and/or rate of dephosphorylation of DARPP-32 or of a dephosphorylatable fragment of DARPP-32, as described hereinabove, in a phosphatase reaction is "significantly changed" when the amount and/or rate of dephosphorylation of DARPP-32 or the dephosphorylatable fragment of DARPP-32 is increased or decreased by at least about 10-25%, relative to the control reaction. Preferably, a significant change in rate of the dephosphorylation of DARPP-32 by a molecule of interest (e.g., PP2C, PP2B or PP2A) observed in the presence of a potential modulator is at some point correlated with the Michaelis constants (e.g., the Vmax or Kin) of the reaction. For example, in the case of an inhibitor, a KI can be determined. Thus, in certain embodiments, it may be preferable to study various concentrations of a modulator in a reaction mixture to allow the identification of the potential modulator as a modulator.

As used herein, the term "5-HTR-related disorder" is used interchangeably with the terms "serotonergic intracellular signaling pathway disorder," "5-HTR intracellular signaling pathway disorder," "5-HTR disorder," "5-HTR condition," "5-HTR dysfunction," "5-HTR-related dysfunction," "5-HTR-related disease," "5-HTR-related condition," "dysregulation of a 5-HTR signaling pathway," "5-HTR signaling pathway dysregulation," or analogous abbreviations. A 5-HTR-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A 5-HTR-related disorder also includes, but is not be limited to, a disease (e.g., depression) or a condition (e.g., addiction to cocaine) that involves an aberration or dysregulation of a signal transmission pathway, including, but not limited to, neurotransmission mediated by serotonergic receptors in excitable cells, tissues or organs (e.g., neurons, brain, central nervous system, etc.). A 5-HTR-related disorder also includes, but is not limited to, a symptom of a 5-HTR-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl. Acad. Sci. 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "CK1-related disorder" is used interchangeably with the terms "CK1 disorder," "CK1 condition," "CK1 dysfunction," "CK1-related dysfunction," "CK1-related disease," "CK1-related condition," "dysregulation of CK1 function" or "CK1 function dysregulation." A CK1-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A CK1-related disorder also includes, but is not limited to, a disease (e.g., depression) or a condition (e.g., addiction to cocaine) that involves an aberration or dysregulation of a signal transmission pathway, including, but not limited to, neurotransmission mediated by serotonergic receptors in excitable cells, tissues or organs (e.g., neurons, brain, central nervous system, etc.). A CK1-related disorder also includes, but is not limited to, a symptom of a CK1-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "Cdk5-related disorder" is used interchangeably with the terms "Cdk5 disorder," "Cdk5 condition," "Cdk5 dysfunction," "Cdk5-related dysfunction," "Cdk5-related disease," "Cdk5-related condition," "dysregulation of Cdk5 function" or "Cdk5 function dysregulation." A Cdk5-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A Cdk5-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). A Cdk5-related disorder also includes, but is not limited to, a symptom of a Cdk5-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "AMPA receptor-related disorder" is used interchangeably with the terms "AMPA receptor," "AMPA receptor condition," "AMPA receptor dysfunction," "AMPA receptor-related dysfunction," "AMPA receptor-related disease," "AMPA receptor-related condition," "dysregulation of AMPA receptor function" or "AMPA receptor function dysregulation." An AMPA receptor-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. An AMPA receptor-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). An AMPA receptor-related disorder also includes, but is not limited to, a symptom of an AMPA receptor-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "PP-1-related disorder" is used interchangeably with the terms "PP-1 disorder," "PP-1 condition," "PP-1 dysfunction," "PP-1-related dysfunction," "PP-1-related disease," "PP-1-related condition," "dysregulation of PP-1 function" or "PP-1 function dysregulation." A PP-1-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A PP-1-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). A PP-1-related disorder also includes, but is not limited to, a symptom of a PP-1-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "PP2C-related disorder" is used interchangeably with the terms "PP2C disorder," "PP2C condition," "PP2C dysfunction," "PP2C-related dysfunction," "PP2C-related disease," "PP2C-related condition," "dysregulation of PP2C function" or "PP2C function dysregulation." A PP2C-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A PP2C-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). A PP2C-related disorder also includes, but is not limited to, a symptom of a PP2C-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "PP2B-related disorder" is used interchangeably with the terms "PP2B disorder," "PP2B condition," "PP2B dysfunction," "PP2B-related dysfunction," "PP2B-related disease," "PP2B-related condition," "dysregulation of PP2B function" or "PP2B function dysregulation." A PP2B-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A PP2B-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). A PP2B-related disorder also includes, but is not limited to, a symptom of a PP2B-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "PP2A-related disorder" is used interchangeably with the terms "PP2A-disorder," "PP2A-condition," "PP2A-dysfunction," "PP2A-related dysfunction," "PP2A-related disease," "PP2A-related condition," "dysregulation of PP2A function" or "PP2A-function dysregulation." A PP2A-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer. A PP2A-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). A PP2A-related disorder also includes, but is not limited to, a symptom of a PP2A-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "DA-related disorder" is used interchangeably with the terms "dopamine-related disorder," "DA disorder," "dopaminergic disorder" or analogous abbreviations. A DA-related disorder includes, but is not limited to, schizophrenia, Parkinson's disease, Huntington's disease, ADD, ADHD, Tourette's syndrome, Lesch-Nyans disease, pain, dystonias and substance or drug abuse.

As used herein, a "small organic molecule" is an organic compound (or organic compound complexed with an inorganic compound (e.g., metal)) that has a molecular weight of less than 3 kilodaltons, preferably less than 1.5 kilodaltons. Preferably, the small organic molecule can cross the blood-brain barrier.

As used herein, the term "about" means within 10 to 15%, preferably within 5 to 10%. For example an amino acid sequence that contains about 60 amino acid residues can contain between 51 to 69 amino acid residues, more preferably 57 to 63 amino acid residues.

4. DESCRIPTION OF THE FIGURES

FIGS. 1(A-F). Regulation by serotonin of DARPP-32 phosphorylation in slices of neostriatum. (A-C) Time course and (D-F) dose response studies of regulation by serotonin of phosphorylation of DARPP-32 at (A and D) Thr34, (B and E) Thr75, and C and F) Sen137 in neostriatum. (A-C) Serotonin was used at 100 µM. (d f) Slices were incubated for 2 mm for studies of phospho- Thr34 DARPP-32 and phospho-Ser137 DARPP-32 and for 10 mm for studies of phospho-Thr75 DARPP-32. Data represent means (±SE) (n=6-10). *, P<0.05; , P<0.01; *, P<0.001 compared with control; one-way ANOVA followed by Dunnett's test. See Section 6 for details.

Figure 2:
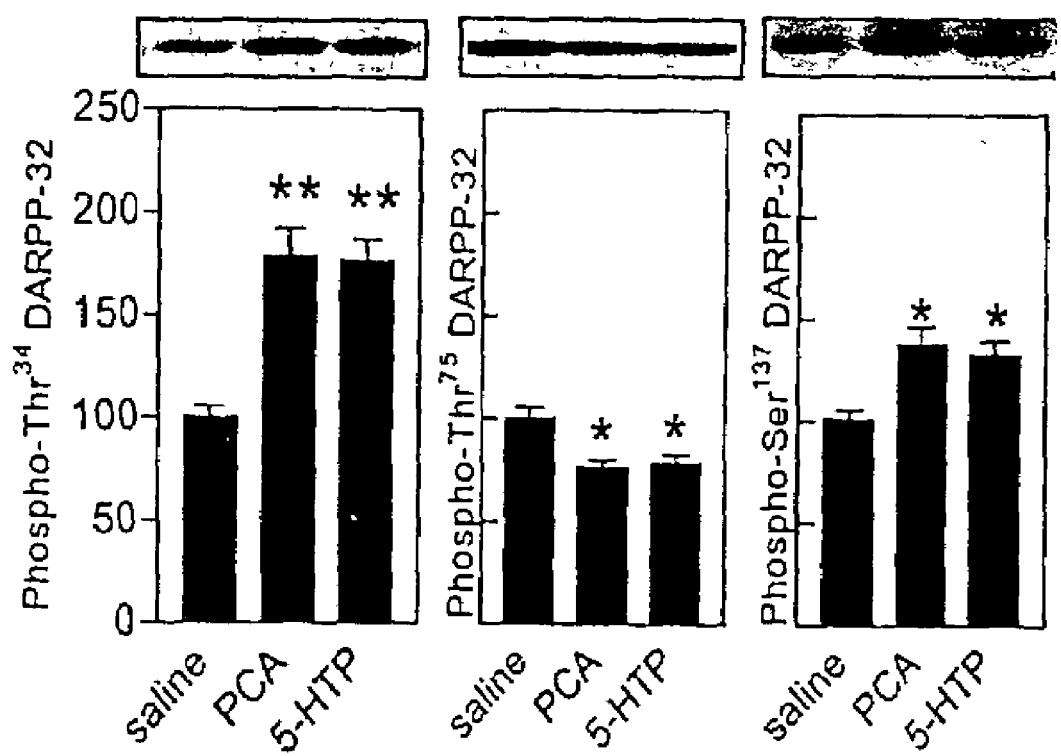

FIG. 2. Regulation of DARPP-32 phosphorylation in vivo by PCA and 5-HTP. Mice were injected i.p. with saline, PCA (4 mg/kg), or 5-HTP (50 mg/kg). Fifteen minutes later mice were killed by focused microwave irradiation. Data represent means±SE for 5-10 mice per group. *, P<0.05; , P<0.01; *, P<0.001 compared with saline-treated mice; one-way ANOVA followed by Dunnett's test. See Section 6 for details.

Figure 3:
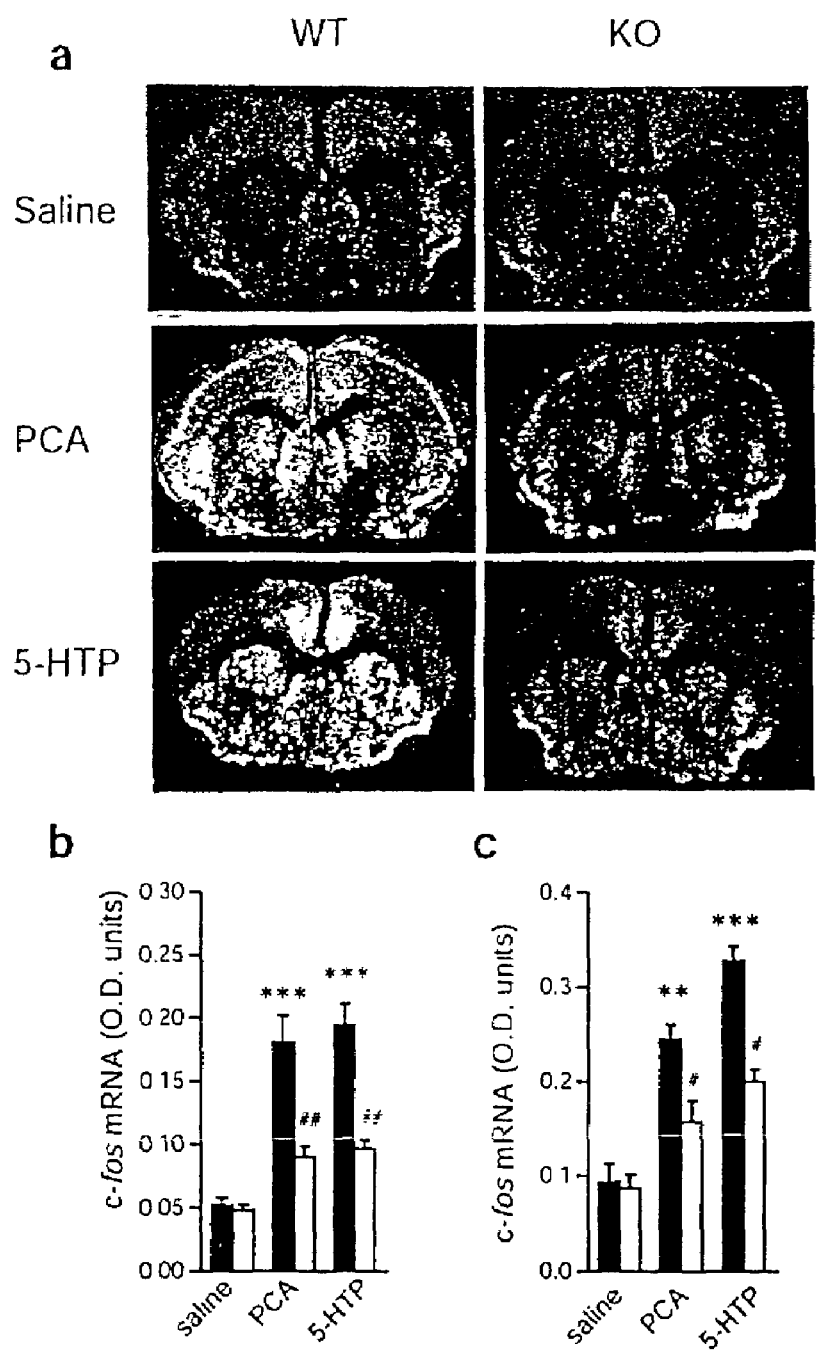

FIGS. 3(A-C). Regulation of c-fos mRNA expression by PCA and 5-HTP in WT and DARPP-32 KO mice. (A) Dark-field autoradiograms showing the expression of c-fos mRNA 20 min after treatment with saline, PCA (4 mg/kg), or 5-HTP (50 mg/kg) in WT and DARPP-32 KO mice. (Magnification: ×5) (B and C) Histograms show quantification of the expression of c-fos mRNA in (A) periventricular area of striatum and (C) cingulate cortex after each treatment. WT, filled bars; DARPP-32 KO, open bars. Data represent means±SE for 5-8 mice per group. , P<0.01; *, P<0.001 compared with saline-treated mice; #, P<0.05; ##, P<0.01 compared with WT mice given the same treatment; one-way ANOVA followed by Dunnett's test. See Section 6 for details.

Figure 4:
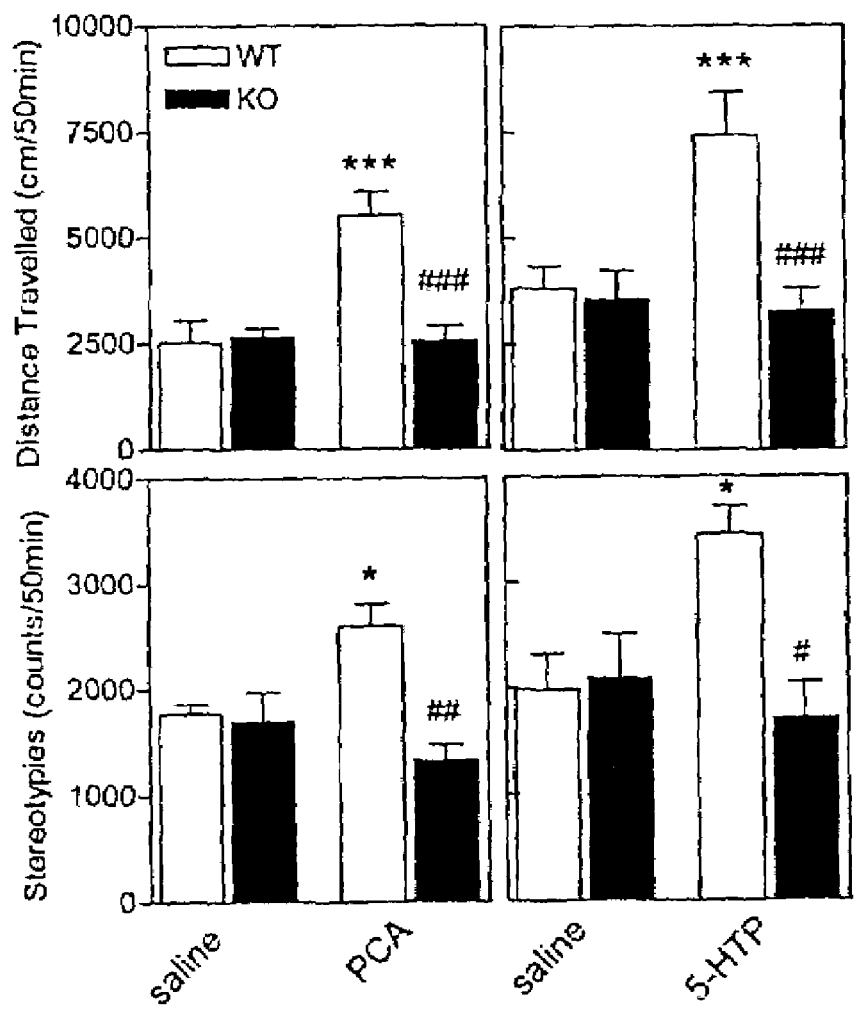

FIG. 4. Behavioral responses to treatment with PCA and 5-HTP in WT and DARPP-32 KO mice. Effects of (Left) PCA (4 mg/kg) and (Right) 5-HTP (50 mg/kg) on total locomotion (Upper) and stereotypic movements (Lower) in WT and DARPP-32 KO mice. Data represent means±SE for 6-10 mice per group. *, P<0.05; , P<0.01; *, P<0.001 compared with saline-treated mice; ###, P<0.001; ##, P<0.01; #, P<0.05 compared with WT mice given the same treatment; two-way ANOVA followed by Duncan's test. See Section 6 for details.

Figure 5:
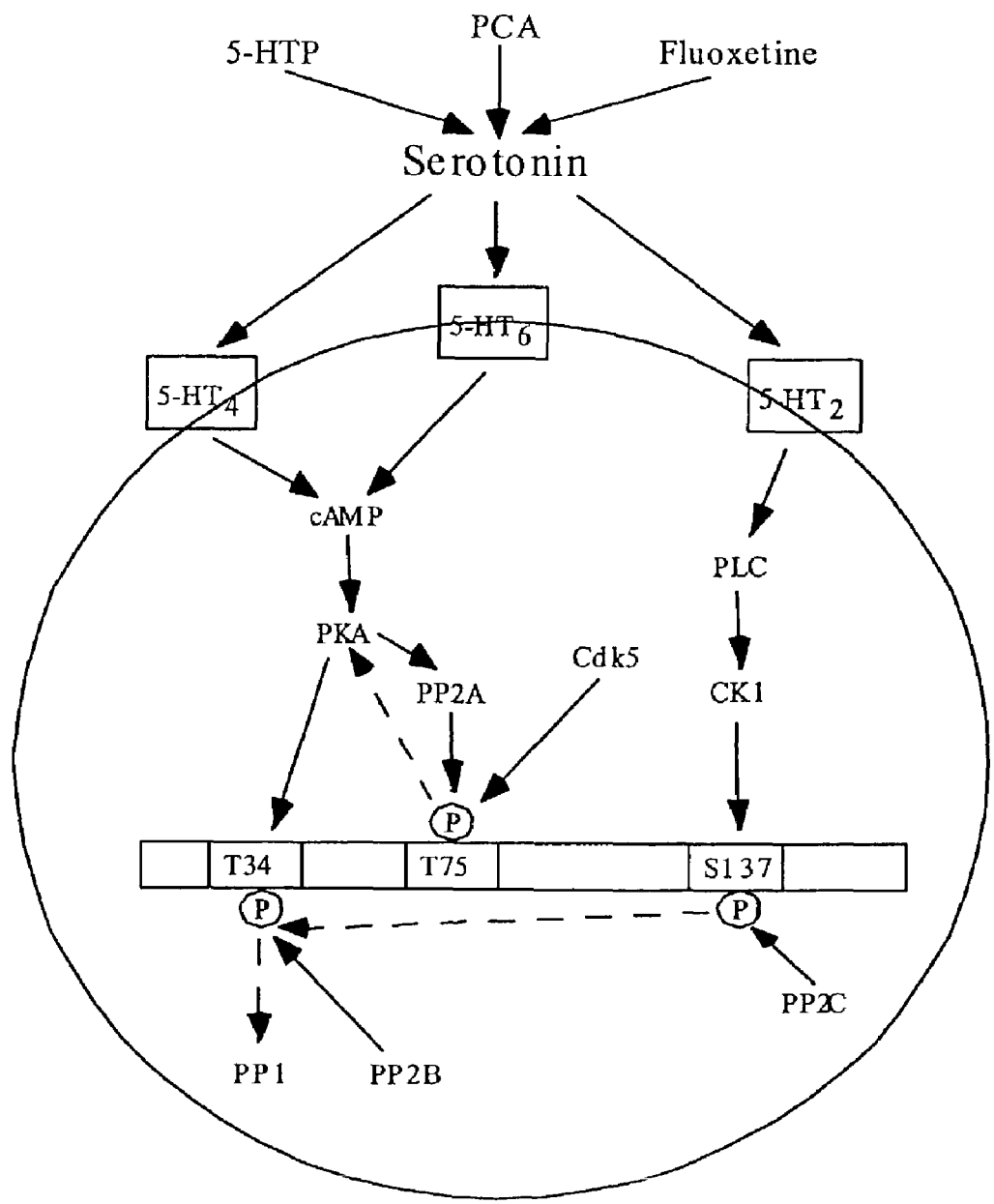

FIG. 5. Model summarizing pathways by which enhanced serotonergic transmission regulates DARPP-32 phosphorylation at Thr34, Thr75, and Ser137. Activation of 5-HT4 or 5-HT6 receptors sequentially increases cAMP levels, activity of PKA, and phosphorylation of Thr34. Activated PKA also phosphorylates and activates protein phosphatase 2A (PP-2A) (Nishi el al., 2000, Proc. Natl. Acad. Sci. USA 97, 12840-12845), causing dephosphorylation of the Cdk5 site, Thr75 (Bibb et al., 1999, Nature (London) 402, 669-671), removing inhibition of PKA (Bibb et al., 1999, Nature (London) 402, 669-671) and increasing phosphorylation of Thr34. 5-HT2 receptors activate PLC, increasing casein kinase-1 (CK1) activity (U.S. provisional application No. 60/298,978, filed on Jun. 18, 2001, which is incorporated herein by reference in its entirety), phosphorylation of Ser137, and inhibition of dephosphorylation by protein phosphatase-2B(PP2B) of Thr34 (Desdouits et al., 1995, Proc. Natl. Acad. Sci. USA 92, 2682-2685). These various actions of serotonin on DARPP-32 phosphorylation are synergistic, each leading to an increased state of phosphorylation of Thr34 and an increased inhibition of PP-1 (Hemmings, et al., 1984, Nature (London) 310, 503-505). Solid lines indicate activation; dashed lines indicate inhibition. See Section 6 for details.

Figure 6:
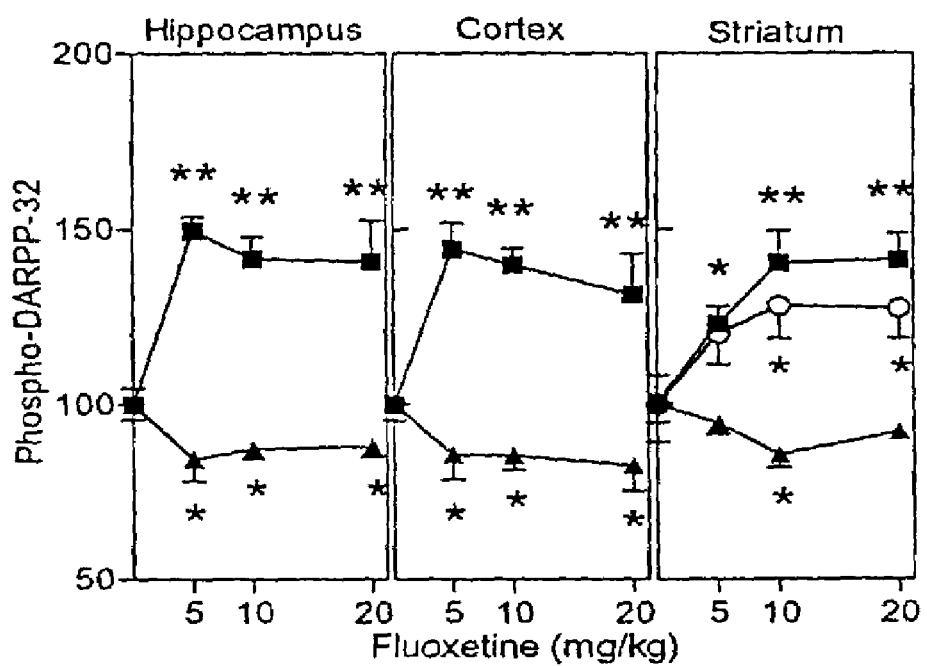

FIG. 6. Regulation of DARPP-32 phosphorylation in vivo by acute treatment with fluoxetine. Data are shown for mice treated with saline or fluoxetine (5, 10, or 20 mg/kg) and killed 15-min postinjection. The amounts of (■) phospho-Thr-34 DARPP-32 and (▲) phospho-Thr-75 DARPP-32 were quantified in hippocampus (left panel), prefrontal cortex (middle panel), and striatum (right panel), and the amounts of (○) phospho-Ser-137 DARPP-32 were quantified in striatum. Data represent means±SE for six to ten mice per group. *, P<0.05, **, P<0.01 compared with saline-treated mice, one-way ANOVA followed by Dunnett's test. See Section 7 for details.

Figure 7:
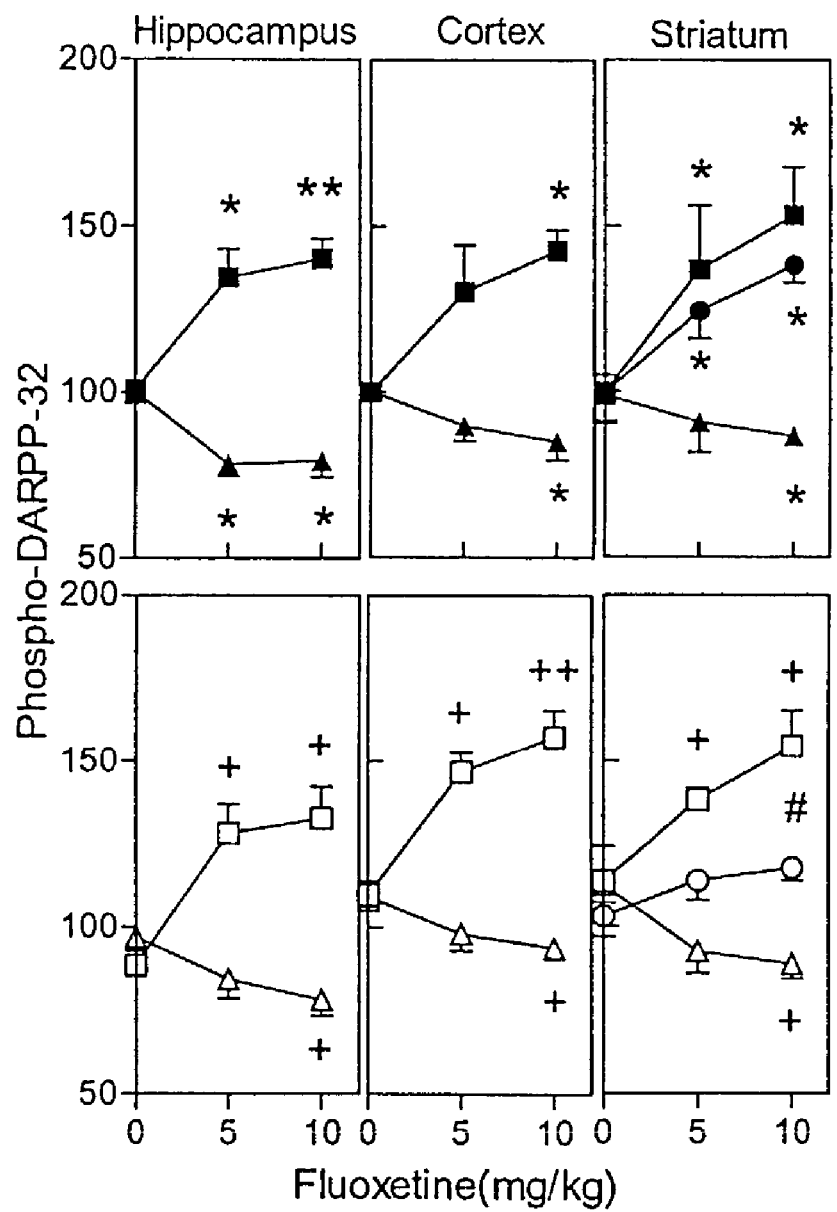

FIG. 7. Regulation of DARPP-32 phosphorylation in vivo by chronic treatment with fluoxetine. Data are shown for mice treated for 19 days with saline (Upper) or fluoxetine (10 mg/kg; Lower) and then challenged with fluoxetine (0, 5, or 10 mg/kg in saline) and killed 15-min postinjection. The amounts of (■, □) phospho-Thr-34, (▲, △) phospho-Thr-75 and (●, ○) phospho-Ser-137 DARPP-32 were quantified and normalized to total DARPP-32 (see text). Data represent means±SE for four to eight mice per group. *, P<0.05, **, P<0.01 compared with saline/saline-treated mice; #, P<0.05, P<0.01 compared with fluoxetine/saline-treated mice; #, P<0.05 compared with saline/fluoxetine-treated mice, one-way ANOVA followed by Dunnett's test. See Section 7 for details.

Figure 8:
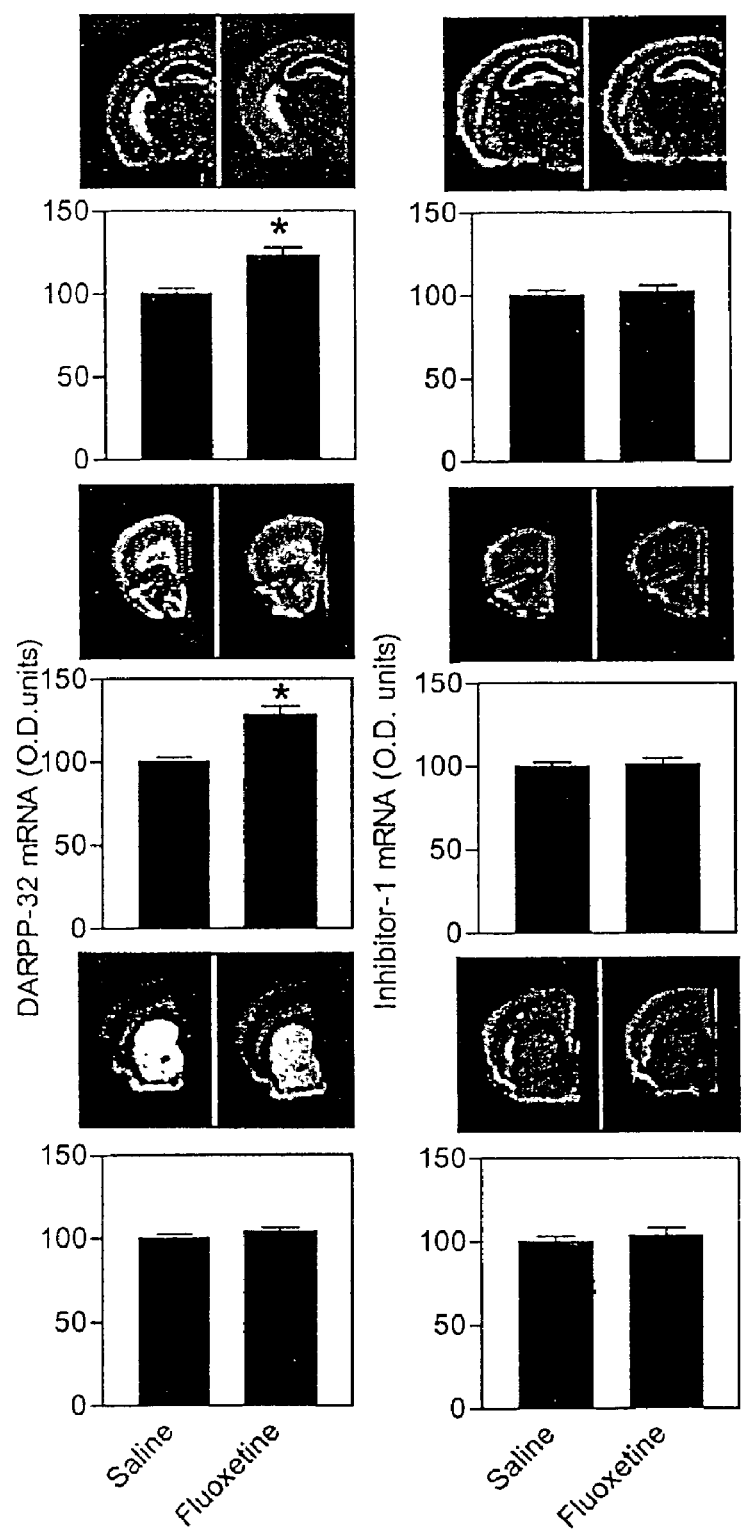

FIG. 8. Levels of DARPP-32mRNA and inhibitor-1 after chronic treatment for 19 days with saline or fluoxetine (10 mg/kg). The exposure time for the dark-field photomicrographs was 7 days, or, in the case of striatal DARPP-32 mRNA, 2 days. The amounts of DARPP-32 mRNA (Left) and inhibitor-1 mRNA (Right) were quantified by densitometry in hippocampus (Top), prefrontal cortex (Middle), and striatum (Bottom). Data represent means±SE for four to six mice per group. *, P<0.05 compared with saline-treated mice, Student's t test. See Section 7 for details.

Figure 9:
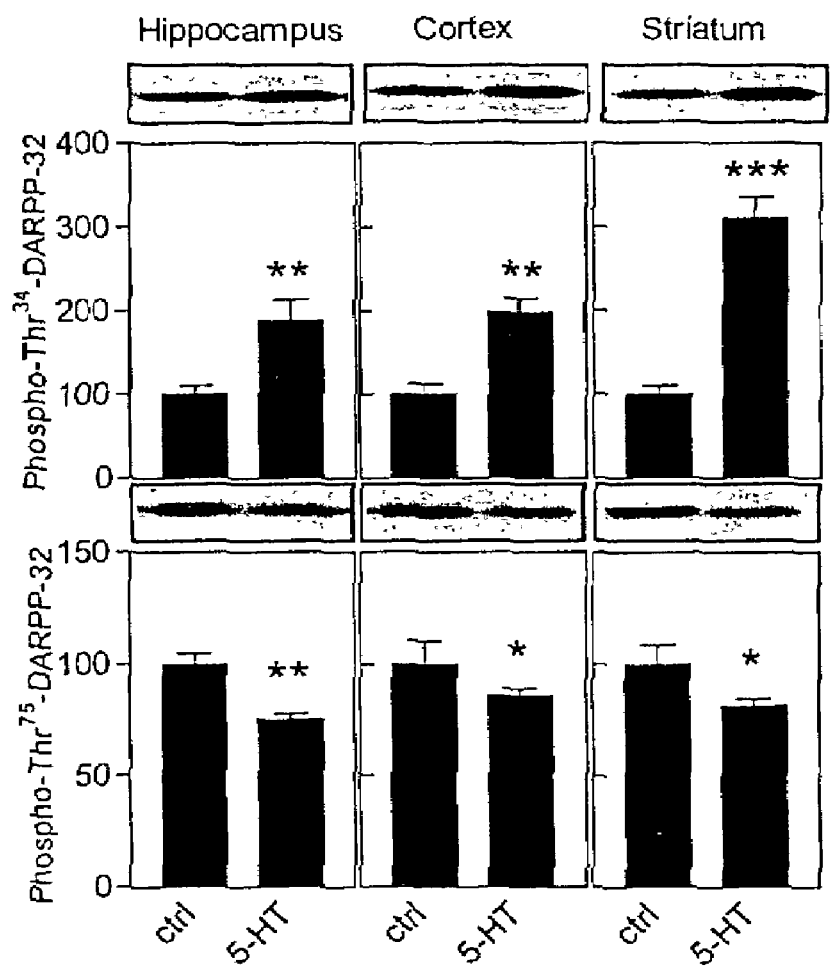

FIG. 9. Regulation of DARPP-32 phosphorylation by serotonin (100 µM) in vitro. The amounts of phospho-Thr-34 DARPP-32 (Upper) and phospho-Thr-75 DARPP-32 (Lower) in extracts of slices were quantified by densitometry. Data represent means±SE for three to ten experiments. *, P<0.05, , P<0.01, *, P<0.001 compared with control, Student's t test. See Section 7 for details.

Figure 10:
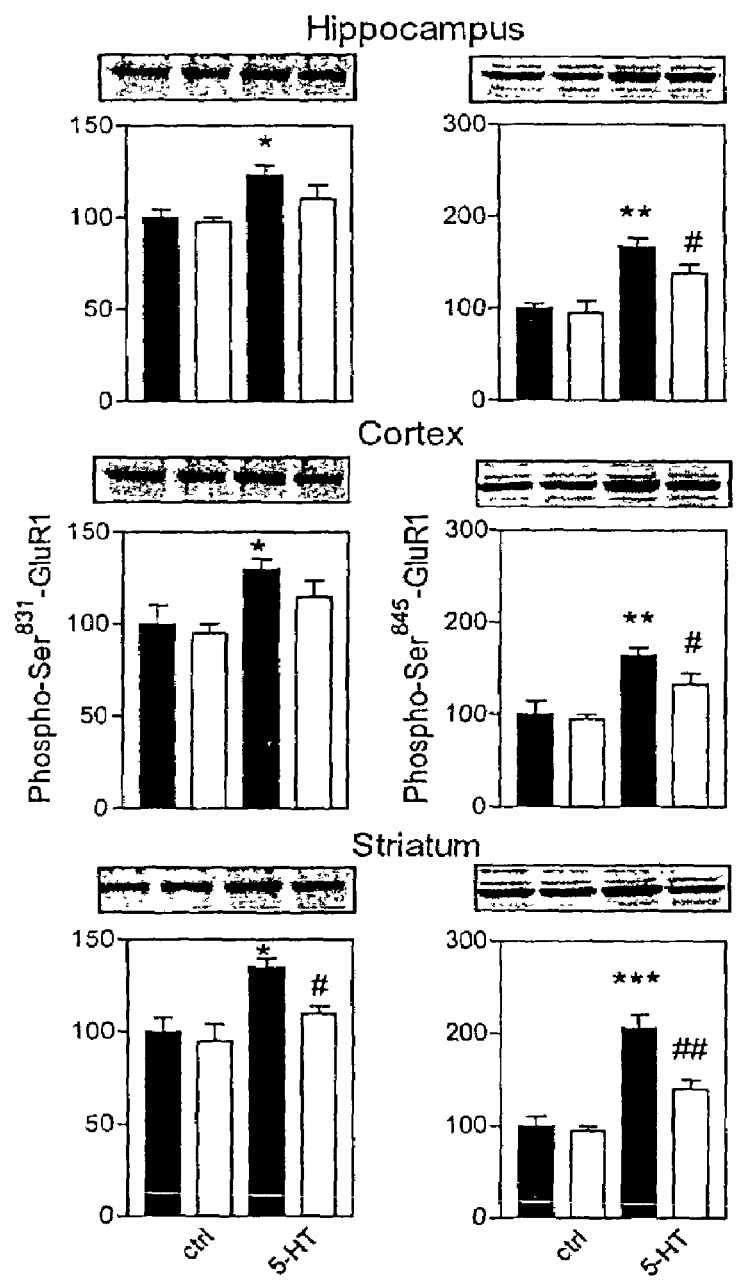

FIG. 10. Regulation of AMPA (α-amino-3-hydroxy-5-methyl-4-isoxazolepropionic acid) receptor phosphorylation by serotonin (100 µM) in vitro. The amounts of phospho-Ser-831 GluR1 (Left) and phospho-Ser-845 GluR1 (Right) in extracts of slices from WT (black bars) and DARPP-32 KO (white bars) mice were quantified by densitometry. Data represents means±SE for three to ten experiments. *, P<0.05,  P<0.01, *, P<0.001 compared with control; #, P<0.05, ##, P<0.01 compared with serotonin in WT, Student's t test. See Section 7 for details.

Figure 11:
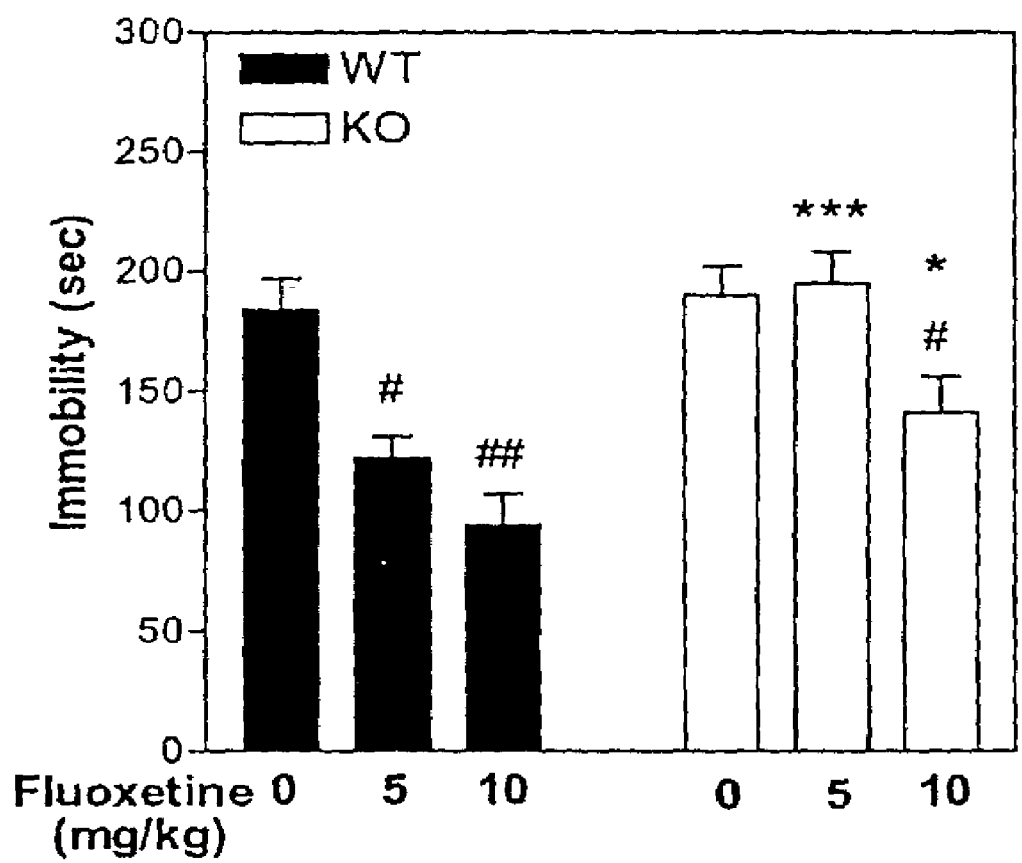

FIG. 11. Involvement of DARPP-32 in fluoxetine-mediated immobility in the tail-suspension test for antidepressant efficacy. WT and DARPP-32 KO mice were injected with fluoxetine (5 or 10 mg/kg) 30 min before the trial. The trial was conducted for a period of 5 min, during which the duration of immobility was recorded. Data represents means±SE for six to ten mice per experiment. #, P<0.05, ##, P<0.01 compared with saline; *, P<0.05, ***, P<0.001 compared with fluoxetine in DARPP-32 WT mice, two-way ANOVA followed by Duncan's test. WT, wildtype; KO, knock out. See Section 7 for details.

Figure 12:
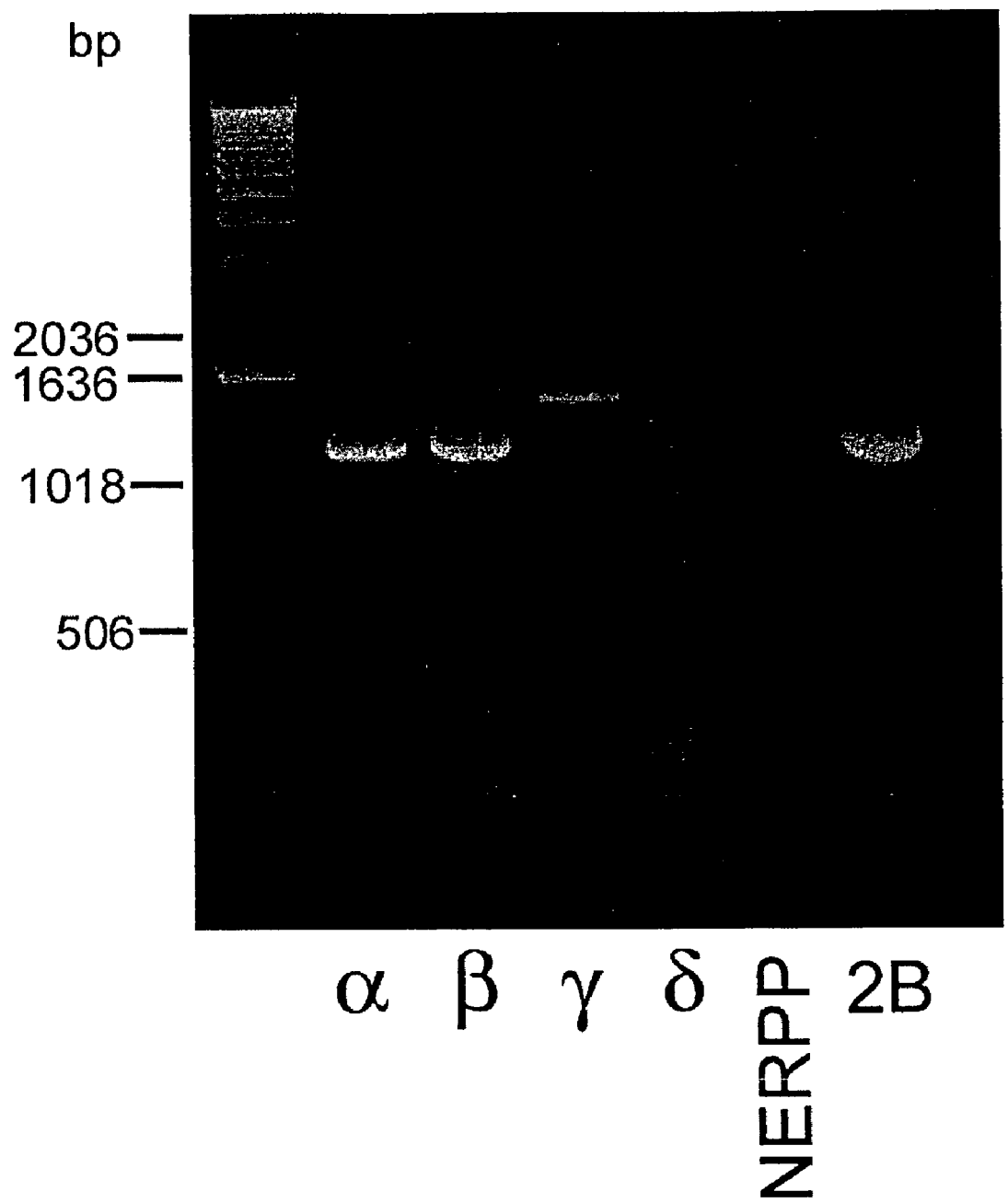

FIG. 12. PCR amplification of PP2C isoforms from rat striatum. PP2Ca (lane 1), b (lane 2), g (lane 3) and d (lane 4) were amplified by PCR from rat striatal cDNA and analyzed on a 1% agarose gel. NERPP (lane 5) and PP2B (lane 6) were used as negative and positive controls, respectively. DNA fragments were isolated from the gel and cloned into a pET28a expression vector. Lane 0, standard. See Section 8 for details.

FIGS. 13(A-B). Comparison of amino acid sequences of PP2Ca, b, g, and d isoforms cloned from rat striatum. Sequences were aligned with non-striatal isoform NERPP (Labes et al., 1998, Mol. Cell. Neurosci. 12, 29-47) A. Multiple protein sequence alignment of rat PP2C isoforms. Identical residues are shown with white letters on a black background. Conserved residues are shown in black letters with a grey background. Asterisks indicate residues that bind metal ions; triangles indicate arginine residues that interact with the phosphate moiety of substrates (Das et al., 1996, EMBO J. 15, 6798-6809). B. Schematic representation of relative similarity between different PP2C isoforms. Numbers at the left side of each protein indicate % amino acid identity between each protein and PP2Ca. Numbers associated with each individual arrow represent % amino acid identity between any two proteins. Percent identity between PP2C isoforms was calculated using the ClustalW method. See Section 8 for details.

Figure 14:
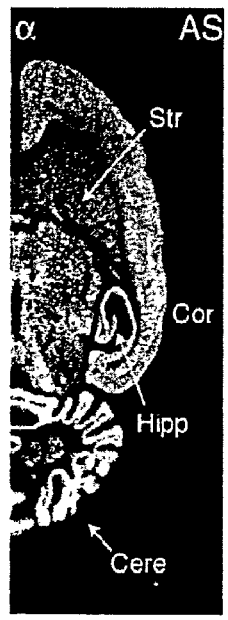
Figure 14:
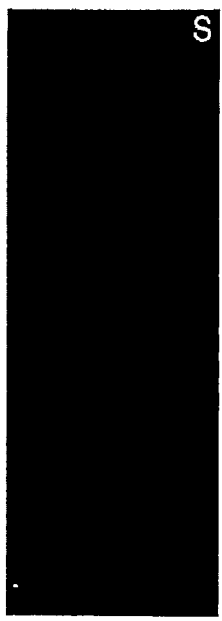
Figure 14:
Figure 14:
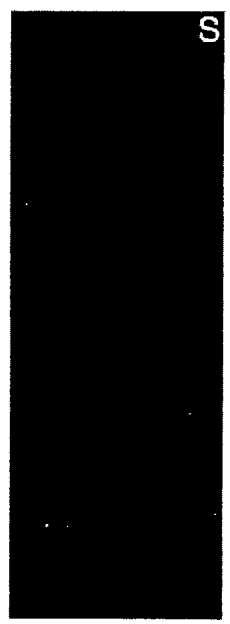
Figure 14:
Figure 14:
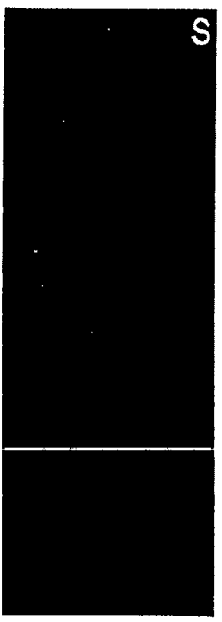
Figure 14:
Figure 14:
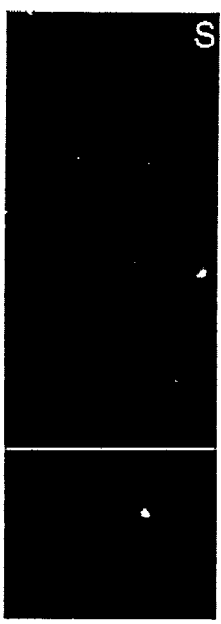

FIGS. 14(A-D). In situ hybridization of PP2C isoform in rat brain. Horizontal sections of rat brain were incubated with antisense (AS) or with sense (S) probes for PP2Ca ($\alpha$, A), b ($\beta$, B), g ($\gamma$, C) and d ($\delta$, D), as indicated. Arrows indicate brain regions with prominent expression of PP2C isoform mRNAs (Str: striatum; Hipp: hippocampus; Cere: cerebellum; Cor: cortex; Thal Ant: thalamus anterior, Thal PVN: Thalamus periventricular nucleus). See Section 8 for details.

Figure 15:
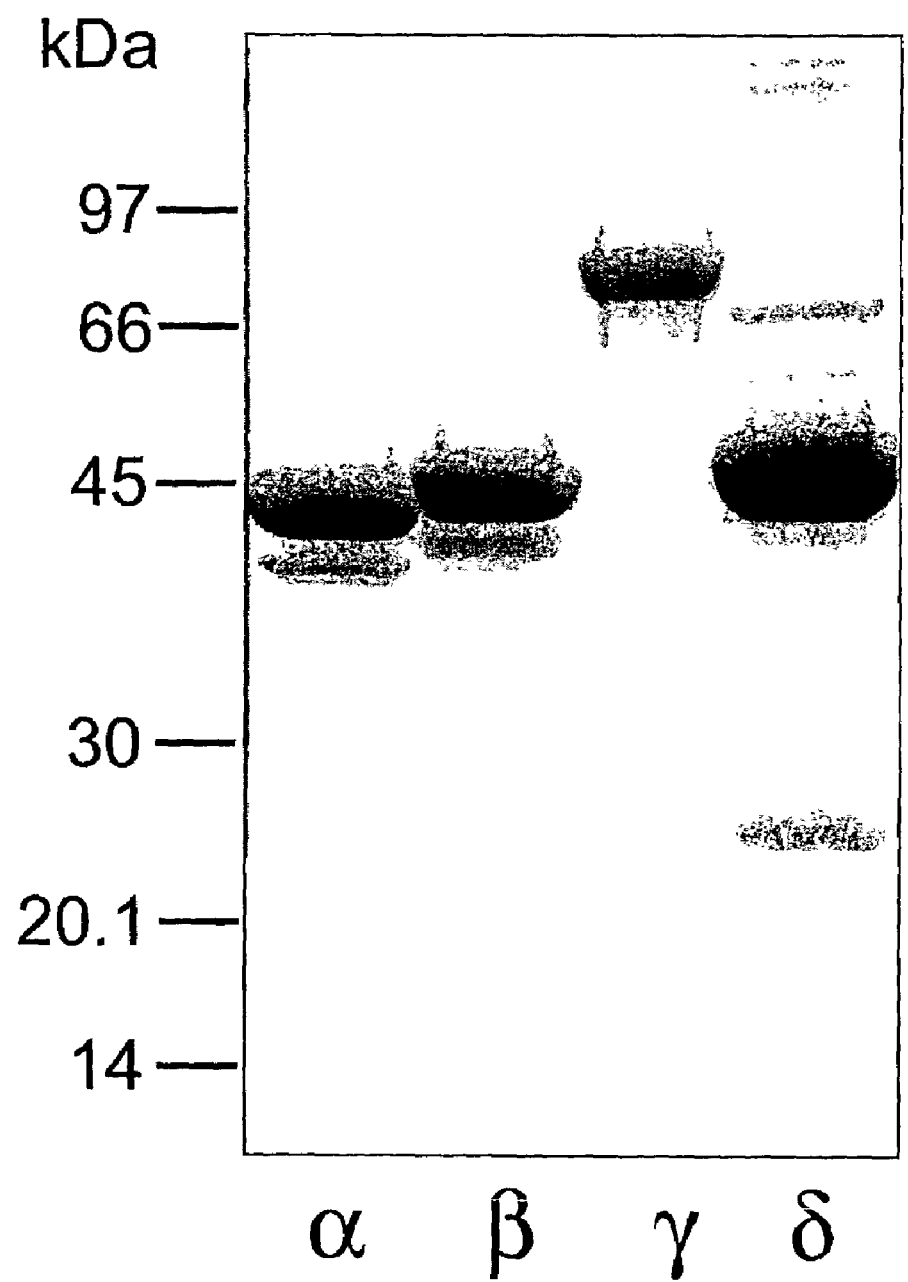

FIG. 15. Purification of recombinant PP2C isoforms from bacteria. *E. coli* cells were transformed with pET28a vectors harboring the PP2Ca, b, g and d DNAs. Protein expression was induced with IPTG and His-tagged recombinant PP2Ca, b, g and d, were purified using Ni-NTA-agarose chromatography. Aliquots (approximately 1 mg) were analyzed by SDS-PAGE and staining with Coomassie brilliant blue. PP2Ca ($\alpha$), PP2Cb ($\beta$), PP2Cg ($\gamma$), PP2Cd ($\delta$). See Section 8 for details.

Figure 16:
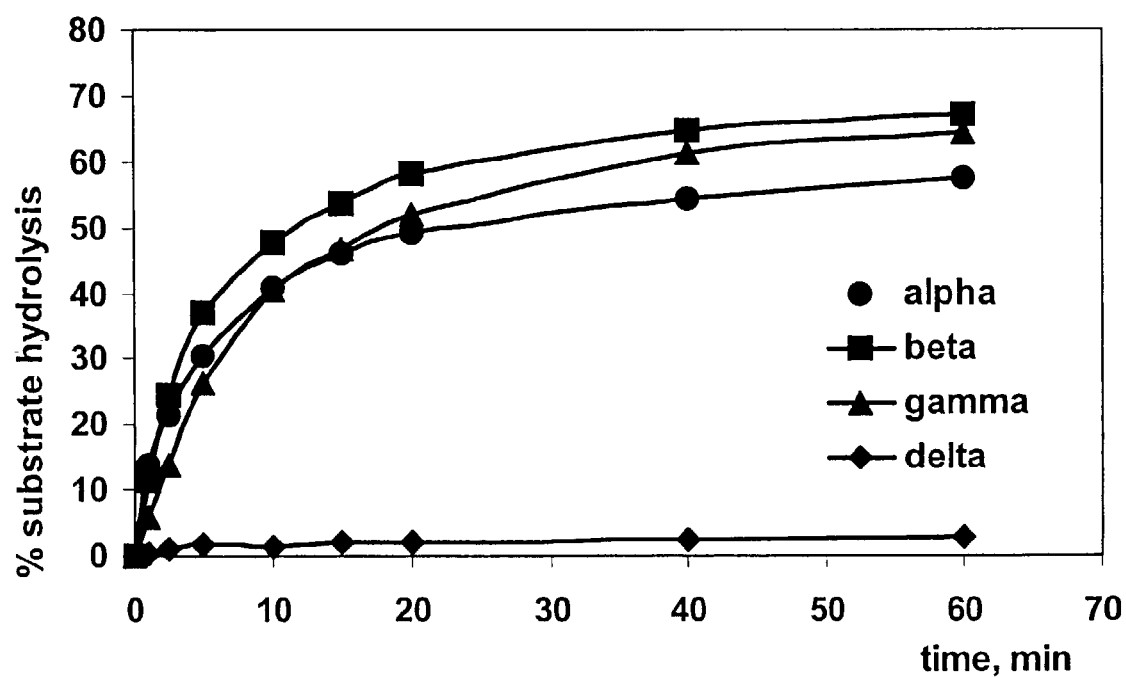

FIG. 16. Dephosphorylation of phospho-Ser137-DARPP-32 by PP2C isoforms. DARPP-32 phosphorylated at Ser137 by CK1 was incubated with PP2Ca, b, g and d isoforms for various times as indicated. Assays were carried out in the presence of 10 mM $Mn^{2+}$ at 37° C. See Section 8 for details.

FIGS. 17(A-C). Effect of metal ions on activity of PP2C isoforms. PP2Ca, b, and g were assayed at 37° C. using [$^{32}$P]phospho-Ser137-DARPP32 as substrate in the absence or presence of various concentrations of $Mg^{2+}$ (filled circle) or $Mn^{2+}$ (filled square). PP2Ca ($\alpha$), PP2Cb ($\beta$), PP2Cg ($\gamma$). See Section 8 for details.

Figure 18:
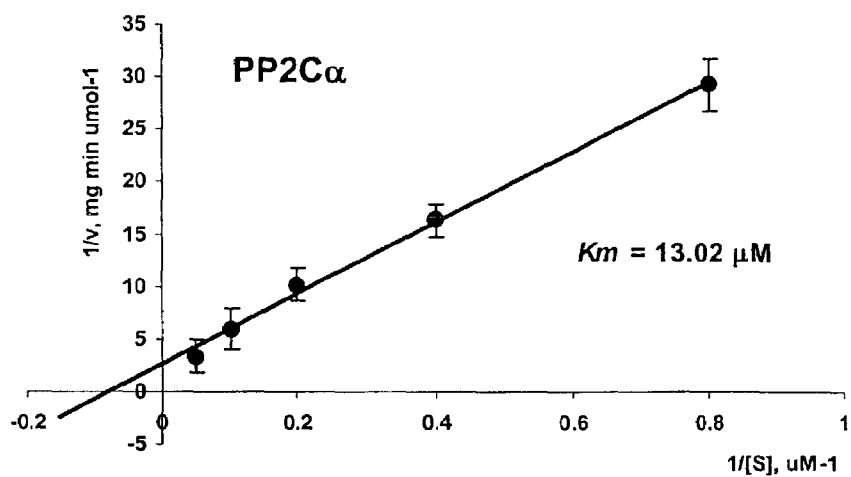
Figure 18:
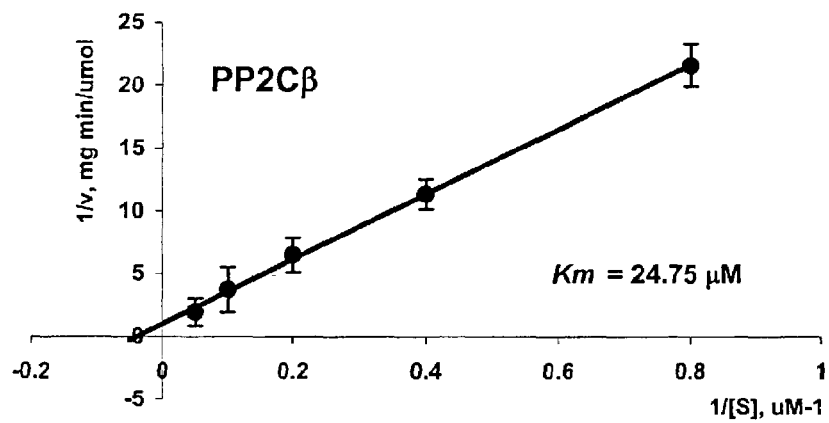
Figure 18:
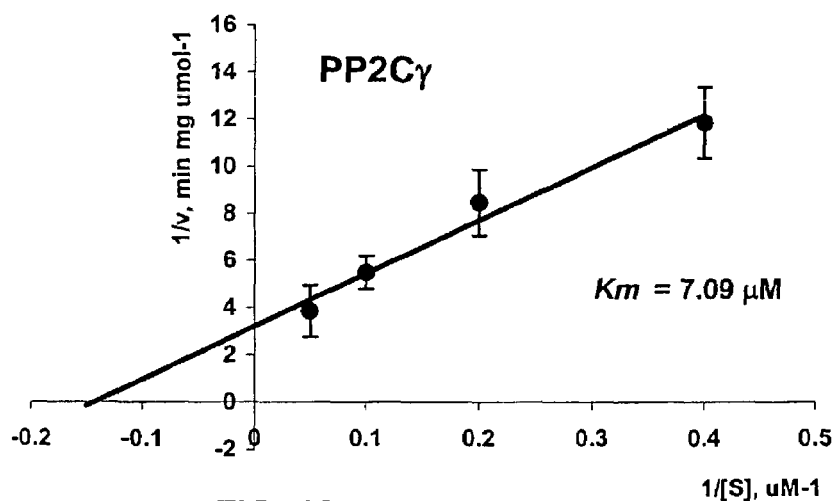

FIGS. 18(A-C). Kinetic analysis of dephosphorylation of phospho-Ser137-DARPP 32 by PP2C isoforms. PP2Ca, b, and g were assayed at 37° C. using [$^{32}$P]phospho-Ser137-DARPP32 as substrate in the presence of 20 mM $Mn^{2+}$. Various concentrations of substrate from 0.125 to 20 mM, were used as indicated. Data from three independent experiments were analyzed and plotted using the Lineweaver-Burk method. PP2Ca ($\alpha$), PP2Cb ($\beta$), PP2Cg ($\gamma$). See Section 8 for details.

5. DETAILED DESCRIPTION OF THE INVENTION

The present invention is based on the surprising discovery, on the part of the inventors, that serotonin increases the phosphorylation of DARPP-32 at the Thr34 and Ser137 sites and decreases phosphorylation at Thr75. Since according to the invention, serotonin mimics the activity of other substances that modulate DARPP-32 phosphorylation, such as activators of CK1, inhibitors of cdk5, inhibitors of PP-1, inhibitors of PP2C, inhibitors of PP2B, or activators of PP2A, and since serotonergic intracellular signaling pathways are involved in the etiology of depression, according to the methods of the invention, compounds that alter activity of serotonergic intracellular signaling molecules, including, but not limited to CK1 (e.g., CK1$\alpha$, CK1$\beta$, CK1$\gamma$i, CK1$\gamma$2, CK1$\gamma$3, CK1$\delta$, CK1 $\epsilon$), Cdk5, AMPA receptor, PP-1, PP2C (including, but not limited to, PP2Ca, PP2Cb and PP2Cg), PP2B and/or PP2A, have antidepressant activity.

Serotonin (5-HT) per se and agents that enhance serotonergic neurotransmission act on cell-surface receptors. According to the invention, 5-HT2, 5-HT4 and 5-HT6 receptors mediate the phosphorylation of DARPP-32 via serotonergic intracellular signaling pathways. According to the invention, serotonin, via binding to 5-HT4 and 5-HT6 receptors, increases the formation of cAMP and the activation of protein kinase A (PKA). PKA, in turn, phosphorylates DARPP-32 at Thr34. This phosphorylation event converts DARPP-32 into an inhibitor of protein phosphatase-1 (PP-1). PKA also activates PP2A, which subsequently dephosphorylates DARPP-32 at Thr75. The phosphorylation state at this site is normally kept at a relatively high level by Cdk5 and by doing so, makes DARPP-32 an inhibitor of PKA. Thus, according to the invention, by activating a PKA/PP2A intracellular signaling pathway and dephosphorylation of Thr75-DARPP-32, serotonin decreases a constitutive inhibition of PKA. This action of serotonin serves as a positive feedback loop for the PKA-mediated regulation of DARPP-32 at Thr34. Further according to the invention, inhibition of PP-1 by phosphorylated DARPP-32 inhibits the PP-1 mediated dephosphorylation of the phospho-Ser845 of the GluR1 subunit of the AMPA (AMPA, $\alpha$-amino-3-hydroxy-5-methyl-4-isoxazolepropionic acid) receptor. This, in turn, leads to increased phosphorylation of Ser845 of the GluR1 subunit and activates the AMPA receptor.

According to the invention, serotonin, via 5-HT2 receptors, increases PLC formation and activates CK-1. CK-1, in turn, phosphorylates DARPP-32 at Ser137. This phosphorylation event converts DARPP-32 into an inhibitor of PP2B (i.e., calcineurin). Since PP2B dephosphorylates DARPP-32 at Thr34, the serotonin-mediated increase in DARPP-32 phosphorylation at Ser 137 potentiates the serotonin/PKA-mediated phosphorylation at Thr34-DARPP-32 and the subsequent inhibition of PP-1. Further according to the invention, the phosphorylation state of Ser137-DARPP-32 can be modulated by modulation of PP2C via a serotonergic intracellular signaling pathway. In one embodiment, the phosphorylation of Ser137-DARPP-32 increases via a decrease in the activity, e.g., inhibition, of PP2C.

The present invention provides a method for modulating casein kinase 1 ("CK1" or "CK1"), cyclin-dependent kinase 5 ("Cdk5," "cdk5" or "CDK5"), protein phosphatase 1 ("PP-1), AMPA receptor ("AMPA"), protein phosphatase-2C ("PP2C"), protein phosphatase-2B ("PP2B") or protein phosphatase-2A ("PP2A") activity in a cell or tissue of interest, comprising contacting the cell or tissue of interest with an effective amount of a compound that alters the activity of a serotonergic receptor (5-HTR) intracellular signaling molecule, wherein contact of the cell or tissue with the compound results in a modulation of the activity of CK1, Cdk5, AMPA receptor, PP-1, PP2C, PP2B and/or PP2A.

The present invention provides a method for modulating activity of AMPA receptors comprising administering (for example, to an individual, patient or animal) an effective amount of a compound of the invention, for example, a compound identified by the methods of the invention, wherein the compound modulates the activity of CK1, Cdk5, PP-1, PP2C, PP2B and/or PP2A and wherein modulation of CK1, Cdk5, PP-1, PP2C, PP2B and/or PP2A activity results in an alteration in the activity of AMPA receptors in the neuron. In a specific embodiment, AMPA receptors are in an excitable cell, e.g., a neuron. In another embodiment, the method involves administration of a 5-HTR agonist or antagonist in order to modulate activity of CK1, Cdk5, PP-1, PP2C, PP2B and/or PP2A and thereby alter activity of the AMPA receptors.

The present invention provides, in vivo, in situ, and in vitro, methods of identifying an agent, drug or compound for modulating the activity of CK1, Cdk5, AMPA receptor, PP-1, PP2C, PP2B and/or PP2A in a cell or tissue of interest. Such methods can be used alone or in conjunction with each other. In one embodiment, the method comprises determining a first level of CK1, Cdk5, AMPA receptor, PP-1, PP2C, PP2B and/or PP2A activity in a cell or tissue of interest; contacting the cell or tissue with a test compound; and determining a second level of CK1, Cdk5, AMPA receptor, PP-1, PP2C, PP2B and/or PP2A activity in the cell or tissue, wherein a difference in the first level and the second level of CK1, Cdk5, AMPA receptor, PP-1, PP2C, PP2B and/or PP2A activity is indicative of the ability of the test compound to modulate CK1, Cdk5, AMPA receptor, PP-1, PP2C, PP2B and/or PP2A activity.

In another embodiment, the method comprises determining a first level of CK1, Cdk5, PP-1, PP2C, PP2B and/or PP2A activity in a cell or tissue of interest; determining a first level of AMPA receptor activity in the cell or tissue; contacting the cell or tissue with a test compound; determining a second level of CK1, Cdk5, PP-1, PP2C, PP2B and/or PP2A activity in the cell or tissue; and determining a second level of AMPA receptor activity in the cell or tissue, wherein a difference in the first level and the second level of CK1, Cdk5, PP-1, PP2C, PP2B and/or PP2A activity, respectively and a difference in the first level and the second level of AMPA receptor activity are indicative of the ability of the test compound to modulate the activity of AMPA receptors.

In another embodiment, the invention provides a method for treating a 5-HT-related or DA-related disorder in a patient in need thereof comprising administering to the patient an agent that increases the phosphorylation of Thr34-phosphorylated DARPP-32 or Ser137-phosphorylated DARPP-32, or that decreases the phosphorylation of Thr75-phosphorylated DARPP-32, wherein the agent increases the activity of a serotonergic intracellular signaling pathway molecule.

The present invention also provides in vivo methods of identifying agents that can modulate the activity of an serotonergic intracellular signaling pathway via modulation of CK1, Cdk5, AMPA receptor, PP-1, PP2C, PP2B and/or PP2A activity. Such methods can be employed alone or in conjunction with in vitro and in situ methods as disclosed herein. One such method comprises administering the agent to a non-human mammal. The amount (and/or rate) of activation of CK1, Cdk5, AMPA receptor, PP-1, PP2C, PP2B and/or PP2A is then determined. An agent is identified as capable of modulating the activity of a serotonergic intracellular signaling pathway via modulation of CK1, Cdk5, AMPA receptor, PP-1, PP2C, PP2B and/or PP2A when the amount (and/or rate) of activation is increased or decreased in the presence of the agent relative to in the absence of the agent. In preferred embodiments, the non-human mammal is a rodent. In a more preferred embodiment, the rodent is a mouse.

The invention also provides methods of screening potential agents (or drugs or compounds) in order to select an agent that can potentially ameliorate and/or be used in treatment of a 5-HTR-related disorder, a DA-related disorder, a CK1-related disorder, a Cdk5-related disorder, a AMPA-receptor-related disorder, or a PP-1-, PP2C-, PP2B- and/or PP2A-related disorder.

The present invention also provides methods of identifying agents (or drugs or compounds), e.g., drug screening assays, which drugs may be used in therapeutic methods for the treatment of a 5-HTR-related disorder, a DA-related disorder, a CK1-related disorder, a Cdk5-related disorder, a AMPA-receptor-related disorder, or a PP-1-, PP2C-, PP2B- and/or PP2A-related disorder. In a specific embodiment, the method comprises detecting the increase (or decrease) in the amount of phosphorylation (or dephosphorylation) of Thr34-phosphorylated DARPP-32, Ser137-phosphorylated DARPP-32, or Thr75-phosphorylated DARPP-32.

In another embodiment, the invention provides a method for treating a 5-HT-related or DA-related disorder in a patient in need thereof comprising administering to the patient an agent that alters the phosphorylation of phosphorylated DARPP-32, wherein the agent modulates the activity of CK1, Cdk5, AMPA receptor, PP-1, PP2C, PP2B and/or PP2A.

In another embodiment, the invention provides a method for identifying an agent for use in the treatment of a 5-HT-related or DA-related disorder in a patient in need of such treatment comprising: (a) contacting a potential agent with Cdk5 and Thr75-dephosphorylated DARPP-32; and (b) detecting the amount of phosphorylation of Thr75-dephosphorylated DARPP-32; wherein the agent is identified if a decrease in the phosphorylation of Thr75-dephosphorylated DARPP-32 is detected in the presence of the potential agent.

In another embodiment, the invention provides a method for treating a 5-HT-related or DA-related disorder in a patient in need thereof comprising administering to the patient an agent that decreases the dephosphorylation of Thr34-phosphorylated DARPP-32, wherein the agent decreases PP-1 activity.

In another embodiment, the invention provides a method for identifying an agent for use in the treatment of 5-HT-related or DA-related disorder in a patient in need of such treatment comprising: (a) contacting a potential agent with PP-1 and Thr34-phosphorylated DARPP-32; and (b) detecting the amount of dephosphorylation of Thr34-phosphorylated DARPP-32; wherein the agent is identified if a decrease in the dephosphorylation of Thr34-phosphorylated DARPP-32 is detected in the presence of the potential agent.

In another embodiment, the invention provides a method for treating a 5-HT-related disorder or DA-related in a patient in need thereof comprising administering to the patient an agent that decreases the dephosphorylation of Ser137-phosphorylated DARPP-32, wherein the agent decreases PP2C activity.

In another embodiment, the invention provides a method for identifying an agent for use in the treatment of 5-HT-related or DA-related disorder in a patient in need of such treatment comprising: (a) contacting a potential agent with PP2C and Ser137-phosphorylated DARPP-32; and (b) detecting the amount of dephosphorylation of Ser137-phosphorylated DARPP-32; wherein the agent is identified if an decrease in the dephosphorylation of Ser137-phosphorylated DARPP-32 is detected in the presence of the potential agent.

In another embodiment, the invention provides a method for treating a 5-HT-related or DA-related disorder in a patient in need thereof comprising administering to the patient an agent that inhibits the dephosphorylation of Thr34-phosphorylated DARPP-32, wherein the agent decreases PP2B activity.

In another embodiment, the invention provides a method for identifying an agent for use in the treatment of 5-HT-related disorder or DA-related in a patient in need of such treatment comprising: (a) contacting a potential agent with PP2B and Thr34-phosphorylated DARPP-32; and (b) detecting the amount of dephosphorylation of Thr34-phosphorylated DARPP-32; wherein the agent is identified if a decrease in the dephosphorylation of Thr34-phosphorylated DARPP-32 is detected in the presence of the potential agent.

In another embodiment, the invention provides a method for treating a 5-HT-related or DA-related disorder in a patient in need thereof comprising administering to the patient an agent that increase the dephosphorylation of Thr75-phosphorylated DARPP-32, wherein the agent increases PP2A activity.

In another embodiment, the invention provides a method for identifying an agent for use in the treatment of 5-HT-related or DA-related disorder in a patient in need of such treatment comprising: (a) contacting a potential agent with PP2A and Thr75-phosphorylated DARPP-32; and (b) detecting the amount of dephosphorylation of Thr75-phosphorylated DARPP-32; wherein the agent is identified if an increase in the dephosphorylation of Thr75-phosphorylated DARPP-32 is detected in the presence of the potential agent.

In another embodiment, the invention provides a method for regulating phosphorylation-dependent activation of AMPA receptors in a cell comprising administering an effective amount of a compound that modulates activity of CK1, Cdk5, PP-1, PP2C, PP2B and/or PP2A, wherein modulation of the activity of CK1, Cdk5, PP-1, PP2C, PP2B and/or PP2A results in an alteration in the phosphorylation-dependent activation of AMPA receptors in the cell.

The present invention also provides compositions for modulating the activity of CK1, Cdk5, AMPA receptor, PP-1, PP2C, PP2B and/or PP2A.

The present invention further provides methods for performing rational drug design to develop drugs that can modulate activity of CK1, Cdk5, AMPA receptor, PP-1, PP2C, PP2B and/or PP2A and thereby ameliorate a 5-HTR-related disorder, a CK1-related disorder, a Cdk5-related disorder, a AMPA-receptor-related disorder, or a PP-1-, PP2C-, PP2B- and/or PP2A-related disorder.

In one embodiment, the invention provides methods of identifying a compound that modulates the activity of casein kinase 1 in a cell or tissue of interest comprising: (a) determining a first level of casein kinase 1 activity in said cell or tissue; (b) contacting said cell or tissue with a test compound; and (c) determining a second level of casein kinase 1 activity in said cell or tissue, wherein a difference in said first level and said second level of casein kinase 1 activity is indicative of the ability of said test compound to modulate casein kinase 1 activity, and wherein modulation of casein kinase 1 activity is regulated by modulation of the activity of a 5-HTR intracellular signaling pathway.

In one embodiment, the invention provides methods of identifying a compound that modulates the activity of cyclin-dependent kinase 5 in a cell or tissue of interest comprising: (a) determining a first level of cyclin-dependent kinase 5 activity in said cell or tissue; (b) contacting said cell or tissue with a test compound; and (c) determining a second level of cyclin-dependent kinase 5 activity in said cell or tissue, wherein a difference in said first level and said second level of cyclin-dependent kinase 5 activity is indicative of the ability of said test compound to modulate cyclin-dependent kinase 5 activity, and wherein modulation of cyclin-dependent kinase 5 activity is regulated by modulation of the activity of a 5-HTR intracellular signaling pathway.

In one embodiment, the invention provides methods of identifying a compound that modulates the activity of AMPA receptors in a cell or tissue of interest comprising: (a) determining a first level of AMPA receptor activity in said cell or tissue; (b) contacting said cell or tissue with a test compound; and (c) determining a second level of AMPA receptor activity in said cell or tissue, wherein a difference in said first level and said second level of AMPA receptor activity is indicative of the ability of said test compound to modulate AMPA receptor activity, and wherein modulation of AMPA receptor activity is regulated by modulation of the activity of a 5-HTR intracellular signaling pathway.

In one embodiment, the invention provides methods of identifying a compound that modulates the activity of PP-1 in a cell or tissue of interest comprising: (a) determining a first level of PP-1 activity in said cell or tissue; (b) contacting said cell or tissue with a test compound; and (c) determining a second level of PP-1 activity in said cell or tissue, wherein a difference in said first level and said second level of PP-1 activity is indicative of the ability of said test compound to modulate PP-1 activity, and wherein modulation of PP-1 activity is regulated by modulation of the activity of a 5-HTR intracellular signaling pathway.

In one embodiment, the invention provides methods of identifying a compound that modulates the activity of PP2C in a cell or tissue of interest comprising: (a) determining a first level of PP2C activity in said cell or tissue; (b) contacting said cell or tissue with a test compound; and (c) determining a second level of PP2C activity in said cell or tissue, wherein a difference in said first level and said second level of PP2C activity is indicative of the ability of said test compound to modulate PP2C activity, and wherein modulation of PP2C activity is regulated by modulation of the activity of a 5-HTR intracellular signaling pathway.

In one embodiment, the invention provides methods of identifying a compound that modulates the activity of PP2B in a cell or tissue of interest comprising: (a) determining a first level of PP2B activity in said cell or tissue; (b) contacting said cell or tissue with a test compound; and (c)

determining a second level of PP2B activity in said cell or tissue, wherein a difference in said first level and said second level of PP2B activity is indicative of the ability of said test compound to modulate PP2B activity, and wherein modulation of PP2B activity is regulated by modulation of the activity of a 5-HTR intracellular signaling pathway.

In one embodiment, the invention provides methods of identifying a compound that modulates the activity of PP2A in a cell or tissue of interest comprising: (a) determining a first level of PP2A activity in said cell or tissue; (b) contacting said cell or tissue with a test compound; and (c) determining a second level of PP2A activity in said cell or tissue, wherein a difference in said first level and said second level of PP2A activity is indicative of the ability of said test compound to modulate PP2A activity, and wherein modulation of PP2A activity is regulated by modulation of the activity of a 5-HTR intracellular signaling pathway.

The present invention also provides diagnostic and therapeutic methods for the treatment of a 5-HTR-related disorder, a CK1-related disorder, a Cdk5-related disorder, a AMPA-receptor-related disorder, or a PP-1-, PP2C-, PP2B- and/or PP2A-related disorder, including, but not limited the use of compositions or compounds of the invention in the treatment of a 5-HTR-related disorder, a CK1-related disorder, a Cdk5-related disorder, a AMPA-receptor-related disorder, or a PP-1-, PP2C-, PP2B- and/or PP2A-related disorder.

In one aspect, the invention provides a method for treating a neuronal condition characterized by modulation of a serotonergic intracellular signaling pathway comprising administering to a subject in need of such treatment an effective amount of a compound of the present invention to modulate CK1, Cdk5, AMPA receptor, PP-1, PP2C, PP2B and/or PP2A activity, and thus increase or decrease AMPA receptor activity and/or the activity of a DA intracellular signaling pathway via modulation of a 5-HTR intracellular signaling pathway.

In certain embodiments, the 5-HTR intracellular signaling pathway comprises: (i) activation of 5-HT4 and 5-HT6 receptors, which increases cAMP activation of PKA phosphorylation of Thr-34; (ii) activation of 5-HT4 and 5-HT6 receptors, which increases cAMP activation of PKA activation of protein phosphatase-2A (PP-2A) dephosphorylation of Thr-75; and/or (iii) activation of 5-HT2 receptors, which increases activation of PLC, which in turn increases calcium activation of CK1 dependent phosphorylation of Ser-137.

Thus any compound identified according to the methods of the invention that affects these interactions may also serve as the basis of a therapeutic treatment for a 5-HTR-related disorder, and therefore, all of the proteins that participate in such interactions may also be used in assays as described herein.

The present invention provides methods for treating a 5-HTR-related disorder, a CK1-related disorder, a Cdk5-related disorder, a AMPA-receptor-related disorder, or a PP-1-, PP2C-, PP2B- and/or PP2A-related disorder in an individual (e.g., a patient) or an animal subject by administering an effective amount of a compound of the invention to modulate CK1, Cdk5, AMPA receptor, PP-1, PP2C, PP2B and/or PP2A activity. In one embodiment, the agent promotes or increases the activity of CK1, Cdk5, AMPA receptor, PP-1, PP2C, PP2B and/or PP2A. In another embodiment, the agent inhibits or decreases the activity of CK1, Cdk5, AMPA receptor, PP-1, PP2C, PP2B and/or PP2A.

In certain embodiments, the invention provides a method for treating a 5-HT-related disorder in a patient in need thereof comprising administering to the patient an agent that modulates the phosphorylation of DARPP-32 at Thr34, Thr75 and/or Ser137, wherein the agent modulates the activity of CK1, Cdk5, AMPA receptor, PP-1, PP2C, PP2B and/or PP2A. In specific embodiments, the agent modulates the activity by binding to CK1, Cuk5, AMPA receptor, PP-1, PP2C, PP2B and/or PP2A.

The invention provides methods of administering an agent (or drug or compound) of the invention that can ameliorate a symptom of a 5-HTR-related disorder, a CK1-related disorder, a Cdk5-related disorder, a AMPA-receptor-related disorder, or a PP-1-, PP2C-, PP2B- and/or PP2A-related disorder, disease and/or condition in a patient or subject exhibiting the symptom. In certain embodiments, the invention provides methods of administering an agent identified by the methods disclosed herein, that can ameliorate a symptom of a 5-HTR-related disorder, a CK1-related disorder, a Cdk5-related disorder, a AMPA-receptor-related disorder, or a PP-1-, PP2C-, PP2B- and/or PP2A-related disorder in a patient or subject exhibiting the symptom. In other embodiments, an agonist of 5-HTR activity can be used to for treating a 5-HTR-related disorder, a CK1-related disorder, a Cdk5-related disorder, a AMPA-receptor-related disorder, or a PP-1-, PP2C-, PP2B- and/or PP2A-related disorder. In yet other embodiments, an antagonist of 5-HTR activity can be used to for treating a 5-HTR-related disorder, a CK1-related disorder, a Cdk5-related disorder, a AMPA-receptor-related disorder, or a PP-1-, PP2C-, PP2B- and/or PP2A-related disorder.

The present invention also provides compositions for modulating the activity of CK1, Cdk5, AMPA receptor, PP-1, PP2C, PP2B and/or PP2A. The invention also provides compositions for modulating the activity of AMPA receptors via modulation of the activity of CK1, Cdk5, AMPA receptor, PP-1, PP2C, PP2B and/or PP2A. The present invention also provides pharmaceutical compositions of the agents (or drugs or compounds) of the invention disclosed herein. The invention encompasses pharmaceutical compositions for regulating CK1, Cdk5, AMPA receptor, PP-1, PP2C, PP2B and/or PP2A activity, and for diagnosing or treating a 5-HTR-related disorder, a CK1-related disorder, a Cdk5-related disorder, a AMPA-receptor-related disorder, or a PP-1-, PP2C-, PP2B- and/or PP2A-related disorder. Because in certain embodiments, a decrease of normal function can produce the development of a phenotype of the above-listed diseases or disorders (e.g., depression), activation of a serotonergic receptor (5-HTR) signaling pathway, or an increase in CK1, Cdk5, AMPA receptor, PP-1, PP2C, PP2B and/or PP2A (e.g., downstream activation) facilitates amelioration of a symptom in individuals exhibiting a symptom of such a disorder (e.g., depression).

The present invention also provides compositions for modulating the activity of a dopaminergic intracellular signaling pathway by modulating a serotonergic intracellular signaling pathway. The present invention also provides pharmaceutical compositions of the agents (or drugs or compounds) of the invention disclosed herein. The invention encompasses pharmaceutical compositions for modulating the activity of a dopaminergic intracellular signaling pathway by modulating a serotonergic intracellular signaling pathway, and for diagnosing or treating a DA-related disorder. Because in certain embodiments, a decrease of normal dopaminergic function can produce the development of a phenotype of a DA-related disorder (e.g., Parkinson's disease), activation of DARPP-32 via a serotonergic intracellular signaling pathway, or by modulating the activity of CK1, Cdk5, AMPA receptor, PP-1, PP2C, PP2B and/or PP2A, can facilitate amelioration of a symptom in individuals exhibiting a symptom of DA-related disorder that is independent of enhanced dopaminergic neurotransmission. Thus according to the invention, agents that enhance serotonergic neurotransmission or the activity of a serotonergic intracellular signaling pathway, or that modulate the activity of CK1, Cdk5, AMPA receptor, PP-1, PP2C, PP2B and/or PP2A, can thus exert ameliorative effects independent of dopamine, and can be used in the treatment of DA-related disorders.

For clarity of disclosure, and not by way of limitation, the detailed description of the invention is divided into the subsections set forth below.

5.1. Methods for Modulating the Activity of CK1, CDK5, AMPA Receptor, PP-1, PP2C, PP2B and/or PP2A The present invention provides a method for modulating CK1, Cdk5, AMPA receptor, PP-1, PP2C, PP2B and/or PP2A activity in a cell or tissue of interest comprising contacting the cell or tissue of interest with an effective amount of a compound that alters the activity of a serotonergic receptor (5-HTR) intracellular signaling molecule, wherein contact of the cell or tissue with the compound results in a modulation of the activity of CK1, Cdk5, AMPA receptor, PP-1, PP2C, PP2B and/or PP2A. A cell or tissue may include, but not be limited to: an excitable cell, e.g., a sensory neuron, motorneuron, or interneuron; a glial cell; a primary culture of neuronal or glial cells; cell(s) derived from a neuronal or glial cell line; dissociated cell(s); whole cell(s); permeabilized cell(s); a cellular extract or purified enzyme preparation; and a tissue or organ, e.g., brain, brain slice, spinal cord, spinal cord slice, central nervous system, peripheral nervous system, or nerve. In a specific embodiment, the activity of CK1, Cdk5, AMPA receptor, PP-1, PP2C, PP2B and/or PP2A is increased. In another specific embodiment, the activity of CK1, Cdk5, AMPA receptor, PP-1, PP2C, PP2B and/or PP2A is decreased.

In one embodiment, the invention provides methods of modulating the activity of casein kinase 1 (CK1), cyclin-dependent kinase 5 (Cdk5), protein phosphatase 2C (PP2C), protein phosphatase 2B (PP2B) and/or protein phosphatase 2A (PP2A) via the modulation of the activity of serotonergic receptors (5HTRs). In a preferred embodiment, the serotonergic receptor is a 5-HT2, 5-HT4 or 5-HT6 serotonergic receptor. in another embodiment, the invention provides methods of modulating the activity of AMPA receptors via modulation of the activity of CK1, Cdk5, PP-1, PP2C, PP2B and/or PP2A.

In one embodiment, a method is provided for modulating CK1, Cdk5, AMPA receptor, PP-1, PP2C, PP2B and/or PP2A activity in cells or tissues of interest in vitro. In another embodiment, CK1, Cdk5, AMPA receptor, PP-1, PP2C, PP2B and/or PP2A activity in cells or tissues of interest is modulated in vivo. The in vitro and in vivo applications may include, but are not limited to modulating activity in whole animals, in tissue slices, in broken cell preparations, in intact cells, and in isolated and purified cell preparations.

According to the present invention, the compounds of the invention may be 5-HTR agonists or antagonists. In other embodiments, however, they may be compounds that act at levels of the 5-HTR intracellular signaling pathway other than at the level of the serotonergic receptor. As a result, the present invention also includes, in certain embodiments, compositions identified by screening for compounds that act at levels of the 5-HTR intracellular signaling pathway other than at the level of the serotonergic receptor. One of skill would understand that once identified as capable of modulating CK1, Cdk5, AMPA receptor, PP-1, PP2C, PP2B and/or PP2A activity in the methods of the present invention, the compound may be used therapeutically to modulate CK1, Cdk5, AMPA receptor, PP-1, PP2C, PP2B and/or PP2A activity in cells, e.g., neurons, in order to treat conditions in which CK1, Cdk5, AMPA receptor, PP-1, PP2C, PP2B and/or PP2A activity may be involved. Such conditions include, but are not limited to, a 5-HTR-related disorder, a CK1-related disorder, a Cdk5-related disorder, a AMPA-receptor-related disorder, or a PP-1-, PP2C-, PP2B- and/or PP2A-related disorder The present invention provides a method for modulating the activity of AMPA receptors comprising administering (for example, to an individual, patient or animal) an effective amount of a compound, for example, a compound identified by the methods of the invention, wherein modulation of CK1, Cdk5, PP-1, PP2C, PP2B and/or PP2A activity results in an alteration in the activity of AMPA receptors in a cell. In one embodiment, the AMPA receptors are in an excitable cell, e.g., a neuron. In another embodiment, the method involves administration of a 5-HTR agonist in order to increase activity of CK1, Cdk5, PP-1, PP2C, PP2B and/or PP2A and thereby alter activity of the AMPA receptors.

Without wishing to be bound by any particular theory, in one aspect of the invention, activation of 5-HT2, 5-HT-4 or 5-HT6 receptors by an agonist, e.g., 5-HTP, PCA or fluoexetine, mediates the phosphorylation of DARPP-32 via serotonergic intracellular signaling pathways. According to the invention, serotonin, via binding to 5-HT4 and 5-HT6 receptors, increases the formation of cAMP and the activation of protein kinase A (PKA). PKA, in turn, phosphorylates DARPP-32 at Thr34. This phosphorylation event converts DARPP-32 into an inhibitor of protein phosphatase-1 (PP-1). PKA also activates PP2A, which subsequently dephosphorylates DARPP-32 at Thr75. The phosphorylation state at this site is normally kept at a relatively high level by Cdk5 and by doing so, makes DARPP-32 an inhibitor of PKA. Thus, according to the invention, by activating a PKA/PP2A intracellular signaling pathway and dephosphorylation of Thr75-DARPP-32, serotonin decreases a constitutive inhibition of PKA. This action of serotonin serves as a positive feedback loop for the PKA-mediated regulation of DARPP-32 at Thr34. Further according to the invention, inhibition of PP-1 by phosphorylated DARPP-32 inhibits the PP-1 mediated dephosphorylation of the phospho-Ser845 of the GluR1 subunit of the AMPA (AMPA, α-amino-3-hydroxy-5-methyl-4-isoxazolepropionic acid) receptor. This, in turn, leads to increased phosphorylation of Ser845 of the GluR1 subunit and activates the AMPA receptor.

According to the invention, serotonin, via 5-HT2 receptors, increases PLC formation and activates CK-1. CK-1, in turn, phosphorylates DARPP-32 at Ser137. This phosphorylation event converts DARPP-32 into an inhibitor of PP2B (i.e., calcineurin). Since PP2B dephosphorylates DARPP-32 at Thr34, the serotonin-mediated increase in DARPP-32 phosphorylation at Ser 137 potentiates the serotonin/PKA-mediated phosphorylation at Thr34-DARPP-32 and the subsequent inhibition of PP-1. Further according to the invention, the phosphorylation state of Ser137-DARPP-32 is modulated by activation of PP2C via a serotonergic intracellular signaling pathway.

Without wishing to be bound by any particular theory, in another aspect of the invention, activation of 5-HT4 receptors by an agonist, e.g., 5-HTP, PCA or fluoexetine, increases cAMP activation of PKA phosphorylation of Thr-34 and increases cAMP activation of PKA activation of PP-2A dephosphorylation of Thr-75.

Without wishing to be bound by any particular theory, in another aspect of the invention, activation of 5-HT6 receptors by an agonist, e.g., 5-HTP, PCA or fluoexetine, increases cAMP activation of PKA phosphorylation of Thr-34 and increases cAMP activation of PKA activation of PP-2A dephosphorylation of Thr-75.

Without wishing to be bound by any particular theory, in another aspect of the invention, activation of 5-HT2 receptors by an agonist, e.g., 5-HTP, PCA or fluoexetine, increases activation of PLC, which in turn increases calcium activation of CK1 dependent phosphorylation of Ser-137.

5.2. Methods for Screening for Compounds that Modulate the Activity of CK1, CDK5, AMPA Receptor, PP-1, PP2C, PP2B and/or PP2A The present invention provides methods of identifying an agent (or drug or compound) that modulates the activity of CK1, Cdk5, AMPA receptor, PP-1, PP2C, PP2B and/or PP2A in a cell or tissue of interest. In one embodiment, the invention provides methods of identifying an agent that modulates the activity of CK1, Cdk5, AMPA receptor, PP-1, PP2C, PP2B and/or PP2A via the modulation of the activity of serotonergic receptors. In specific embodiments, the agent modulates the activity by binding to CK1, Cdk5, AMPA receptor, PP-1, PP2C, PP2B and/or PP2A.

According to the invention, a cell or tissue of interest may include, but not be limited to: an excitable cell, e.g., a sensory neuron, motorneuron, or interneuron; a glial cell; a primary culture of neuronal or glial cells; cell(s) derived from a neuronal or glial cell line; dissociated cell(s); whole cell(s); permeabilized cell(s); a cellular extract or purified enzyme preparation; and a tissue or organ, e.g., brain, brain slice, spinal cord, spinal cord slice, central nervous system, peripheral nervous system, or nerve.

In another embodiment, the invention provides methods of identifying an agent that modulates the activity of CK1, Cdk5, AMPA receptor, PP-1, PP2C, PP2B and/or PP2A via the modulation of a serotonergic intracellular signaling pathway. In another embodiment, the invention provides methods of identifying an agent that modulates the activity of a serotonergic intracellular signaling pathway via modulation of the activity of CK1, Cdk5, AMPA receptor, PP-1, PP2C, PP2B and/or PP2A. In specific embodiments, the agent modulates the activity by binding to CK1, Cdk5, AMPA receptor, PP-1, PP2C, PP2B and/or PP2A.

In specific embodiments of the invention, a serotonergic (5HT) receptor is a 5-HT2, 5-HT4 and/or 5-HT6 receptor.

In another embodiment, the invention provides methods of identifying an agent that modulates the activity of AMPA receptors via modulation of the activity of CK1, Cdk5, PP-1, PP2C, PP2B and/or PP2A.

In certain embodiments, activity of CK1, Cdk5, AMPA receptor, PP-1, PP2C, PP2B and/or PP2A encompasses expression of CK1, Cdk5, AMPA receptor, PP-1, PP2C, PP2B and/or PP2A, respectively. Expression may be measured by any method commonly known in the art.

As would be clearly understood by a person of ordinary skill in the art, any and/or all of the embodiments disclosed herein for identifying an agent, drug or compound that can modulate the activity of a 5-HT receptor, CK1, Cdk5, AMPA receptor, PP-1, PP2C, PP2B and/or PP2A, including such procedures that incorporate rational drug design, as disclosed herein, can be combined to form additional drug screens and assays, all of which are contemplated by the present invention.

In one embodiment, the method comprises determining a first level of CK1, Cdk5, AMPA receptor, PP-1, PP2C, PP2B and/or PP2A activity in a cell or tissue of interest; contacting the cell or tissue with a test compound; and determining a second level of CK1, Cdk5, AMPA receptor, PP-1, PP2C, PP2B and/or PP2A activity in the cell or tissue, wherein a difference in the first level and the second level of CK1, Cdk5, AMPA receptor, PP-1, PP2C, PP2B and/or PP2A activity is indicative of the ability of the test compound to modulate CK1, Cdk5, AMPA receptor, PP-1, PP2C, PP2B and/or PP2A activity.

In another embodiment, the method comprises determining a first level of CK1, Cdk5, AMPA receptor, PP-1, PP2C, PP2B and/or PP2A activity in a cell or tissue of interest; determining a first level of AMPA receptor activity in the cell or tissue; contacting the cell or tissue with a test compound; determining a second level of CK1, Cdk5, AMPA receptor, PP-1, PP2C, PP2B and/or PP2A activity in the cell or tissue; and determining a second level of AMPA receptor activity in the cell or tissue, wherein a difference in the first level and the second level of CK1, Cdk5, AMPA receptor, PP-1, PP2C, PP2B and/or PP2A activity and a difference in the first level and the second level of AMPA receptor activity are indicative of the ability of the test compound to modulate the activity of AMPA receptors.

In another embodiment, the invention provides a method of identifying a compound that modulates the activity of CK1, Cdk5, AMPA receptor, PP-1, PP2C, PP2B and/or PP2A in a cell or tissue of interest comprising: (a) determining a first level of CK1, Cdk5, AMPA receptor, PP-1, PP2C, PP2B and/or PP2A activity in said cell or tissue; (b) contacting said cell or tissue with a test compound; and (c) determining a second level of CK1, Cdk5, AMPA receptor, PP-1, PP2C, PP2B and/or PP2A activity in said cell or tissue, wherein a difference in said first level and said second level of CK1, Cdk5, AMPA receptor, PP-1, PP2C, PP2B and/or PP2A activity is indicative of the ability of said test compound to modulate CK1, Cdk5, AMPA receptor, PP-1, PP2C, PP2B and/or PP2A activity, and wherein modulation of CK1, Cdk5, AMPA receptor, PP-1, PP2C, PP2B and/or PP2A activity is regulated by modulation of a serotonergic intracellular signaling pathway and/or the activity of 5-HT receptors.

In another embodiment, the invention provides a method for identifying a compound to be tested for its ability to modulate the activity of a dopaminergic intracellular signaling pathway in a cell or tissue of interest comprising: (a) determining a first level of CK1, Cdk5, AMPA receptor, PP-1, PP2C, PP2B and/or PP2A activity in said cell or tissue; (b) contacting said cell or tissue with a test compound; and (c) determining a second level of CK1, Cdk5, AMPA receptor, PP-1, PP2C, PP2B and/or PP2A activity, respectively, in said cell or tissue, wherein a difference in said first level and said second level of CK1, Cdk5, AMPA receptor, PP-1, PP2C, PP2B and/or PP2A activity is indicative of the ability of said test compound to modulate the dopaminergic intracellular signaling pathway. In certain embodiments, the method comprises the additional step of determining whether the dopaminergic intracellular signaling pathway is modulated. In yet another embodiment, the invention provides a method for treating a DA-related disorder in a patient in need thereof comprising administering to the patient an agent that increases the activity of a serotonergic intracellular signaling pathway.

In yet other embodiments, the invention provides a method for treating a 5HTR-related disorder in a patient in need thereof comprising administering to the patient an agent that increases the activity of a dopaminergic intracellular signaling pathway.

In another embodiment, the invention provides a method of identifying a compound to be tested for its ability to modulate the activity of a serotonergic intracellular signaling pathway in a cell or tissue of interest comprising: (a) determining a first level of CK1, Cdk5, AMPA receptor, PP-1, PP2C, PP2B and/or PP2A activity in said cell or tissue; (b) contacting said cell or tissue with a test compound; and (c) determining a second level of CK1, Cdk5, AMPA receptor, PP-1, PP2C, PP2B and/or PP2A activity, respectively, in said cell or tissue, wherein a difference in said first level and said second level of CK1, Cdk5, AMPA receptor, PP-1, PP2C, PP2B and/or PP2A activity is indicative of the ability of said test compound to modulate the serotonergic intracellular signaling pathway. In certain embodiment, the method comprises the additional step of determining whether the serotonergic intracellular signaling pathway is modulated.

In a preferred embodiment, activity of a serotonergic intracellular signaling pathway is regulated by modulation of the activity of 5-HT2, 5-HT4 or 5-HT6 receptors.

In another embodiment, the invention provides a method of identifying a compound that modulates the activity of CK1, Cdk5, AMPA receptor, PP-1, PP2C, PP2B and/or PP2A in a cell or tissue of interest comprising contacting said cell or tissue with a test compound, determining a level of CK1, Cdk5, AMPA receptor, PP-1, PP2C, PP2B and/or PP2A activity in said cell or tissue, wherein a difference in said level and a standard or baseline level of CK1, Cdk5, AMPA receptor, PP-1, PP2C, PP2B and/or PP2A activity in a comparable cell or tissue not contacted with the test compound is indicative of the ability of said test compound to modulate CK1, Cdk5, AMPA receptor, PP-1, PP2C, PP2B and/or PP2A activity, and wherein modulation of CK1, Cdk5, AMPA receptor, PP-1, PP2C, PP2B and/or PP2A activity is regulated by modulation of a serotonergic intracellular signaling pathway and/or the activity of 5-HT receptors.

In another embodiment, the invention provides a method of identifying a compound for modulating phosphorylation-dependent activation of AMPA receptors in a cell or tissue of interest comprising:
  (a) determining a first level of CK1, Cdk5, PP-1, PP2C, PP2B and/or PP2A activity in a cell or tissue of interest;
  (b) determining a first level of phosphorylation-dependent activation of AMPA receptors in the cell or tissue;
  (c) contacting the cell or tissue with a test compound;
  (d) determining a second level of CK1, Cdk5, PP-1, PP2C, PP2B and/or PP2A activity, respectively, in the cell or tissue; and
  (e) determining a second level of phosphorylation-dependent activation of AMPA receptors in the cell or tissue, wherein a difference in the first level and the second level of CK1, Cdk5, PP-1, PP2C, PP2B and/or PP2A activity and a difference in the first level and the second level of phosphorylation-dependent activation of AMPA receptors are indicative of the ability of the test compound to modulate phosphorylation-dependent activation of AMPA receptors in the cell or tissue.

In another embodiment, the invention provides a method for regulating phosphorylation-dependent activation of AMPA receptors in a cell comprising administering an effective amount of a compound that modulates activity of CK1, Cdk5, PP-1, PP2C, PP2B and/or PP2A, wherein modulation of the activity of CK1, Cdk5, PP-1, PP2C, PP2B and/or PP2A results in an alteration in phosphorylation-dependent activation of AMPA receptors in the cell.

In another embodiment, the invention provides a method for treating a disorder characterized by an increase or a decrease in phosphorylation-dependent activation of AMPA receptors comprising administering an effective amount of a compound that modulates the activity of CK1, Cdk5, PP-1, PP2C, PP2B and/or PP2A.

In another embodiment, the present invention provides a method of identifying compounds capable of producing anti-depressant activity in vitro or in vivo. The method is based on the determination of DARPP-32 phosphorylation level patterns both before and after treatment of cells or tissues with a test compound. The in vitro and in vivo applications would include, but not be limited to, modulating activity in whole animals, in tissue slices, in broken cell preparations, in intact cells (including cell lines and primary cultures), and in isolated and purified cell preparations. As a result, the present invention also includes compositions identified by this method. One of skill would understand that once identified as capable of producing altered DARPP-32 phosphorylation level patterns similar to the known anti-depressant compounds, with serotonergic activity, the compound could be used to treat depression as well as other conditions in which serotonergic systems are involved. Such conditions would include, but not be limited to, a 5-HTR-related disorder, a CK1-related disorder, a Cdk5-related disorder, a AMPA-receptor-related disorder, or a PP-1-, PP2C-, PP2B- and/or PP2A-related disorder. In the context of the present invention, the compounds identified would be administered as an effective dose or amount which can be determined by one of skill in the art based on data from studies such as presented in this specification. Such data would include, but not be limited to, results from IC50 determinations.

The invention also provides methods of screening agents (or drugs or compounds) to select an agent that can potentially ameliorate and/or be used in treatment of 5-HTR-related, CK1-related, Cdk5-related, AMPA-receptor-related, or PP-1-, PP2C-, PP2B- and/or PP2A-related disorders.

The present invention also provides methods of identifying agents, e.g., drug screening assays that can be used in therapeutic methods for the treatment of 5-HTR-related, CK1-related, Cdk5-related, AMPA-receptor-related, or PP-1-, PP2C-, PP2B- and/or PP2A-related disorders.

The present invention also provides in vivo methods of identifying agents that can modulate the activity of CK1, Cdk5, AMPA receptor, PP-1, PP2C, PP2B and/or PP2A. Such methods can be employed alone or in conjunction with in vitro and in situ methods as disclosed herein. One such method comprises administering the agent to a non-human mammal. The amount (and/or rate) of activation (or inhibition) of CK1, Cdk5, AMPA receptor, PP-1, PP2C, PP2B and/or PP2A is then determined. An agent is identified as capable of modulating the activity of CK1, Cdk5, AMPA receptor, PP-1, PP2C, PP2B and/or PP2A when the amount (and/or rate) of activation (or inhibition) is increased or decreased in the presence of the agent relative to in the absence of the agent. In preferred embodiments, the non-human mammal is a rodent. In a more preferred embodiment, the rodent is a mouse.

In other embodiments, the agent is administered along with a 5-HTR agonist. The amount (and/or rate) of modulation of CK1, Cdk5, AMPA receptor, PP-1, PP2C, PP2B and/or PP2A activity is then determined. Since the administration of a 5-HTR agonist in the absence of the agent should result in an increase in CK1, PP2A and AMPA receptor activity and a decrease in Cdk5, PP-1, PP2C, PP2B and PP2A activity, an agent is identified as capable of modulating the activity of CK1, Cdk5, AMPA receptor, PP-1, PP2C, PP2B and/or PP2A when the amount (and/or rate) of activation is significantly increased or decreased in the presence of the agent relative to in the absence of the agent.

In other embodiments, the agent is administered along with a 5-HTR antagonist. The amount (and/or rate) of modulation of CK1, Cdk5, AMPA receptor, PP-1, PP2C, PP2B and/or PP2A activity is then determined. Since the administration of a 5-HTR antagonist in the absence of the agent should result in a decrease in CK1, PP2A and AMPA receptor activity and an increase in Cdk5, PP-1, PP2C, PP2B and PP2A activity, an agent is identified as capable of modulating the activity of CK1, Cdk5, AMPA receptor, PP-1, PP2C, PP2B and/or PP2A when the amount (and/or rate) of activation is significantly increased or decreased in the presence of the agent relative to in the absence of the agent. In The in vivo method can further comprise administering the agent to a non-human mammal. Such animal models are disclosed in Section 5.5.

In a specific embodiment, the animal model is a homozygous DARPP-32 knockout mouse (see U.S. Pat. No. 5,777, 195, by Fienberg et al., issued Jul. 7, 1998; U.S. Pat. No. 6,013,621, by Nishi et al., issued Jan. 11, 2000; and Fienberg et al.,1998, Science 281:838-842; each of which is incorporated herein by reference in its entirety). In one embodiment, the homozygous DARPP-32 knockout mouse may be used, in an additional test or assay to validate or confirm that a candidate agent modulates CK1, Cdk5, AMPA receptor, PP-1, PP2C, PP2B and/or PP2A activity. In a specific embodiment, the validation may be carried out according to the methods described in Nishi et al. (U.S. Pat. No. 6,013, 621, issued Jan. 11, 2000). When such an agent is identified that modulates the activity of CK1, Cdk5, AMPA receptor, PP-1, PP2C, PP2B and/or PP2A via DARPP-32 phosphorylation, the presence of or administration of the agent in the DARPP-32 knockout mouse should not significantly increase or decrease the amount (and/or rate) of phosphorylation dependent activation of AMPA receptors relative to the absence or non-administration of the agent.

In certain embodiments, combinatorial libraries of chemical compounds, based on different structural skeletons (e.g., purines), as well as unrelated naturally occurring compounds, can be tested as drug candidates. In a preferred embodiment of this type, the assay is performed using high throughput technology with automated robotic technology as disclosed herein. Positive results ("hits") represent either the reduced or increased activity of CK1, Cdk5, AMPA receptor, PP-1, PP2C, PP2B and/or PP2A, as compared to the control reactions (in which the drug candidate is not included in the assay).

Once a drug candidate is selected, structural variants of the drug candidate can be tested. These compounds can also be scrutinized and modified with parameters such as membrane permeability, specificity of effects, and toxicity. The selected (e.g., the most potent) compounds of this secondary screening can then be evaluated in situ and in animal models (see Section 5.5) to determine whether the selected compounds alter the activity of CK1, Cdk5, AMPA receptor, PP-1, PP2C, PP2B and/or PP2A, and/or induce predicted behavioral alterations with minimal to no side-effects. Such behavioral abnormalities may include, but not be limited to, testing locomotor activity, e.g., administration of drugs of abuse to mice result in increased locomotor activity (see, e.g., Kosten et al., J. Pharmacol., Exp. Ther. 269:137-144 (1994); U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety); and/or self-administration of selected drugs or in prepulse inhibition (see, e.g., U.S. Pat. No. 5,777,195 Issued Jul. 7, 1998, incorporated herein by reference in its entirety). These tests can be then be followed by human trials in clinical studies. Alternatively, in certain embodiments, human trials in clinical studies can be performed without animal testing. Compounds affecting targets other than CK1 or Cdk5 can also be similarly screened, using alternative targets exemplified below.

Alternatively, modulators (e.g., activators or inhibitors) of CK1, Cdk5, AMPA receptor, PP-1, PP2C, PP2B and/or PP2A activity can be obtained by screening, e.g., a random peptide library produced by recombinant bacteriophage (see, e.g., Scott and Smith, Science 249:386-390 (1990); Cwirla et al., Proc. Natl. Acad. Sci. USA 87:6378-6382 (1990); Devlin et al., Science 249:404-406 (1990)) or a chemical library. Using the "phage method" very large libraries can be constructed (106-108 chemical entities). A second approach may be to use chemical methods, of which the Geysen method (Geysen et al., Molecular Immunology 23:709-715 (1986); Geysen et al. J. Immunologic Method 102:259-274 (1987)) and the method of Fodor et al. (Science 251:767-773 (1991)) are examples. Furka el al. (14th international Congress of Biochemistry, Volume 5, Abstract FR:013 (1988); Furka, Int. J. Peptide Protein Res. 37:487-493 (1991)), Houghton (U.S. Pat. No. 4,631,211, issued December 1986) and Rutter et al. (U.S. Pat. No. 5,010,175, issued Apr. 23, 1991) disclose methods to produce a mixture of peptides that can be tested as modulators of CK1, Cdk5, AMPA receptor, PP-1, PP2C, PP2B and/or PP2A activity.

In another aspect, synthetic libraries (Needels et al., Proc. Natl. Acad. Sci. USA 90:10700-4 (1993); Ohlmeyer et al., Proc. Natl. Acad. Sci. USA 90:10922-10926 (1993); Lam et al., International Patent Publication No. WO 92/00252; Kocis et al., International Patent Publication No. WO 94/28028, each of which is incorporated herein by reference in its entirety), and the like can be used to screen for modulators of CK1, Cdk5, AMPA receptor, PP-1, PP2C, PP2B and/or PP2A activation, according to the present invention. Once a potential modulator is identified, chemical analogues can be either selected from a library of chemicals as are commercially available (e.g., from Chembridge Corporation, San Diego, Calif. or Evotec OAI, Abingdon, UK), or alternatively synthesized de novo. The prospective agent (drug) can be placed into any standard assay to test its effect on the activity of CK1, Cdk5, AMPA receptor, PP-1, PP2C, PP2B and/or PP2A activation. A drug is then selected that modulates the activity of CK1, Cdk5, AMPA receptor, PP-1, PP2C, PP2B and/or PP2A activation.

The present invention also contemplates screens for small molecules, analogs thereof, as well as screens for natural modulators of CK1, Cdk5, AMPA receptor, PP-1, PP2C, PP2B and/or PP2A, such as those molecules that bind to and inhibit or activate 5-HTR (e.g., 5-HT2R, 5-HT4R or 5-HT6R), CK1, Cdk5, AMPA receptor, PP-1, PP2C, PP2B and/or PP2A in vivo. Alternatively, natural products libraries can be screened using assays of the invention for molecules that modulate 5-HTR, CK1, Cdk5, AMPA receptor, PP-1, PP2C, PP2B and/or PP2A activity.

In one particular assay, the target e.g., 5-HTR, CK1, Cdk5, AMPA receptor, PP-1, PP2C, PP2B and/or PP2A, can be attached to a solid support. Methods for placing such targets on the solid support are well known in the art and include such things as linking biotin to the target and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the target can be determined. Alternatively, or in addition, the dissociation constant between the labeled potential modulator and the target, for example, can be determined. Suitable labels for either the target or the potential modulator are disclosed herein.

In another aspect of the present invention, a potential modulator can be assayed for its ability to modulate the phosphorylation of Thr32 DARPP-32 by PKA or its dephosphorylation by PP2B, the phosphorylation of Thr75 DARPP-32 by Cdk5 or its dephosphorylation by PP2A, or the phosphorylation of Ser137 DARPP-32 by CK1 or by activation of PLC or its dephosphorylation by PP2C, either independently, or subsequent to, a binding assay as disclosed herein. In one such embodiment, the amount and/or rate of phosphorylation or dephosphorylation of Thr34 DARPP-32, Thr75 DARPP-32 or Ser137 DARPP-32, or a fragment thereof comprising the Thr34, Thr75 or Ser137 residue, respectively, is determined. Such assays are disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety.

In another aspect of the present invention, a potential modulator of CK1 can be assayed for its ability to modulate the phosphorylation of Ser 137 DARPP-32 or a phosphorylatable fragment of DARPP-32 comprising Serine-137 either independently, or subsequent to a binding assay as disclose herein. In one such embodiment, the amount and/or rate of phosphorylation of Ser137 DARPP-32, or a phosphorylatable fragment of DARPP-32 comprising the Serine 137 residue, is determined by the assays mentioned above.

In another aspect of the present invention, a potential modulator of Cdk5 can be assayed for its ability to modulate the phosphorylation of Thr75 DARPP-32 or a phosphorylatable fragment of DARPP-32 comprising Threonine-75 (i.e., the Cdk5-Nck5a complex) either independently, or subsequent to a binding assay as disclose herein. In one such embodiment, the amount and/or rate of phosphorylation of Thr75 DARPP-32, or a phosphorylatable fragment of DARPP-32 comprising the threonine-75 residue, is determined by the assays mentioned above.

In another aspect of the present invention, a potential modulator of AMPA receptors can be assayed for its ability to modulate the phosphorylation of Thr34 DARPP-32 or a phosphorylatable fragment of DARPP-32 comprising Threonine-34 either independently, or subsequent to a binding assay as disclose herein. In one such embodiment, the amount and/or rate of phosphorylation of Thr34 DARPP-32, or a phosphorylatable fragment of DARPP-32 comprising the Threonine-34 residue, is determined by the assays mentioned above. In another embodiment, the methods of Yan et al. (1999, Nature Neurosci. 3:13-17) can be used to assay for AMPA receptor activity.

In another aspect of the present invention, a potential modulator of PP-1 can be assayed for its ability to modulate the dephosphorylation of Thr34 DARPP-32 or a dephosphorylatable fragment of DARPP-32 comprising Threonine-34 either independently, or subsequent to a binding assay as disclose herein. In one such embodiment, the amount and/or rate of dephosphorylation of Thr34 DARPP-32, or a dephosphorylatable fragment of DARPP-32 comprising the Threonine-34 residue, is determined by the assays mentioned above.

In another aspect of the present invention, a potential modulator of PP2C can be assayed for its ability to modulate the dephosphorylation of Ser137 DARPP-32 or a dephosphorylatable fragment of DARPP-32 comprising Serine-137 by either independently, or subsequent to a binding assay as disclose herein. In one such embodiment, the amount and/or rate of dephosphorylation of Ser137 DARPP-32, or a dephosphorylatable fragment of DARPP-32 comprising the serine-137 residue, is determined by the assays mentioned above or by the assays disclosed in Section 8.

In another aspect of the present invention, a potential modulator of PP2B can be assayed for its ability to modulate the dephosphorylation of Thr34 DARPP-32 or a dephosphorylatable fragment of DARPP-32 comprising Threonine 34 either independently, or subsequent to a binding assay as disclose herein. In one such embodiment, the amount and/or rate of dephosphorylation of Thr34 DARPP-32, or a dephosphorylatable fragment of DARPP-32 comprising the Threonine 34 residue, is determined by the assays mentioned above.

In another aspect of the present invention, a potential modulator of PP2A can be assayed for its ability to modulate the dephosphorylation of Thr75 DARPP-32 or a dephosphorylatable fragment of DARPP-32 comprising Threonine-75 by either independently, or subsequent to a binding assay as disclose herein. In one such embodiment, the amount and/or rate of dephosphorylation of Thr75 DARPP-32, or a dephosphorylatable fragment of DARPP-32 comprising the threonine-75 residue, is determined by the assays mentioned above.

Thus, a modulator that inhibits, or in the alternative stimulates, phosphorylation of DARPP-32 is then selected. In a particular embodiment, the effect of a potential modulator on the catalytic activity of a serotonergic intracellular signaling molecule, including, but not limited to, CK1 (e.g., CK1α, CK1β, CK1γi, CK1γ2, CK1γ3, CK1δ, CK1 ε), Cdk5, AMPA receptor, PP-1, PP2C (including, but not limited to, PP2Ca, PP2Cb and PP2Cg), PP2B and/or PP2A, is determined. The potential modulator can then be tested for its effect on the physiological consequence of PKA inhibition by phospho-Thr75 DARPP-32. For this purpose, voltage-gated $Ca^{2+}$ currents, (which are known to be regulated by PKA) can be analyzed using patch-clamp recordings of dissociated striatal neurons. Such methods are disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959 by Bibb et al., entitled "Methods of Identifying Agents That Regulate Phosphorylation/Dephosphorylation in Dopamine Signaling," filed Oct. 13, 2000, each of which is incorporated herein by reference in its entirety.

In another embodiment, a potential modulator can be added to a striatal tissue slice (as disclosed in Sections 6 and 7). Tissue samples can be treated with various concentrations of a potential modulator and the sample can then be analyzed for activity of CK1, Cdk5, AMPA receptor, PP-1, PP2C, PP2B and/or PP2A. Potential modulators of the activity of CK1, Cdk5, AMPA receptor, PP-1, PP2C, PP2B and/or PP2A can be tested for example, on intact neurons in situ by treatment of acutely prepared neostriatal slices incubated in Krebs bicarbonate buffer solution containing the reagent. The effects of these compounds can be tested by empirically defining the optimal concentration and time of incubation.

In another embodiment, an animal model (see Section 5.5) can be used to ascertain the effect of a potential agent on a 5-HTR-related condition. A potential modulator that ameliorates the 5-HTR-related condition can then be selected. For example, a locomotor behavioral response of the animal can be determined in the presence and absence of the agent. In specific embodiment, locomotor activity of an animal, e.g., a mouse can be measured in an activity monitor as disclosed in Section 6. In a specific embodiment, a rodent tail-suspension test (as disclosed in Section 7) can be used as an experimental model to predict antidepressant efficacy.

Methods of testing a potential therapeutic agent (e.g., a candidate drug, potential modulator, etc.) in an animal model are well known in the art. Thus potential therapeutic agents can be used to treat whole animals. The potential modulators can be administered by a variety of ways including topically, orally, subcutaneously, or intraperitoneally (such as by intraperitoneal injection) depending on the proposed use. Optimal dose will be empirically defined. Animals can be sacrificed by focused microwave beam irradiation, for example.

In a specific embodiment, homogenates of striatal tissue are subjected to immunoblot analysis. An alternative approach that can be employed assesses the potential efficacy of these compounds in relieving 5-HTR-related pathological symptoms in animal models for disease. For example, animals ectopically expressing the human disease causing form of the Huntington s disease (HD) gene exhibit neuropathological symptoms similar to those of HD patients. Models such as these can be used to assess the efficacy of any potential therapeutic agents (see Section 5.5). Generally, at least two groups of animals are used in the assay, with at least one group being a control group in which the administration vehicle is administered without the potential modulator.

5.2.1. Enzymatic Assays for Kinases and Phosphatases

According to the methods of the invention, inhibitors of CK1, Cdk5, AMPA receptor, PP-1, PP2C, PP2B and/or PP2A can be identified by direct assay of isolated enzyme. Activities of kinase (e.g., CK1 or Cdk5) can be monitored by a variety of methods known to those skilled in the art, e.g., the methods disclosed in Parker, Law, et al., 2000, Development of high throughput screening assays using fluorescence polarization: nuclear receptor-ligand-binding and kinase/phosphatase assays, J. Biomolec. Screening 5(2): 77-88; Bader et al. (2001, Journal of Biomolecular Screening 6(4): 255-64); Liu, F., X. H. Ma, et al. (2001). "Regulation of cyclin-dependent kinase 5 and casein kinase 1 by metabotropic glutamate receptors." Proceedings of the National Academy of Sciences of the United States of America 98(20): 11062-8; Evans, D. B., K. B. Rank, et al. (2002). "A scintillation proximity assay for studying inhibitors of human tau protein kinase II/Cdk5 using a 96-well format." Journal of Biochemical & Biophysical Methods 50(2-3): 151-61.

Using such methods, samples containing the kinase of interest are exposed under the appropriate conditions to radioactive ATP and a synthetic peptide substrate of the appropriate composition to provide a site for phosphorylation. The radioactive phosphate newly associated with the peptide is then measured. Addition of a chemical moiety, such as biotin covalently linked to the substrate peptide, allows binding of the substrate peptide by a streptavidin-coated bead. Bead-bound peptide can be isolated and associated radioactivity measured, or, preferably, radioactivity associated with the substrate peptide can be measured directly using a bead suitable for scintillation proximity assays.

Activities of protein phosphatases (e.g, PP-1, PP2C, PP2B or PP2A) can be monitored by a variety of methods known to those skilled in the art, e.g., the methods disclosed in Cohen et al.(1988, Protein phosphatase-1 and protein phosphatase-2A from rabbit skeletal muscle, Methods Enzymol 159:390-408) or Stewart and Cohen (1988, Protein phosphatase-2B from rabbit skeletal muscle: a $Ca^{2+}$-dependent, calmodulin-stimulated enzyme, Methods Enzymol 159:409-16).

Modulators of CK1, Cdk5, AMPA receptor, PP-1, PP2C, PP2B and/or PP2A can also be identified by screening for modulators of DARPP-32 phosphorylation, i.e., Ser137 DARPP-32 phosphorylation (CK1), Thr75 DARPP-32 phosphorylation (Cdk5) or Thr34 DARPP-32 phosphorylation (PKA, PP2B, PP1). Such methods are disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000; and in U.S. Pat. No: 5,777,195, by Fienberg et al., issued Jul. 7, 1998, each of which is incorporated herein by reference in its entirety.

Phosphorylation of a peptide substrate can also be detected via direct binding of phosphospecific antibodies or by measuring displacement of a phosphospecific antibody from a competitor phosphopeptide (see, e.g., Parker, Law et al., 2000, Development of high throughput screening assays using fluorescence polarization: nuclear receptor-ligand-binding and kinase/phosphatase assays, J. Biomolec. Screening 5(2): 77-88). Fluorescence methods such as fluorescence resonance energy transfer (FRET) or fluorescence polarization (FP) can be used to detect the specific phosphopeptide-antibody complexes. These methods have the advantage that they employ "homogeneous" detection that is not dependent on isolation of the bound species, but rather depends on changes in fluorescence that occur owing to specific binding in solution. Methods of producing phosphospecific antibodies are well known in the art.

In one embodiment, the methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and U.S. Ser. No. 09/687,959, by Bibb et al., entitled "Methods of Identifying Agents That Regulate Phosphorylation/Dephosphorylation in Dopamine Signaling," filed Oct. 13, 2000, (each of which is incorporated herein by reference in its entirety) are used to produce phosphorylation state-specific antibodies having specificity for Thr34-phosphorylated, Thr75-phosphorylated, or Ser137-phosphorylated DARPP-32.

Fluorescence resonance energy transfer, or FRET, is widely used for homogeneous assays capable of detecting specific binding of macromolecules. FRET depends on the ability of excited "donor" fluorescent molecules (fluorophores) to transfer their energy to nearby "acceptor" fluorophores rather than emitting light. Thus, when the two fluorophores are brought together in space by binding to a substrate target, fluorescence emitted at the normal donor wavelength is reduced and fluorescence emitted by the acceptor fluorophore increases. Either the decrease in donor fluorescence or the increase in acceptor fluorescence can be used to measure the binding event.

In one embodiment, the methods disclosed in Bader et al. (2001, A cGMP-dependent protein kinase assay for high throughput screening based on time-resolved fluorescence resonance energy transfer, Journal of Biomolecular Screening 6(4): 255-64) are used to determine kinase activity. Bader et al. discloses a cGMP-dependent protein kinase assay for high throughput screening based on time-resolved fluorescence resonance energy transfer ("FRET"). Samples containing the kinase of interest are exposed to ATP and a synthetic peptide substrate with a Cdk5-specific phosphorylation site and an amino-terminal biotin moiety. Phosphorylated peptide is detected using allophycocyanin-labeled streptavidin, a phosphopeptide specific antibody, and a Europium-chelate-labeled secondary antibody. Simultaneous binding of the streptavidin and the phosphospecific antibody to a phosphorylated substrate molecule brings the Europium chelate "donor" on the secondary antibody close enough to the allophycocyanin fluorophore "acceptor" for fluorescence resonance energy transfer to occur, measurable as a decrease in Europium emission at 615 nm and an increase in allophycocyanin emission at 665 nm wavelength. The Europium—allophycocyanin donor—acceptor pair is commonly used in order to take advantage of the long fluorescence lifetime of excited Europium, thus the signal is "time-resolved".

Other pairs of fluorophores, such as coumarin and fluorescein isothiocyanate, can be used. Pairs of such molecules that can engage in fluorescence resonance energy transfer (FRET) are termed FRET pairs. In order for energy transfer to occur, the donor and acceptor molecules must typically be in close proximity (up to 70 to 100 Å (Clegg, 1992, Methods Enzymol. 211:353-388; Selvin, 1995, Methods Enzymol. 246: 300-334). The efficiency of energy transfer falls off rapidly with the distance between the donor and acceptor molecules. Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Fluorescence polarization measurements can also be used for measuring the activity of a protein kinase or a phosphatase (see, e.g., Parker, Law et al., 2000, Development of high throughput screening assays using fluorescence polarization: nuclear receptor-ligand-binding and kinase/phosphatase assays, J. Biomolec. Screening 5(2): 77-88; Turek et al., 2001, Anal. Biochem. 299: 45-53). Binding of a large specific antibody to a fluorescent small phosphopeptide slows its tumbling rate and increases the fluorescence polarization signal. Thus fluorescence polarization is proportional to the amount of bound fluorescent phosphopeptide. This assay can be used in a competitive mode, in which a fixed concentration of fluorescent peptide and antibody are added to a biological sample, and the presence of non-fluorescent phosphoprotein or phosphopeptide is recorded as a decrease in signal. It can also be used in a direct binding mode, in which phosphate addition (by kinase) or removal (by phosphatase) modulates antibody binding and thus polarization signal. In a specific embodiment, a fluorescence polarization assay is performed using the methods of Turek et al. (2001, Anal. Biochem. 299: 45-53), in which a product-specific anti-phosphorylated peptide-specific (e.g., anti-phosphoserine) antibody is used.

In certain embodiments, modulators (e.g., inhibitors) of Cdk5 can be identified via enzymatic assays using recombinant Cdk5 purified from bacteria after expression using vectors, using cell lysates containing Cdk5, or using brain tissue lysates (see, e.g., Leost et al., 2000, Eur. J. Biochem. 267: 5983-5994). In other embodiments, modulators of Cdk5 can be identified via enzymatic assays using recombinant Cdk5 purified from insect cells (e.g., Sf9 cells) after expression using baculovirus. In such assays, an enzyme or lysate is incubated at 30° C. with peptide substrate biotin-DARPP-32 (amino acid residues 67-82) (approximately 1 µM), in an appropriate buffer (500 µM ATP, 50 mM HEPES, pH7.5/10 mM MgCl$_2$, 1 mM dithiothreitol), in a final reaction volume of 40-60 µl. The reaction is halted by addition of an equal volume of stop buffer (30 mM EDTA, pH 7.0).

For detection of phosphorylated peptide, aliquots of the stopped reaction (20-30 µl) are added in triplicate to a 384-well black multiwell plate, followed by addition of two volumes of antibody mix containing rabbit polyclonal anti-phosphothr75-DARPP-32 antibody (1 nM), europium-labeled anti-rabbit IgG (1 nM), and streptavidin-allophycocyanin conjugate (2 µg/ml), in an appropriate buffer (0.1% BSA in phosphate-buffered saline, pH 7.4). After incubation at 20° C. for 1-24 hr, fluorescence is measured (excitation filter wavelength 340 nM; emission filter wavelength 660 nM) over a 200-µs period starting 50 µs after the excitation using Applied Biosystems Cytofluor. Other antibody combinations, such as a mouse monoclonal anti-phosphothr75 DARPP-32 and europium-labeled anti-mouse IgG, are contemplated according to the invention, and would be expected to give comparable results.

Inhibitors of CK1 can be identified via a similar enzymatic assay using isolated CK1, cell lysates containing CK1, or brain tissue lysates. In this assay, enzyme or lysate is incubated at 30° C. with peptide substrate biotin-DARPP-32 (amino acid residues 132-146) (approximately 1 µM), in an appropriate buffer (500 µM ATP, 50 mM HEPES, pH7.5/10 mM MgCl$_2$, 1 mM dithiothreitol), in a final reaction volume of 40-60 µl. The reaction is halted by addition of an equal volume of stop buffer (30 mM EDTA, pH 7.0).

For detection of phosphorylated peptide, aliquots of the stopped reaction (20-30 µl) are added in triplicate to a 384-well black multiwell plate, followed by addition of two volumes of antibody mix containing anti-phospho ser137-DARPP-32 antibody (1 nM), europium-labeled anti-mouse IgG (1 nM), and streptavidin-allophycocyanin conjugate (2

μg/ml), in an appropriate buffer (0.1% BSA in phosphate-buffered saline, pH 7.4). After incubation at 20° C. for 1-24 hr, fluorescence is measured (excitation filter wavelength 340 nM; emission filter wavelength 660 nM) over a 200-μs period starting 50 μs after the excitation using Applied Biosystems Cytofluor. Other antibody combinations, such rabbit polyclonal anti-phosphothr75 DARPP-32 and europium-labeled anti-rabbit IgG, are contemplated according to the invention, and would be expected to give comparable results.

In one form of the above-disclosed assay, recombinant enzyme, enzyme isolated from tissue, or tissue or cell lysate is incubated at 30° C. with biotin-peptide substrate providing a proline-directed phosphorylation site. Amino acid residues 67-82 of human DARPP-32, KRPNPCAYT-PPSLKAV (SEQ ID NO: 5), which are identical to phosphorylation sites in rat and mouse DARPP-32, provide such a substrate.

In another form of the above-disclosed assay, recombinant enzyme, enzyme isolated from tissue, or tissue or cell lysate is incubated at 30° C. with biotin-peptide substrate providing a casein kinase phosphorylation site. Amino acid residues 133-143 of human DARPP-32, EEEDSQAEVLK (SEQ ID NO: 6), which are identical to phosphorylation sites in rat and mouse DARPP-32, provide such a substrate.

Modulation of intracellular kinase activity in response to 5-HTR ligands can be monitored by a variety of means known to those skilled in the art. Cultured cells displaying 5-HTR on their cell surfaces can be incubated with agonists or antagonists, the intracellular kinases released by detergent lysis, and their activity measured by fluorescent detection of phosphorylation as disclosed above or by radioisotope tracer methods. Radioisotope tracer methods may be used such as those disclosed in, e.g., Liu, F., X. H. Ma, et al. (2001). "Regulation of cyclin-dependent kinase 5 and casein kinase 1 by metabotropic glutamate receptors." Proc. Natl. Acad. Sci. USA 98(20): 11062-8; Evans, D. B., K. B. Rank, et al. (2002). "A scintillation proximity assay for studying inhibitors of human tau protein kinase II/Cdk5 using a 96-well format." J. Biochem. Biophys. Meth. 50(2-3): 151-61; and McDonald et al., 1999, A scintillation proximity assay for Raf/MEK/ERK kinase cascade: High-throughput screening and identification of selective enzyme inhibitors, Anal. Biochem. 268: 318-329.

In another embodiment, a cell-based assay for phosphorylation is used. In a specific embodiment, signal transduction based on protein phosphorylation is visualized in vivo, e.g., in single living cells using fluorescent indicators, using methods such as those disclosed in Sato et al. (2002, Fluorescent indicators for imaging protein phosphorylation in single living cells, Nature Biotechnology 20(3): 287-94). Such sensors consist of two fluorescent protein molecules, separated by a flexible linker. The linker peptide contains a phosphorylation site and a phosphoprotein recognition element. Phosphorylation of the linker causes a conformational change that brings the two fluorescent proteins into close proximity, allowing FRET to occur and changing the fluorescent output of the system.

5.3. Compounds that Modulate the Activity of CK1, Cdk5, AMPA Receptor, PP-1, PP2C, PP2B and/or PP2A via a Serotonergic Receptor Signaling Pathway The present invention also provides compositions for modulating the activity of CK1, Cdk5, AMPA receptor, PP-1, PP2C, PP2B and/or PP2A including, but not limited to the following agents, drugs, compounds or small molecules disclosed hereinbelow. The invention also provides compositions for modulating the activity of AMPA receptors via modulation of the activity of CK1, Cdk5, AMPA receptor, PP-1, PP2C, PP2B and/or PP2A, including, but not limited to the following agents, drugs, compounds or small molecules disclosed hereinbelow. The invention also provides compositions for use in methods of treatment of 5-HTR-related, DA-related, CK1-related, Cdk5-related, AMPA-receptor-related, or PP-1-, PP2C-, PP2B- and/or PP2A-related disorder wherein the compositions modulate the activity of CK1, Cdk5, AMPA receptor, PP-1, PP2C, PP2B and/or PP2A, including, but not limited to the following agents, drugs, compounds or small molecules disclosed hereinbelow. In certain embodiments, the compositions modulate activity via a 5-HTR signaling pathway. In certain embodiments, the 5-HTR intracellular signaling pathway comprises: (i) activation of 5-HT4 and 5-HT6 receptors, which increases cAMP activation of PKA phosphorylation of Thr-34; (ii) activation of 5-HT4 and 5-HT6 receptors, which increases cAMP activation of PKA activation of protein phosphatase-2A (PP-2A) dephosphorylation of Thr-75; and/or (iii) activation of 5-HT2 receptors, which increases activation of PLC, which in turn increases calcium activation of CK1 dependent phosphorylation of Ser-137.

5-HTR agonists include, but are not limited to: 5-HTP, PCA, serotonin reuptake inhibitors (SSRIs) such as fluoxetine (Adofen, Deproxin, Fluctin, Fluctine, Fludac, Flufran, Flunil, Fluoxac, Fluoxeren, Fluoxil, Fluoxeron, Flutine, Fluxil, Fontex, Lovan, Margrilan, Oxetine, Prodep, Prozac, Prozac 20, Rowexetina, Seronil), Fluvoxamine (Favoxil); Fluvoxamine (Dumirox, Dumyrox, Faverin, Favoxil, Fevarin, Floxyfral, Luvox, Maveral); Clobazam (Frisium); Alprazolam (Frontal); and paroxetine (Paxil).

Mixed 5-HTR agonists/antagonists include, but are not limited to: Buspiron, Mianserin, Trazodone (Desyrel), and Mirtazepine (Remeron).

5-HTR antagonists include, but are not limited to: Risperidone, Clozapine, Olanzapine, Quetiapine, Ketanserin and Ritanserin.

Modulators of 5-HT intracellular signaling pathways include, but are not limited to, MAO inhibitors, e.g., Tranylciproamine (PARNATE®), Moclobemid and Phenelzine (NARDIL®).

Other modulators of 5-HT intracellular signaling pathways include, but are not limited to, tricyclic antidepressants, e.g., Imipramine (FRONIL®); Clomipramine (ANAFRANIL®) and Trimipramine (SURMONTIL®).

Other modulators of 5-HT intracellular signaling pathways include, but are not limited to: Perphenazine, Bupropion (WELLBUTRIN®), Venlataxine (EFFEXOR®) and Reboxetine.

Other modulators of 5-HT intracellular signaling pathways include, but are not limited to, CK1 inhibitors, e.g., CK1-7 (CK1-7) and Cdk5 inhibitors, e.g., butyrolactone.

Other modulators of 5-HT intracellular signaling pathways include, but are not limited to, PLC inhibitors (e.g., U73122), $Ca^{2+}$ chelators (e.g., BAPTA/AM).

Other modulators of 5-HT intracellular signaling pathways include, but are not limited to, calcineurin (PP2B) inhibitors, e.g., cyclosporin A, Cypermethrin 3-(2,2-Dichloroethenyl)-2,2-dimethylcyclopropane carboxylic acid cyano (3-phenoxyphenyl)methyl ester, Tacrolimus (FK506, Prograf), Deltamethrin and ISATX247 (Isotechnika).

It will be apparent to one of skill in the art that certain 5-HTR agonists or antagonists may have both agonist and antagonist properties. The compounds listed hereinabove are not limited by theory of mechanism but are applicable to the present invention independently of their classification.

The present invention also encompasses methods for designing new chemical compounds that have activity as modulators of 5-HTR intracellular signaling pathways, wherein these new chemical compounds may include, but not be limited to, any compound with the ability to either stimulate or inhibit 5-HTR intracellular signaling, and would include, but not be limited to, low molecular weight organic molecules capable of being delivered intracellularly.

The present invention further provides a method of performing rational drug design to develop drugs that can modulate activity of CK1, Cdk5, AMPA receptor, PP-1, PP2C, PP2B and/or PP2A and thereby ameliorate 5-HTR signaling pathway-related disorders. Such rational drug design can be performed using compounds that have been identified as agonists of antagonists of 5-HTR, or modulators of serotonergic intracellular signaling pathways, as a starting point. In another embodiment, compounds that have been identified as agonists or antagonists of CK1, Cdk5, AMPA receptor, PP-1, PP2C, PP2B and/or PP2A can be used as a starting point. Thus, the present invention provides screens and assays to allow more specific inhibitors to be identified. Such methods of rational drug design are well-known in the art. In a specific embodiment, the rational drug design methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties, are used.

Indeed, potential modulators can be examined through the use of computer modeling using a docking program such as GRAM, DOCK, or AUTODOCK (Dunbrack et al., Folding & Design 2:27-42 (1997)), to identify potential modulators of, e.g., a 5-HTR signaling pathway. These modulators can then be tested for their effect on CK1, Cdk5, AMPA receptor, PP-1, PP2C, PP2B and/or PP2A activity. This procedure can include computer fitting of potential modulators to the 5-HTR, CK1, Cdk5, AMPA receptor, PP-1, PP2C, PP2B and/or PP2A complex to ascertain how well the shape and the chemical structure of the potential modulator will bind to 5-HTR, CK1, Cdk5, AMPA receptor, PP-1, PP2C, PP2B and/or PP2A (see, e.g., Bugg et al., 1993, Scientific American (Dec.) 269(6):92-98; West et al., TIPS, 16:67-74 (1995)). Computer programs can also be employed to estimate the attraction, repulsion, and steric hindrance of the subunits with a modulator/inhibitor. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins. Initially, compounds known to bind 5-HTR (e.g., 5-HTP) or to CK1, Cdk5, AMPA receptor, PP-1, PP2C, PP2B and/or PP2A can be systematically modified by computer modeling programs until one or more promising potential analogs are identified. In addition systematic modification of selected analogs can then be systematically modified by computer modeling programs until one or more potential analogs are identified. Such analyses are well known to those of skill in the art and have been shown to be effective in the development of, e.g., HIV protease inhibitors (see, e.g., Lam et al., Science 263:380-384 (1994); Wlodawer et al, Ann. Rev. Biochem. 62:543-585 (1993); Appelt, Perspectives in Drug Discovery and Design 1:23-48 (1993); Erickson, Perspectives in Drug Discovery and Design 1:109-128 (1993)). Alternatively a potential modulator can be obtained by initially screening a random peptide library produced by recombinant bacteriophage, e.g., as disclosed hereinabove. A peptide selected in this manner is then systematically modified by computer modeling programs as disclosed above, and then treated analogously to a structural analog as disclosed above.

Once a potential modulator is identified, it can be either selected from a library of chemicals, as are commercially available (e.g., from Chembridge Corporation, San Diego, Calif. or Evotec OAI, Abingdon, UK). Alternatively, the potential modulator may be synthesized de novo. Potential peptide modulators may be synthesized by protein synthetic techniques, e.g., by use of a peptide synthesizer or other methods of protein/peptide synthesis well known in the art. In one embodiment, the methods of protein/peptide synthesis disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled Methods of Identifying Agents That Regulate Phosphorylation/Dephosphorylation in Dopamine Signaling," filed Oct. 13, 2000, (incorporated herein by reference in their entireties) are used. The de novo synthesis of one or even a relatively small group of specific compounds is reasonable in the art of drug design.

Any of the potential agents, targets for the potential agents (e.g., 5-HTR, CK1, Cdk5, AMPA receptor, PP-1, PP2C, PP2B and/or PP2A) or DARPP-32 (such as $^{32}$P-Thr75 phosphorylated DARPP-32) can be labeled. Suitable labels include enzymes (e.g., alkaline phosphatase or horseradish peroxidase), fluorophores (e.g., fluorescein isothiocyanate (FITC), phycoerythrin (PE), Texas red (TR), rhodamine, free or chelated lanthanide series salts, especially Eu3+, to name a few fluorophores), chromophores, radioisotopes, chelating agents, dyes, colloidal gold, latex particles, ligands (e.g., biotin), chemiluminescent agents, magnetic beads or magnetic resonance imaging labels. When a control marker is employed, the same or different labels may be used for the receptor and control marker.

In embodiments wherein a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re is used, standard counting procedures known in the art may be utilized.

In embodiments wherein the label is an enzyme, detection may be accomplished by any of the presently utilized colorimetric, spectrophotometric, fluorospectrophotometric, amperometric or gasometric techniques known in the art.

A direct label is an example of a label that can be used according to the methods of the present invention. A direct label is an entity that, in its natural state, is readily visible, either to the naked eye (for example, by visual inspection through a compound or dissecting light microscope), or with the aid of an optical filter and/or applied stimulation, e.g., U.V. light to promote fluorescence. Examples of colored labels that can be used according to the methods of the present invention, include metallic sol particles, for example, gold sol particles such as those disclosed by Leuvering (U.S. Pat. No. 4,313,734); dye sol particles such as disclosed by Gribnau et al. (U.S. Pat. No. 4,373,932) and May et al. (WO 88/08534); dyed latex such as disclosed by May et al. (WO 88/08534), Snyder (EP-A 0280 559 and 0

281 327); or dyes encapsulated in liposomes as disclosed by Campbell et al. (U.S. Pat. No. 4,703,017).

Other direct labels include a radionucleotide, a luminescent moiety, or a fluorescent moiety including, but not limited, to, e.g., a modified/fusion chimera of green fluorescent protein (as disclosed in U.S. Pat. No. 5,625,048, issued Apr. 29, 1997, and WO 97/26333, published Jul. 24, 1997, each of which is incorporated herein by reference in its entirety).

In addition to these direct labeling devices, indirect labels comprising enzymes can also be used according to the present invention. Various types of enzyme-linked immunoassays are well known in the art, for example, enzyme-linked immunoassays using alkaline phosphatase, horseradish peroxidase, lysozyme, glucose-6-phosphate dehydrogenase, lactate dehydrogenase, or urease. These and other similar assays are well known in the art and are disclosed, e.g, in Engvall (1980, "Enzyme Immunoassay ELISA and EMIT," in Methods in Enzymology, 70: 419-439) and in U.S. Pat. No. 4,857,453.

In certain embodiments, proteins can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$Cl_2$]-methionine, the invention further contemplates labeling with [$^{14}$C]-amino acids and [$^{3}$H]-amino acids (with the tritium substituted at non-labile positions) (see, e.g., U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties).

5.4. Diagnostic and Therapeutic Methods

As disclosed herein, the invention provides agents, drugs, compounds and compositions that modulate the activity or expression of CK1, Cdk5, AMPA receptor, PP-1, PP2C, PP2B and/or PP2A.

The present invention also provides diagnostic and therapeutic methods for the treatment of a 5-HTR-related, DA-related CK1-related, Cdk5-related, AMPA-receptor-related, or PP-1-, PP2C-, PP2B- and/or PP2A-related, including, but not limited the use of such compositions or compounds in the treatment of a 5-HTR-related, DA-related, CK1-related, Cdk5-related, AMPA-receptor-related, or PP-1-, PP2C-, PP2B- and/or PP2A-related disorder.

In one aspect, the invention provides a method for treating a neuronal condition characterized by an increase or a decrease in phosphorylation dependent AMPA receptor activity comprising administering an effective amount of a compound according to the present invention to modulate CK1, Cdk5, AMPA receptor, PP-1, PP2C, PP2B and/or PP2A activity, and thus increase or decrease AMPA receptor phosphorylation state and/or activity via modulation of a 5-HTR signaling pathway. In one embodiment, the compound is identified by the methods of the invention disclosed herein.

In addition, the present invention provides methods for treating a 5-HTR-related, DA-related, CK1-related, Cdk5-related, AMPA-receptor-related, or PP-1-, PP2C-, PP2B- and/or PP2A-related disorder in an individual (e.g., a patient) or in an animal subject, by administering an effective amount of a compound of the invention to modulate CK1, Cdk5, AMPA receptor, PP-1, PP2C, PP2B and/or PP2A activity. In one embodiment, the agent promotes or increases the activity of CK1, Cdk5, AMPA receptor, PP-1, PP2C, PP2B and/or PP2A. In another embodiment, the agent inhibits or decreases the activity of CK1, Cdk5, AMPA receptor, PP-1, PP2C, PP2B and/or PP2A. In preferred embodiments, the agent promotes (or increases) or inhibits (or decreases) the activity via a serotonergic intracellular signaling pathway.

In a particular embodiment, a method of the invention is used to treat a 5-HTR-related, DA-related CK1-related, Cdk5-related, AMPA-receptor-related, or PP-1-, PP2C-, PP2B- and/or PP2A-related disorder in an individual that is related to a symptom and/or disease state characteristic of depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, or cancer.

Preferably the agent, compound or composition administered in the method of treatment can cross through the blood brain barrier in sufficient quantities and at a sufficient rate so as to allow the treatment of the disorder and thereby, the condition or disease. In one such embodiment, the agent is administered intravenously. In another embodiment, the agent is administered orally. More preferably the agent can cross the blood brain carrier without a carrier (for methods and routes of administration, see Section 5.6).

5.5. Models for Diseases or Disorders

According to the methods of the invention, an animal model for a disease or disorder related to a serotonergic receptor signaling pathway, including but not limited to depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain, and cancer, may be used in assays to screen for compounds that modulate the activity of CK1, Cdk5, AMPA receptor, PP-1, PP2C, PP2B and/or PP2A, or for compounds that ameliorate the symptoms of a 5-HTR-related, CK1-related, Cdk5-related, AMPA-receptor-related, or PP-1-, PP2C-, PP2B- and/or PP2A-related disorder.

In one embodiment, an animal model for a 5-HTR-related, DA-related CK1-related, Cdk5-related, AMPA-receptor-related, or PP-1-, PP2C-, PP2B- and/or PP2A-related disorder is used in screening assays according to the methods of the invention. Such animals can be mice, rats, hamsters, sheep, pigs, cattle, etc., and are preferably non-human mammals.

In one embodiment, a transgenic mouse is used as an animal model for Alzheimer's disease (see, e.g., Lewis et al.

(August; 2000), Neurofibrillary tangles, amyotrophy and progressive motor disturbance in mice expressing mutant (P301L) tau protein, Nature Genetics 25(4): 402-5, erratum in 2000, Nat. Genet. 26(1):127; Lewis et al. 2001, Enhanced neurofibrillary degeneration in transgenic mice expressing mutant tau and APP, Science 293(5534):1487-91; Gotz et al., 2001, Formation of neurofibrillary tangles in P301l tau transgenic mice induced by Abeta 42 fibrils, Science 293 (5534):1491-5). Lewis et al. (2000, Neurofibrillary tangles, amyotrophy and progressive motor disturbance in mice expressing mutant (P301L) tau protein, Nature Genetics 25(4): 402-5, erratum in 2000, Nat. Genet. 26(1):127) discloses a transgenic mouse expressing human P301L Tau protein. Animals from this strain of mice develop age-dependent Alzheimer's-like neurofibrillary tangles containing hyperphosphorylated tau and progressive motor disturbance. The effect of modulators of CK1 activation or subsequent Cdk5 activation, on the development of neurofibrillary tangles and neuronal dysfunction are studied in this model system. The effect of 5-HTR or DA receptor signaling pathway modulators on Abeta 42 stimulated formation of neurofibrillary tangles may also be studied in this animal model. In this case, Abeta 42 may be supplied by genetic cross of P301l Tau-expressing mice with human APP-expressing mice (e.g., Lewis et al 2001, Enhanced neurofibrillary degeneration in transgenic mice expressing mutant tau and APP, Science 293(5534):1487-91) or by direct injection of Abeta 42 into the brain of P301l Tau-expressing mice (e.g., Gotz et al., 2001, Formation of neurofibrillary tangles in P301l tau transgenic mice induced by Abeta 42 fibrils, Science 293(5534):1491-5). Such model animal systems may be used to screen for compounds useful in the treatment of Alzheimer's disease due to their effect on 5-HTR intracellular signaling pathways.

In another embodiment, a rat model of stroke is used. Brint et al. (1988, J. Cerebr. Blood Flow & Metab. 8:474-485) discloses a rat model of focal brain ischemia. De Vry et al. (2001, Eur. J. Pharmacol. 428: 203-214) discloses a rat acute subdural hematoma model and a rat middle cerebral artery occlusion model that was used to investigate the neuroprotective and behavioral effects of a 5-HTR antagonist, BAY 36-7620. Bao et al. (2001, Brain Res. 922:173-179) discloses a rat model of focal cerebral ischemia in which group I 5-HTR receptor agonists and antagonists were tested. Tanaka et al. (2002, Brain Research 924:98-108) disclose a method of measurement of stroke by middle cerebral artery occlusion. Such a model animal system may be used to screen for compounds useful in the treatment of stroke due to their effect on 5-HTR intracellular signaling pathways.

In another embodiment, a mouse model of schizophrenia is used (Sipes et al., 1995, 8-OH-DPAT disruption of prepulse inhibition in rats: reversal with (+)WAY 100,135 and localization of site of action, Psychopharmacology (Berl) 117(1):41-8; Cao et al., 2002, Brain Research 937: 32-40). Such a model animal system may be used to screen for compounds useful in the treatment of schizophrenia due to their effect on 5-HTR intracellular signaling pathways.

In other embodiments, a rat model for attention-deficit disorder (ADD) or attention-deficit hyperactivity disorder (ADHD) is used (see, e.g., Hansen et al., 1999, Alcohol responsiveness, hyperreactivity and motor restlessness in an animal model for attention-deficit hyperactivity disorder, Psychopharmacology 146: 1-9; Russell, 2002, Behavioral Brain Res. 130: 191-196). Russell, for example, discloses a spontaneously hypertensive rat model that is a genetic model for ADHD. Such a model animal system may be used to screen for compounds useful in the treatment of ADHD due to their effect on 5-HTR intracellular signaling pathways.

In another embodiment, a mouse model of pain is used (e.g., O'Callaghan et al., 1975, Quantification of the analgesic activity of narcotic antagonists by a modified hot-plate procedure, J. Pharmacol Exp Ther 192: 497-505; Guarna et al., 2002, J. Neurochem. 80:271-277; Menéndez et al., 2002, Unilateral hot plate test: a simple and sensitive method for detecting central and peripheral hyperalgesia in mice, J. Neurosci. Methods 113:91-97). Guarna et al. discloses a mouse model for acute thermonociception. Menéndez et al. discloses a mouse model for central and peripheral hyperalgesia. Such a model animal system may be used to screen for compounds useful in the treatment of pain due to their effect on 5-HTR intracellular signaling pathways.

In another embodiment, a rat model of addiction (e.g., cocaine addiction) is used (Caine and Koob, 1995, Pretreatment with the dopamine agonist 7-OH-DPAT shifts the cocaine self-administration dose-effect function to the left under different schedules in the rat, Behav. Pharmacol 6: 333-347; Orsini el al., 2002, Brain Research 925:133-140). Such a model animal system may be used to screen for compounds useful in the treatment of drug abuse or addiction due to their effect on 5-HTR intracellular signaling pathways.

In another embodiment, a mouse model of Parkinson's disease is used (Uhl et al., 1985, Lancet 1:956-57; Mokry, 1995, Experimental models and behavioral tests used in the study of Parkinson's Disease, Physiol. Res. 44: 143-50.; Du, 2001, Proc. Natl. Acad. Sci. USA 98: 14669-14674). Such a model animal system may be used to screen for compounds useful in the treatment of Parkinson's disease due to their effect on 5-HTR intracellular signaling pathways. In an alternative embodiment, a rat model of Parkinson's disease is used. In a specific embodiment, rats are unilaterally (i.e. in one hemisphere) injected with 6-OHDA (6-hydroxydopamine; a dopaminergic neurotoxin) according to standard methods. The 6-OHDA is selectively taken up by dopaminergic neurons and kills the neurons. Such 6-OHDA-lesioned animals are considered an animal model of Parkinson's disease (see Section 6).

In another embodiment, an animal or tissue model of epilepsy is used (see, e.g., Paschoa et al., 1997, Seizure patterns in kindling and cortical stimulation models of experimental epilepsy, Brain Res. 770: 221-227; Kokaia, 1995, Exper. Neurol. 133:215-224; Merlin, 1999, J. Neurophysiol. 82: 1078-1081; Merlin, 2001, J. Neurophysiol. 87:621-625). Kokaia (1995, Exper. Neurol. 133:215-224) discloses a mouse model of epilepsy. Merlin (1999, J. Neurophysiol. 82: 1078-1081; 2001, J. Neurophysiol. 87:621-625) discloses a guinea pig hippocampal slice model of epilepsy. Such model animal or tissue systems may be used to screen for compounds useful in the treatment of epilepsy due to their effect on 5-HTR intracellular signaling pathways.

In another embodiment, a rodent (e.g., mouse) model of cancer, tumor formation, or carcinogenesis is used. Such rodent models are well known to those of skill in the art (see, e.g., Sato et al., 1997, A metastatic and androgen-sensitive human prostate cancer model using intraprostatic inoculation of LNCaP cells in SCID mice, Cancer Res. 15:1584-1589). For example, in certain embodiments, tumors may be grown subcutaneously in athymic nude mice (see, e.g., Singh et al., 2002, Cancer Res. 62:3063-3069). Such model animal systems may be used to screen for compounds useful in the treatment of cancer or tumors due to their effect on 5-HTR intracellular signaling pathways.

In another embodiment, a rodent tail-suspension test (as described in Section 7) can be used as an experimental model to predict antidepressant efficacy.

In a specific embodiment, the animal model is a homozygous DARPP-32 knockout mouse (see U.S. Pat. No. 5,777,195, by Fienberg el al, issued Jul. 7, 1998; U.S. Pat. No. 6,013,621, by Nishi et al., issued Jan. 11, 2000; and Fienberg et al., 1998, Science 281:838-842; each of which is incorporated herein by reference in its entirety). In one embodiment, the homozygous DARPP-32 knockout mouse may be used, in an additional test or assay to validate or confirm that a candidate agent modulates CK1, Cdk5, AMPA receptor, PP-1, PP2C, PP2B and/or PP2A activity. In a specific embodiment, the validation may be carried out according to the methods described in Nishi et al. (U.S. Pat. No. 6,013,621, issued Jan. 11, 2000). When such an agent is identified that modulates the activity of CK1, Cdk5, AMPA receptor, PP-1, PP2C, PP2B and/or PP2A via DARPP-32 phosphorylation, the presence of or administration of the agent in the DARPP-32 knockout mouse should not significantly increase or decrease the amount (and/or rate) of activation of AMPA receptors relative to the absence or non-administration of the agent.

5.6. Pharmaceutical Compositions

The invention encompasses pharmaceutical compositions for regulating CK1, Cdk5, AMPA receptor, PP-1, PP2C, PP2B and/or PP2A activity, and for diagnosing or treating a 5-HTR-related, DA-related, CK1-related, Cdk5-related, AMPA-receptor-related, or PP-1-, PP2C-, PP2B- and/or PP2A-related disorder. Because a loss of normal function results in the development of a phenotype of the above-listed diseases or disorders, activation of the serotonergic receptor (5-HTR) signaling pathway, or an increase in CK1-, Cdk5-, AMPA receptor-, PP-1-, PP2C-, PP2B- and/or PP2A-related activity (e.g., downstream activation) facilitates amelioration of a symptom in individuals exhibiting a symptom of such a disorder.

Alternatively, symptoms of certain 5-HTR-related, DA-related CK1-related, Cdk5-related, AMPA-receptor-related, or PP-1-, PP2C-, PP2B- and/or PP2A-related disorders may be ameliorated by decreasing the level of CK1-related, Cdk5-related, AMPA-receptor-related, or PP-1-, PP2C-, PP2B- and/or PP2A-related activity, and/or downregulating activity of a serotonergic receptor signaling pathway (e.g., by targeting downstream signaling events). Different approaches are discussed below.

In certain embodiments, the invention provides methods of administering an agent that can ameliorate a symptom of a 5-HTR-related disorder in a patient or subject exhibiting the symptom (see Section 5.4).

In certain embodiments, the invention provides methods of administrating an agent that can ameliorate a symptom of a 5-HTR-related, DA-related, CK1-related, Cdk5-related, AMPA-receptor-related, or PP-1-, PP2C-, PP2B- and/or PP2A-related disorder in a patient or subject exhibiting the symptom (see Section 5.4).

In certain embodiments, an agonist of 5-HTR activity, as disclosed herein, can be used to for treating a 5-HTR-related, DA-related, CK1-related, Cdk5-related, AMPA-receptor-related, or PP-1-, PP2C-, PP2B- and/or PP2A-related disorder. In other embodiments, an antagonist of 5-HTR activity, as disclosed herein can be used to for treating a 5-HTR-related, DA-related, CK1-related, Cdk5-related, AMPA-receptor-related, or PP-1-, PP2C-, PP2B- and/or PP2A-related disorder. It is not necessary that the compound demonstrate absolute specificity for the 5-HTR. For example, compounds that agonize both 5-HTR and another receptor may be used; such compounds may be administered so that delivery to the nervous system is optimized to achieve amelioration of a 5-HTR-related, DA-related, CK1-related, Cdk5-related, AMPA-receptor-related, or PP-1-, PP2C-, PP2B- and/or PP2A-related disorder.

5.6.1. Pharmaceutical Formulations

The present invention provides pharmaceutical compositions of the agents, drugs or compounds of the invention disclosed hereinabove. The agent, drug or compound, or their physiologically acceptable salts or solvates, may be formulated for administration for injection, or for oral, topical, nasal, inhalation, insufflation (either through the mouth or the nose) buccal, parenteral, rectal administration or other forms of administration. The invention provides pharmaceutical compositions comprising effective amounts of an agent(s) of the invention together with pharmaceutically acceptable diluents, preservatives, solubilizers, emulsifiers, adjuvants, excipients and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol).

The compositions may also be incorporated into particulate preparations of polymeric compounds such as polylactic acid, polyglycolic acid, etc. or liposomes. Hyaluronic acid may also be used. Biocompatible absorbable polymers may be selected from the group consisting of aliphatic polyesters, copolymers and blends, which include, but are not limited to, homopolymers and copolymers of lactide (which include D-, L-, lactic acid and D-, L- and meso lactide), glycolide (including glycolic acid), epsilon-caprolactone, p-dioxanone (1,4-dioxan-2-one, which is disclosed in U.S. Pat. No. 4,052,988), alkyl substituted derivatives of p-dioxanone (i.e., 6,6-dimethyl-1,4-dioxan-2-one which is disclosed in U.S. Pat. No. 5,703,200), triethylene carbonate (1,3-dioxan-2-one), alkyl substituted derivatives of 1,3-dioxanone (which are disclosed in U.S. Pat. No. 5,412,068), delta-valerolactone, beta-butyrolactone, gamma-butyrolactone, epsilon-decala tone, hydroxybutyrate, hydroxyvalerate, 1,4-dioxepan-2-one (disclosed in U.S. Pat. No. 4,052,988 and its dimer 1,5,8,12-tetraoxacyclotetradecane-7,14 dione), 1,5-dioxepan-2-one, and polymer blends thereof.

Such compositions may influence physical state, stability, rate of in vivo release, and rate of in vivo clearance of the present proteins and derivatives. See, e.g., Remington s Pharmaceutical Sciences, 18th ed., (1990, Mack Publishing Co., Easton, Pa. 18042) pages 1435-1712). The compositions may be prepared in liquid form, or be in dried powder, such as lyophilized form.

Contemplated for use herein are oral solid dosage forms, which are disclosed generally in Remington s Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate the present compositions (as, for example, proteinoid microspheres reported U.S. Pat. No. 4,925,673). Liposomal encapsulation may be used and the lipomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979). In general, the formulation will include the agent and inert ingredients (which allow for protection against the stomach environment and release of the biologically active material in the intestine).

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic, i.e., powder; for liquid forms, a soft gelatin shell may be used. The shell material of cachets may be thick starch or other edible paper. For pills, lozenges, molded tablets or tablet triturates, moist massing techniques can be used.

The therapeutic can be included in the formulation as fine multi-particulates in the form of granules or pellets. The formulation of the material for capsule administration can also be as a powder, lightly compressed plugs or even as tablets. The therapeutic can also be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material or filler. These diluents or fillers can include carbohydrates, especially mannitol, a-lactose, anhydrous lactose, cellulose (e.g., microcrystalline cellulose), sucrose, calcium hydrogen phosphate modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch (e.g., potato starch or the commercial disintegrant based on starch, Explotab). Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch (e.g., pregelatinised maize starch) and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic.

An anti-frictional agent may be included in the formulation of the therapeutic to prevent stiCKIng during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes, talc and silica. Soluble lubricants may also be used such as sodium lauryl sulfate, magnesium lauryl sulfate, polyethylene glycol of various molecular weights, Carbowax 4000 and 6000.

Glidants that can improve the flow properties of the drug during formulation and to aid rearrangement during compression can be added. The glidants can include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride or benzethomium chloride. The list of potential non-ionic detergents that can be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present in the formulation of the protein or derivative either alone or as a mixture in different ratios.

Additives that potentially enhance uptake of the agent are, for example, the fatty acids oleic acid, linoleic acid and linolenic acid.

Controlled release oral formulation may be desirable. The agent can be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane, which allows water to enter and to push the drug out through a single small opening due to osmotic effects.

Other coatings may be used for the formulation. These include a variety of sugars that can be applied in a coating pan. The therapeutic agent can also be given in a film coated tablet and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials can be used to provide the optimum film coating. Film coating may be carried out in a pan-coater or in a fluidized bed or by compression coating.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations disclosed previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5.6.2. Dosage Determinations

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.6.3. Routes of Administration

The component or components of a therapeutic composition of the invention may be introduced parenterally, topically, or transmucosally, e.g., orally, nasally, or rectally, or transdermally. Preferably, administration is parenteral, e.g., via intravenous injection, and also including, but not limited to, intra-arteriole, intramuscular, intradermal, subcutaneous, intraperitoneal, intraventricular, and intracranial administration. In preferred embodiments, the component or components of a therapeutic composition of the invention is introduced orally or parentally.

In preferred embodiments of the invention, an agent (or drug or compound) can cross and more preferably readily pass through the blood-brain barrier, which permits, e.g., oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid etc.

In another embodiment, an agent of the present invention is administered via the standard procedure of drilling a small hole in the skull to administer the agent.

In another embodiment, the molecule can be administered intracranially or, more preferably, intraventricularly. In another embodiment, osmotic disruption of the blood-brain barrier can be used to effect delivery of agent to the brain (Nilaver et al., Proc. Natl. Acad. Sci. USA 92:9829-9833 (1995)). In yet another embodiment, an agent can be administered in a liposome targeted to the blood-brain barrier. Administration of pharmaceutical agents in liposomes is known (see Langer, Science 249:1527-1533 (1990); Treat et al., in Liposomes in the Therapy of infectious Disease and Cancer, Lopez-Berestein and Fidler (eds.), Liss, New York, pp. pp. 317-327 and 353-365 (1989). All of such methods are envisioned in the present invention.

Although some predictions have been made concerning the ability of molecules to pass through the blood-brain barrier, these predictions are at best speculative. The rate and extent of entry of a compound into the brain are generally considered to be determined by partition coefficient, ionization constant(s), and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) (Glave and Hansch, J. Pharm. Sci. 61:589 (1972); Hansch et al., J. Pharm. Sci. 76:663 (1987)). In practice, the octanol-water partition system only provides a qualitative indication of the capability of a compound to cross the blood-brain barrier. For example, comparisons between known histamine H2 receptor antagonists suggest that there is no such simple relationship between their brain penetration and octanol water partition coefficients (Young et al., J. Med. Chem. 31:656 (1988)). Other factors, besides the octanol-water partition influence the propensity to cross the blood-brain barrier. Comparison of the ability of histamine H2 receptor antagonists to cross the blood-brain barrier suggests that brain penetration may increase with decreasing over-all hydrogen binding ability of a compound (Young et al., J. Med. Chem. 31:656 (1988)). Begley et al. (J. Neurochem. 55:1221-1230 (1990)) herein incorporated by reference in its entirety, discloses the ability of cyclosporin A to cross the blood-brain barrier. Methodology as used by Begley et al. includes: (1) measuring the brain uptake index (BUI) with the equation for a tritiated agent compound:

BUI=[(brain $^3$H/brain $^{14}$C)/(injectate $^3$H/injectate $^{14}$C)]× 100 where the $^{14}$C reference compound is $^{14}$C butanol or an analogous solvent; (2) Brain perfusion studies; (3) Intravenous bolus injection studies; and (4) Studies with cultured cerebral capillary endothelium.

In another embodiment, the therapeutic compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 317-327 and 353-365 (1989)). To reduce its systemic side effects, this may be a preferred method for introducing the agent.

In another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The following experimental examples are offered by way of illustration and not by way of limitation.

6. EXAMPLE 1

DARPP-32 Mediates Serotonergic Neurotransmission in the Forebrain

This example demonstrates that serotonin interacts with DARPP-32 in neuronal tissue as a signaling pathway for serotonin in neuronal cells and discloses additional therapeutic targets for treatment of conditions associated with serotonergic activity, such as depression.

6.1. Materials and Methods

6.1.1. Preparation and Treatment of Striatal Brain Slices

Neostriatal slices were prepared from male C57/BL6 mice (6-8 weeks old) in accordance with methods known in the art (Nishi, A. et al. 1997. J. Neurosci. 17:8147-8155). Briefly, slices (300-µm) from the neostriatum (dorsal striatum), nucleus accumbens (ventral striatum), and prefrontal cortex were prepared from adult male C57 Bl6 mice as described in (Nishi, A. et al. 1997. J. Neurosci. 17:8147-8155). The slices were preincubated in Krebs buffer (118 mM NaCl, 4.7 mM KCl, 1.5 mM $Mg_2SO_4$, 1.2 mM $KH_2PO_4$, 25 mM $NaHCO_3$, 11.7 mM glucose, 1.3 mM $CaCl_2$) at 30° C. under constant oxygenation (95% $O_2$/5% $CO_2$) for 60 min, with a change of buffer after 30 min. To prevent reuptake of serotonin into nerve terminals, slices were pretreated with the serotonin reuptake inhibitor, fluoxetine (10 µM), 2 min before the application of serotonin. The slices were thereafter treated with serotonin and other drugs as specified in each experiment. After drug treatment, the buffer was removed and the slices were rapidly frozen on dry ice and stored at −80° C. until immunoblotted.

6.1.2. Whole Animal Studies

In experiments examining the effects of para-chloroamphetamine (PCA) and 5-hydroxytryptophan (5-HTP) on DARPP-32 phosphorylation, adult male C57 Bl6 mice were injected i.p. with saline, PCA (4 mg/kg), or 5-HTP (50 mg/kg) and killed 15 min after the injection by focused microwave irradiation (4.5 5 kW for 1.4 s), using a small animal microwave (Muromachi Kikai, Tokyo). In these and all other experiments with 5-HTP, carbidopa (50 mg/kg) was administered 30 min before 5-HTP. The brains were rapidly removed, and striata and frontal cortices were dissected out and stored at 80 C. until assayed.

6.1.3. Immunoblotting

Frozen slices were sonicated in hot homogenization buffer containing 1% SDS and 50 mM NaF, and samples were boiled for 10 minutes. SDS-PAGE sample buffer was then added and samples were boiled for 5 minutes. Samples (approximately 120 µg of total protein) were separated by SDS-PAGE (10% polyacrylamide) and then transferred to nitrocellulose. In most studies, immunoblots were first probed with anti-phospho-Thr34 DARPP-32, anti-phospho-Thr75 DARPP-32, or anti-phospho-Ser137 DARPP-32 antibodies. Blots were stripped again and probed with anti-total DARPP-32 antibody. Antibody binding was revealed using the ECL immunoblotting detection system. Chemiluminescence was detected by autoradiography and bands were quantified by analysis of scanned images using NIH Image 1.52 software. In experiments using 1-methyl-4-phenyl-1,2, 3,6-tetrahydropyridine (MPTP)-pretreated mice, immunoblotting was also carried out with an antibody against tyrosine hydroxylase (Chemicon). Data on protein phosphorylation are expressed as percentage of control. In situ hybridization wild type (WT) mice and DARPP-32 KO mice (7) were given an i.p. injection with either saline, PCA (4 mg/kg), or 5-HTP (50 mg/kg) and killed 20 min postinjection by decapitation. In situ hybridization experiments against c-fos mRNA were carried out as described herein.

6.1.4. Locomotor Activity Measurements

Locomotor activity of WT and DARPP-32 KO mice was measured in activity monitors (43×44×45 cm) equipped with both horizontal and vertical sensors (Opto-Varimex, Columbus Instruments, Columbus, Ohio). Mice were acclimated to the boxes for 1 h, 24 days before the day of the experiment. The day of the experiment, mice were placed in the boxes for 20 min (habituation period) before drug administration. Saline, PCA(4mg/kg), or 5-HTP (50 mg/kg; 30 min after 50 mg/kg carbidopa i.p.) was injected i.p., and locomotor activity was measured for 50 min. In some experiments, adult male C57 Bl6 mice were pretreated with clozapine (0.3 mg/kg) 10 min before the administration of saline, PCA (4 mg/kg), or 5-HTP (50 mg/kg). Locomotor activity parameters (distance traveled and stereotypic movements) were quantified by using the AutoTrack System (Columbus Instruments).

6.2. Results

Neostriatal slices prepared from mouse brain (C57/BL6 strain) were used. Slices were treated with a variety of compounds that modulate serotonergic activity, as shown in Table 1, and the effect of these agents on the phosphorylation of DARPP-32 at three sites, Ser137, Thr34 and Thr75 was assessed using phosphorylation state-specific antibodies. In the case of studies of phosphorylation of Ser137 and Thr34, the incubation time was 2 minutes, while in the case of Thr75 the incubation time was 10 minutes. Control compounds used in these experiments included known signal transduction inhibitors as well as dopamine agonists and antagonists that had previously been shown to affect DARPP-32 phosphorylation (Nishi et al. 2000. Proc. Natl. Acad. Sci. USA 97:12840-12845).

6.2.1. Regulation by Serotonin of DARPP-32 Phosphorylation in Brain Slices

The results in Table 1 and FIG. 1 show that treatment of striatal slices in vitro with serotonin significantly increases phosphorylation of DARPP-32 at Thr34 and Ser137 while decreasing phosphorylation at Thr75.

TABLE 1

Phosphorylation Levels of Three Sites on DARPP-32 as measured In Vitro in Neostriatal Slices from Mouse Brain

| Compound Tested | Percent Phospho-Thr34 | Percent Phospho-Thr75 | Percent Phospho-Ser137 |
| --- | --- | --- | --- |
| Vehicle control | 100(17.0) | 100(5.0) | 100(3.9) |
| Serotonin (100 μM) | 342(26.7)* | 76(7.5)* | 141(6.0)* |
| Selective 5-HT Receptor Agonists | | | |
| Buspiron (5HT1A) (100 μM) | 66(10.6)* | 98(5.6) | 107(11.1) |
| Anpirtoline (5HT1B) (100 μM) | 86(3.7)* | 102(22.2) | 93(10.0) |
| DOI (5HT2) (100 μM) | 144(16.7) | 105(4.5) | 158(8.3)* |
| SR 57227 (5HT3) (100 μM) | 78(3.5)* | 88(4.8) | 105(9.6) |
| PPB (5HT4) (100 μM) | 218(36.1)* | 72(8.8)* | 108(2.0) |
| 5-MT (5HT4/6) (100 μM) | 261(31.5)* | 76(7.6)* | — |
| EMDT (5HT6 agonist) | 301(39.5)* | 76(7.6)* | 103(5.5) |
| Signal Transduction Inhibitors and Serotonin | | | |
| Tetrodotoxin (1.5 μM) | 91.8(5.8) | 103(3.5) | 98(12.5) |
| Tetrodotoxin + serotonin | 348(63.2)* | 83(8.1)* | 144(3.3)* |
| RpcAMPs (PKA inhibitor) (300 μM) | 88(13.1) | 105(7.2) | 108(10.0) |
| RpcAMPs + serotonin | 150(44.7)# | 102(9.5)# | 147(4.0)* |
| CK1-7 (CK1 inhibitor) (100 μM) | 102(11.5) | 96(10.0) | 87(4.0)* |
| CK1-7 + serotonin | 294(35.3)* | 77(9.1)* | 109(1.0)# |
| U-73122 (PLC inhibitor) (10 μM) | 117(10.9) | 90(6.6) | 86(6.2)* |
| U-73122 + serotonin | 297(34.0)* | 70(6.1)* | 89(3.7)# |
| Selective 5-HT Receptor Antagonists and Serotonin | | | |
| Ketanserin (5HT2) (10 μM) | 94(2.9) | 105(8.9) | 97(4.8) |
| Ketanserin + serotonin | 322(28.4)* | 78(12.1)* | 101(9.1)# |
| SDZ205,557 (5HT4) (10 μM) | 94(16.7) | 103(17.5) | 102(8.8) |
| SDZ205,557 + serotonin | 274(46.5)* | 92(14.5) | 125(5.0)* |
| Ro 07-6790 (5HT6) (10 μM) | 90(8.7) | 101(12.5) | 105(7.3) |
| Ro 07-6790 + serotonin | 225(28.5)#* | 96(8.4)# | 131(7.2)* |
| Ro 07-6790 + SDZ205,557 | 84(6.5) | 110(11.5) | 107(6.2) |
| Ro 07-6790 + SDZ205,557 + serotonin | 198(44.5)# | 98(6.1)# | 134(18.1)* |
| Clozapine (5HT2/6 and dopamine) (10 μM) | 124(19.8) | 101(13.4) | 105(5.5) |
| Clozapine + serotonin | 156(15.4)# | 98(5.2)# | 110(4.9)# |
| Dopamine Agonists/antagonists and Serotonin | | | |
| SKF 82958 (D1 agonist) (10 μM) | 552(39.1)* | 65(1.7)* | 115(14.7) |
| SKF 82958 + serotonin | 717(42.4)#* | 56(1.1)#* | 121(14.4) |
| Quinpirole (D2 agonist) (10 μM) | 65(4.7)* | 112(8.5) | 135(5.1)* |
| Quinpirole + serotonin | 125(12.7)# | 106(13.2)# | 186(11.1)# |

TABLE 1-continued

Phosphorylation Levels of Three Sites on DARPP-32 as measured In Vitro in Neostriatal Slices from Mouse Brain

| Compound Tested | Percent Phospho-Thr34 | Percent Phospho-Thr75 | Percent Phospho-Ser137 |
|---|---|---|---|
| SCH23390 (D1 antagonist) (10 μM) | 76(7.4)* | 109(6.5) | — |
| SCH23390 + serotonin | 303(37.6)* | 80(8.6)* | — |
| Raclopride (D2 antagonist) (10 μM) | 150(13.1)* | 85(11.4) | 101(12.7) |
| Raclopride + serotonin | 435(31.4)* | 66(4.5)#* | 131(13.5)* |
| D1 receptor knock-out mice + serotonin | 292(35.5)* | 81(3.9)* | 137(17.6)* |
| MPTP-treated mice + serotonin | 307(44.0)* | 80(9.2)* | 154(21.1)* |

*Denotes that the results were significantly different from the vehicle controls (saline; $p < 0.05$).
Denotes that the results were significantly different from animals treated with serotonin alone ($p < 0.05$).

The time-course and dose-response effects of serotonin on DARPP-32 phosphorylation are shown in FIG. 1.

Slices were prepared from neostriatum (dorsal striatum), nucleus accumbens (ventral striatum), and prefrontal cortex. Time-course experiments in neostriatal slices showed that serotonin (100 μM) caused a rapid increase in DARPP-32 phosphorylation at all three phosphorylation sites (FIGS. 1A-C), with the effect at Thr34 being the most pronounced. The state of phosphorylation of DARPP-32 at Thr34 and Ser137 returned to basal levels within 10 min (FIGS. 1A-C) and remained there at 30 min (not shown). In contrast, the small, but significant, increase in DARPP-32 phosphorylation at Thr75 was followed by a pronounced decrease in the state of phosphorylation at this site. No changes in the total levels of DARPP-32 were found at any time point. Based on these data, slices were incubated for 2 min for studies of phospho-Thr34 DARPP-32 and phospho-Ser137 DARPP-32, and for 10 min for studies of phospho-Thr75 DARPP-32 in all subsequent experiments. A lower concentration of serotonin was required to regulate DARPP-32 phosphorylation at Thr34 than at Thr75 and Ser137 (FIGS. 1D-F). The EC50 values for the effects of serotonin on DARPP-32 phosphorylation at Thr34, Thr75, and Ser137 were 13.5, 29.6, and 37.6 M, respectively. Using slices prepared from nucleus accumbens, it was found that 2 min of incubation with serotonin (100 μM) increased phosphorylation at Thr34 (307±25%, n=12) and Ser137 (143±7%, n =12), and that 10 min of incubation with serotonin decreased phosphorylation at Thr75 (75±6%, n=12). Experiments carried out in slices from the prefrontal cortex showed that 2 min of incubation with serotonin increased phospho-Thr34 DARPP-32 (185±15%, n=6) and that 10 min of incubation with serotonin decreased phospho-Thr75 DARPP-32 (85±3%, n=6). Because of a low signal in prefrontal cortex, the level of phospho-Ser137 DARPP-32 could not be accurately assayed in this area. Thus, the regulation of phosphorylation of DARPP-32 by serotonin was similar in all three brain regions. Because more slices can be collected from neostriatum than from nucleus accumbens, slices made from neostriatum were used in most of the subsequent experiments.

It is known that activators of PKA, compounds that increase phosphorylation of Thr34, such as rolipram, have anti-depressant activity. Rolipram is an inhibitor of cAMP phosphodiesterase type 4 and increases intracellular levels of cAMP and PKA activity. Several clinical trials have demonstrated that rolipram has anti-depressant efficacy in depressed patients (Horowski and Sastre-Y-Hernandez. 1985. Curr. Ther. Res. 38:23-29; Bobon et al. 1988. Eur. Arch. Psychiatry Neurol. Sci. 238:2-6; Fleischhacker et al. 1992. Neuropsychobiology 26:59-64). However, the data in striatal slices demonstrate for the first time, based on the ability of serotonin to modulate DARPP-32 phosphorylation, that activators of CK1 and PP2A or inhibitors of cdk5, PP2B or PP2C may have anti-depressant properties.

6.2.2. Effects of 5-Hydrocytryptamine (5-HT) Receptor Agonists on DARPP-32 Phosphorylation in Neostriatal and Cortical Slices Several serotonin receptors, most notably 5-HT1B, 5-HT2A C, 5-HT3, 5-HT4, and 5-HT6, are expressed throughout the striatum. The identity of the serotonin receptors involved in the serotonin-mediated regulation of DARPP-32 phosphorylation was determined by the use of selective agonists and antagonists. Results obtained with various serotonin agonists in neostriatal slices are shown in Table 1. 2-[1-(4-Piperonyl)piperazinyl]benzothiazole (PPB, a 5-HT4 receptor agonist) and 2-ethyl-5-methoxy-N,N-dimethyltryptamine (EMDT, a 5-HT6 receptor agonist, Eli Lilly & Co.), alone or together, qualitatively mimicked the action of serotonin at phospho-Thr34 DARPP-32 and phospho-Thr75 DARPP-32, but not at phospho-Ser137 DARPP-32. The EC50 values for the actions of PPB and EMDT at phospho-Thr34 DARPP-32 were 27.3 and 20.5 M, and at phospho-Thr75 DARPP-32 were 45.5 and 27.4 M, respectively. In addition, 5-methoxytryptamine (100 μM), which has a high affinity as an agonist at 5-HT4 and 5-HT6 receptors, increased phospho-Thr34 DARPP-32 (261±31%, n=12) and decreased phospho-Thr75 DARPP-32 (76±7%, n=12). Conversely, DOI [(±)-2,5-dimethoxy-4-iodoamphetamine hydrochloride; (±)-1-(2,5 dimethoxy-4-iodophenyl)-2-aminopropane], a 5-HT2A/C agonist, mimicked the action of serotonin at phospho-Ser137 DARPP-32, but not at phospho-Thr34 DARPP-32 and phospho-Thr75 DARPP-32. The EC50 value for DOI at phospho-Ser137 DARPP-32 was 18.2 μM. The 5-HT1B receptor agonist, anpirtoline (presumably by decreasing cAMP), and the 5-HT3 agonist, SR57227A (presumably by increasing $Ca^{2+}$), decreased phospho-Thr34 DARPP-32, but were without significant effects on phospho-Thr75 DARPP-32 and phospho-Ser137 DARPP-32. Using slices prepared from the prefrontal cortex, it was found that 2 min of incubation with the 5-HT4 receptor agonist, PPB, or the 5-HT6 receptor agonist, EMDT, increased phospho-Thr34 DARPP-32 (203±15%, n=6, and 185±19%, n=6, respectively), whereas 10 min of incubation with PPB or EMDT decreased phospho-Thr75 DARPP-32 (84±4%, n=6, and 80±17%, n=6, respectively).

6.2.3. Effects of 5-HT Receptor Antagonists on Serotonin-Mediated DARPP-32 Phosphorylation in Neostriatal Slices The results obtained with selective serotonin receptor antagonists (Table 1) were consistent with the results obtained with agonists. Thus, SDZ 205,557, a 5-HT4 receptor antagonist, and Ro 04-6790, a 5-HT6 receptor antagonist, alone or together, reduced the effects of serotonin on phospho-Thr34 DARPP-32 and phospho-Thr75 DARPP-32, but not on phospho-Ser137 DARPP-32. Conversely, ketanserin, a 5-HT2A/C receptor antagonist, reduced the effects of serotonin on phospho-Ser137 DARPP-32 phosphorylation, but not on phospho-Thr34 DARPP-32 or phospho-Thr75 DARPP-32. The multireceptor antagonist, clozapine, which has a particularly high affinity for 5-HT2 and 5-HT6 receptors (17), significantly counteracted serotonin-mediated phosphorylation of DARPP-32 at all sites examined. Taken together, the results obtained with serotonin receptor agonists and antagonists indicate that the effects of serotonin on DARPP-32 phosphorylation can be accounted for by activation of 5-HT2, 5-HT4, and 5-HT6 receptors.

6.2.4. Effects of Signal Transduction Modulators on Serotonin-Mediated DARPP-32 Phosphorylation in Neostriatal Slices To investigate whether the effects of serotonin on DARPP-32 phosphorylation were mediated through a direct action on DARPP-32-containing neurons, slices were pretreated with tetrodotoxin (TTX), which inhibits action potential-dependent synaptic transmission by blocking voltage-gated sodium channels. The actions of serotonin on DARPP-32 phosphorylation were unaffected by TTX, indicating a direct action (Table 1). The principal signal transduction pathways used by 5-HT2 and 5-HT4 5-HT6 receptors involve activation of phospholipase C and PKA, respectively. To investigate the contributions of these signaling pathways to the action of serotonin, striatal slices were pretreated with either U-73122, a selective phospholipase C inhibitor, or Rp-cAMPS, a selective PKA inhibitor, before the application of serotonin. As shown in Table 1, U-73122 blocked the effect of serotonin on phospho-Ser137 DARPP-32, but not on phospho-Thr34 DARPP-32 or phospho-Thr75 DARPP-32. Conversely, Rp-cAMPS inhibited the action of serotonin on phospho-Thr34 DARPP-32 and phospho-Thr75 DARPP-32, but not on phospho-Ser137 DARPP-32.

6.2.5. Characterization of Serotonin-Dopamine Interactions in the Regulation of DARPP-32 Phosphorylation To determine whether the effects of serotonin on DARPP-32 phosphorylation were mediated through modulation of dopaminergic signaling pathways, several types of experiments were carried out (Table 1). Serotonin and SKF 82958, a D1 receptor-selective agonist, had additive effects in increasing phospho-Thr34 DARPP-32 and decreasing phospho-Thr75 DARPP-32. Serotonin and quinpirole, a D2 receptor-selective agonist, had antagonistic effects on phospho-Thr34 DARPP-32 and phospho-Thr75 DARPP-32 and additive effects in increasing phosphorylation at phospho-Ser137 DARPP-32. The effects of serotonin on DARPP-32 phosphorylation were not significantly altered in slices from D1 receptor KO mice (unpublished results) or from mice pretreated with the dopaminergic neurotoxin, MPTP (Table 1), indicating that the effects of serotonin on DARPP-32 phosphorylation were not mediated through regulation of dopamine release.

6.2.6. Regulation of DARPP-32 Phosphorylation in Vivo by PCA and 5-HTP

Mice were injected i.p. with the serotonin releaser, PCA (4 mg/kg), the serotonin precursor, 5-HTP (50 mg/kg), or fluoxetine (0, 5 10 or 20 mg/kg). Fifteen minutes after injection, the mice were sacrificed by focused microwave irradiation (4.5-5 kW for 1.4 seconds) using a small animal microwave (Muromachi Kikai, Tokyo, Japan). Brains were rapidly removed and striata, cortices and hippocampi dissected out and stored at −80° C. until determination of levels of DARPP-32 phosphorylation at Thr34, Ser137, Thr75 and Ser102. Results are shown in Table 2 and FIG. 2. In experiments using vehicle control, 5-HTP+carbidopa and PCA, data were obtained only from tissue samples of striata. In experiments using fluoexetine, data were obtained from tissue samples of striata, cortices and hippocampi dissected out separately.

The results shown in Table 2 and FIG. 2 demonstrate that in striatum, PCA and 5-HTP cause a common pattern of alteration of DARPP-32 phosphorylation, i.e., an increase at phospho-Thr-34 DARPP-32 and phospho-Ser137 DARPP-32 and a decrease at phospho-Thr75 DARPP-32. Furthermore, in prefrontal cortex PCA and 5-HTP increased phospho-Thr34 DARPP-32 (147±4.8%, n=5 mice, and 144±8.3%, n=5 mice, respectively), but decreased phospho-Thr75 DARPP-32 (79±3.8%, n=5 mice, and 74±8.0%, n=5, respectively). Thus, serotonin regulates DARPP-32 phosphorylation in a qualitatively similar fashion both in vitro and in vivo.

TABLE 2

Levels of DARPP-32 Phosphorylation as Determined in Mice

| Compound Tested | Percent Phospho-Thr34 | Percent Phospho-Thr75 | Percent Phospho-Ser137 | Percent Phospho-Ser102 |
|---|---|---|---|---|
| Vehicle control | 100(5.6) | 100(7.3) | 100(3.9) | |
| 5-HTP + carbidopa (50 mg/kg each) | 164(10.1)* | 82.7(3.5)* | 125(4.9)* | |
| PCA (4 mg/kg) | 171(9.1)* | 80.1(3.4)* | 128(7.1)* | |
| Fluoxetine (0 mg/kg) Striatum | 100(7.7) | 100(5.2) | 100(10.8) | 100(10.1) |
| Fluoxetine (5 mg/kg) Striatum | 123(5.0)* | 95(3.1) | 120(8.7) | |
| Fluoxetine (10 mg/kg) Striatum | 155.2(12.9)* | 84.6(8.9)* | 128(9.2)* | 108(7.5) |
| Fluoxetine (20 mg/kg) Striatum | 141(7.6)* | 92(2.1)* | 127(8.7)* | |
| Fluoxetine (0 mg/kg) Cortex | 100(1.6) | 100(4.7) | | |
| Fluoxetine (5 mg/kg) Cortex | 144(7.4)* | 86(7.0)* | | |
| Fluoxetine (10 mg/kg) Cortex | 140(4.7)* | 85(4.2)* | | |
| Fluoxetine (20 mg/kg) Cortex | 131(11.5)* | 82(7.3)* | | |
| Fluoxetine (0 mg/kg) Hippocampus | 100(4.7) | 100(4.4) | | |
| Fluoxetine (5 mg/kg) Hippocampus | 150(3.8)* | 84(6.4)* | | |
| Fluoxetine (10 mg/kg) Hippocampus | 142(6.2)* | 87(3.0)* | | |
| Fluoxetine (20 mg/kg) Hippocampus | 141(11.6)* | 88(3.0)* | | |

*Denotes there was a statistically significant difference from the vehicle control (saline).

These in vivo data confirmed the results seen in vitro. Serotonin increased DARPP-32 phosphorylation at Thr34 and Ser137, while decreasing phosphorylation at Thr75. The effects were seen when a serotonin precursor alone was used (5-HTP), when a serotonin releasing agent was used (PCA), as well as when a serotonin reuptake inhibitor (fluoxetine) was employed.

6.2.7. Regulation of Activation of Phospho-Ser845 of the GluR1 Subunit of the AMPA Receptor by DARPP-32

In order to evaluate the involvement of DARPP-32 in the activity of serotonin, mice that lack DARPP-32 (DARPP-32 knockout (KO) mice) were used. In one set of experiments, striatal slices were prepared from normal mice (DARPP-32 wild-type) and DARPP-32 knockout mice and incubated with serotonin for 5 minutes. Experiments were then carried out to determine the levels of phospho-Ser845 of the GluR1 subunit of the AMPA (AMPA, α-amino-3-hydroxy-5-methyl-4-isoxazolepropionic acid) receptor. The phosphorylation state at this site, which is phosphorylated by PKA and de-phosphorylated by PP-1, has previously been shown to modulated AMPA currents (Roche et al. 1996. Neuron 16:1179-1188; Snyder et al. 2000. J. Neuroscience 20:4480-4488). As shown in Table 3, serotonin caused a significant induction of phospho-Ser845-GluR1 in DARPP-32 wild-type mice, but not in the knockout mice. These data indicate that a DARPP-32 modulated serotonergic intracellular signaling pathway (i.e., serotonin/DARPP-32/PP-1 signaling cascade) is critical for the serotonin-mediated regulation of the phospho-Ser845-GluR1 subunit of the AMPA receptor.

TABLE 3

| Ser845-GluR1 Levels | | |
|---|---|---|
| Group | DARPP-32 Wild-type | DARPP-32 Knockout |
| Control | 100(26.2) | 100(23.0) |
| Serotonin | 199(22.7)* | 111(14.9)# |

*Indicates that the value is significantly different from saline.
Indicates that the value is significantly different from DARPP-32 wild-type.

6.2.8. Involvement of DARPP-32 in the Regulation of C-FOS mRNA Expression by PCA and 5-HTP To evaluate the relevance of DARPP-32 in mediating actions of PCA and 5-HTP on gene transcription, DARPP-32 wild-type and knockout mice were injected systemically with PCA, 5-HTP, or fluoxetine, and the effects on c-fos mRNA expression were investigated.

Twenty minutes after the injections, the animals were killed by decapitation and their brains frozen at −80° C. Coronal sections were then made and processed for in situ hybridization experiments with a probe against c-fos mRNA. The expression of c-fos mRNA is widely used as a marker for the biochemical activity of neurons. Manipulations of the serotonergic system, by PCA (4 mg/kg) and 5-HTP (50 mg/kg+carbidopa 50 mg/kg), increased c-fos mRNA expression in several brain regions, including prefrontal cortex and striatum in DARPP-32 wild-type mice. The same treatments resulted in significantly less induction of c-fos mRNA in DARPP-32 knockout mice (see Table 4). As illustrated in FIG. 3, both PCA and 5-HTP induced a strong expression of c-fos mRNA throughout striatum and cerebral cortex of WT mice. This effect, which was quantitated in the periventricular region of striatum (FIG. 3B) and in the cingulate cortex (FIG. 3C), was strongly attenuated in DARPP-32 KO mice.

TABLE 4

| c-fos mRNA Levels in Striatum | | |
|---|---|---|
| Group | DARPP-32 Wild-type | DARPP-32 Knockout |
| Saline | 0.052(0.006) | 0.048(0.005) |
| PCA | 0.181(0.021)* | 0.084(0.010)#* |
| 5-HTP | 0.195(0.017)* | 0.092(0.009)#* |

*Indicates that the value is significantly different from saline.
Indicates that the value is significantly different from DARPP-32 wild-type.

6.2.9. 6-Hydrocydopamine (6-OHDA) Lesioning Studies

Further experiments were conducted that provide evidence that activation of a serotonergic intracellular signaling pathway and of DARPP-32 has applicability in the treatment of Parkinson's disease. In these experiment, rats were unilaterally (i.e. in one hemisphere) injected with 6-OHDA (6-hydroxydopamine; a dopaminergic neurotoxin) according to standard methods. The 6-OHDA is selectively taken up by dopaminergic neurons and kills the neurons. Such 6-OHDA-lesioned animals are considered an animal model of Parkinson's disease. The 6-OHDA-lesioned animals were sacrificed, striatal slices were prepared, as described hereinabove, from the non-lesioned (i.e., "normal") and the 6-OHDA-lesioned (i.e., "dopamine-depleted") hemispheres, and used for striatal slice experiments according to the methods described hereinabove. 5-HT or saline (control) was administered according to the methods described hereinabove. Administration of 5-HT was found to cause a similar increase in Thr34-DARPP-32 phosphorylation in both hemispheres (Table 5). The interpretation of these experiments is that 5-HT activates DARPP-32 phosphorylation via a mechanism that is largely independent of enhanced dopaminergic neurotransmission. Agents that enhance serotonergic neurotransmission, and that are stimulatory, can thus exert anti-Parkinsonian effects independent of dopamine, and can be used in the treatment of Parkinson's disease.

TABLE 5

| 6-Hydroxydopamine (6-OHDA) Lesioning Studies | | |
|---|---|---|
| Group | Hemisphere Treatment | Percent Phospho-Thr34 |
| Saline | Intact | 100(5.8) |
| Saline | 6-OHDA lesioned | 100(25.4) |
| 5-HT | Intact | 306(50.7) |
| 5-HT | 6-OHDA lesioned | 369(67.2)* |

*Indicates that the value is significantly different from saline.

6.2.10. Involvement of DARPP-32 in the Behavioral Effects of PCA and 5-HTP

To investigate the role of DARPP-32 in mediating behavioral actions exerted by an enhanced release of serotonin, the effects of PCA and 5-HTP on locomotor activity and stereotypic behaviors were examined in WT and DARPP-32 KO mice. PCA as well as 5-HTP caused a robust increase both in locomotor activity and stereotypic behavior in WT mice (FIG. 4). The actions on both of these behavioral parameters were abolished in DARPP-32 KO mice. The attenuated responsiveness of DARPP-32 KO mice to PCA and 5-HTP cannot be explained by a loss of ability of these mice to be hyperactive. In experiments in which drug-naive animals were exposed to the novel environment represented by the test cages, we found no difference in locomotor activity scores between WT (6,133±293 cm/20 min) and DARPP-32 KO (6,268±418 cm/20 min) mice.

6.3. Discussion

This example demonstrates that DARPP-32 activity is involved in the serotonergic response in the mice and provide an important link between in vitro effect data on phosphorylation of DARPP-32 and biological function of serotonin systems. This example also demonstrates that behavioral as well as biochemical effects induced by enhanced serotonergic neurotransmission are attenuated in DARPP-32 KO mice. This example further demonstrates an important role for DARPP-32 in mediating the actions of serotonin in vivo.

Serotonin caused an increased phosphorylation of DARPP-32 at Thr34 (the PKA site) and Ser137 (the CK-1 site) and a decreased phosphorylation at Thr75 (the Cdk5 site), in brain slices. The use of selective serotonin receptor agonists and antagonists, and other pharmacological reagents, including TTX, U-73122, and RpcAMPs, has enabled us to elucidate the underlying signaling pathways. The actions of serotonin in regulating DARPP-32 phosphorylation at Thr34 and Thr75 were mediated by means of activation of 5-HT4 and 5-HT6 receptors, whereas the regulation at Ser137 was mediated by means of 5-HT2 receptors. The three pathways appear to inhibit PP-1 through synergistic mechanisms (FIG. 5) and provide a model by which serotonin as well as compounds which increase serotonin transmission may produce their effects. These latter compounds include, in addition to PCA and 5-HTP, the selective serotonin reuptake inhibitor, fluoxetine, a widely used antidepressant agent. The pattern of DARPP-32 phosphorylation induced by elevated serotonergic neurotransmission is very similar to that induced by elevated dopaminergic neurotransmission (13). However, the serotonin-mediated regulation of DARPP-32 phosphorylation is largely independent of altered dopaminergic neurotransmission (Table 1).

Numerous psychoactive compounds act directly on both the serotonergic and dopaminergic systems. For example, cocaine inhibits the reuptake of both dopamine and serotonin from the synapse. It has recently been shown that the reinforcing properties of cocaine in the place preference test remain intact in dopamine transporter KO mice or serotonin transporter KO mice, but are severely impaired in mice that lack both transporters (19). These data imply that certain biochemical effects of cocaine can be mediated either by dopamine or serotonin. This example demonstrates that signaling through the DARPP-32 pathway is likely to be responsible for this redundancy. In support of the observation, the diminished responsiveness to the reinforcing properties of cocaine in the place preference test of the double transporter KO mice has been found to be mimicked by DARPP-32 KO mice (20).

Evidence that the effects of serotonin on DARPP-32 phosphorylation observed in vitro are of physiological relevance is demonstrated in the studies disclosed hereinabove in which we injected mice with PCA or 5-HTP and examined the effects on DARPP-32 phosphorylation in the striatum and prefrontal cortex. Both treatments led to a pattern of DARPP-32 phosphorylation that closely resembled that observed in slices in response to serotonin, namely increases at phospho-Thr34 DARPP-32 and phospho-Ser137 DARPP-32 and a decrease at phospho-Thr75 DARPP-32. It seemed possible that the effects of 5-HTP on DARPP-32 phosphorylation were attributable mainly to ectopically released serotonin produced in dopaminergic nerve terminals. However, the fact that PCA, which acts selectively on serotonergic nerve terminals, at the dose used, also had pronounced effects on DARPP-32 phosphorylation in the striatum and the prefrontal cortex, shows that an enhanced release of serotonin in these areas regulates DARPP-32 phosphorylation. The conclusion that DARPP-32 mediates the behavioral effects of serotonin is supported by experiments showing that 0.3 mg/kg of clozapine, a dose that antagonize responses by means of 5-HT2 and 5-HT6 receptors, counteracts the locomotor effects of PCA and 5-HTP. Strong evidence for an involvement of DARPP-32 in the biochemical and behavioral actions of serotonin under in vivo conditions came from studies in which we examined effects of PCA and 5-HTP in WT and DARPP-32 KO mice. An induction of c-fos mRNA was found throughout striatum and cerebral cortex in WT mice treated with PCA or 5-HTP. The ability of both PCA and 5-HTP to induce c-fos mRNA expression was strongly reduced in DARPP-32 KO mice. It is well known that the transcription of c-fos mRNA is negatively regulated by PP-1 (21). The involvement of DARPP-32 in PCA- and 5-HTP-mediated c-fos induction is owing, at least in part, to its ability to inhibit PP-1.

Previous work has implicated serotonin in the regulation of locomotion and exploratory behavior (23). Depletion of serotonin caused a long-term reduction in exploration (24), whereas local application of serotonin into nucleus accumbens caused an increase in locomotion (25) in rats. It is generally agreed that agents that increase the release of serotonin, such as PCA, 5-HTP, and 3,4-methylene-dioxymethamphetamine ("Ecstasy") increase locomotor activity (23, 26). To further investigate the functional relevance of DARPP-32 phosphorylation in the actions of PCA and 5-HTP, the effects of these drugs on locomotor activity and stereotypic behaviors were examined in WT and DARPP-32 KO mice. As expected, both PCA and 5-HTP increased locomotor activity and stereotypic behaviors in WT mice. Both of these responses were greatly attenuated in DARPP-32 KO mice.

These data considered together indicate that DARPP-32 phosphorylation is linked to serotonergic function in central nervous system tissues and serotonergic-induced anti-depressant drug activity. These data correlate the activity of CK1, Cdk5, AMPA receptor, PP-1, PP2C, PP2B and/or PP2A to biologically significant processes that are involved in anti-depressant drug activity and in regulation of neuronal function. Moreover, these data provide information on signaling molecules for targeting by therapeutic strategies for treatment of depression. Therefore, the signaling molecules targeted for therapeutic purposes in treatment of depression may include, but not be limited to CK1, Cdk5, AMPA receptor, PP-1, PP2C, PP2B and/or PP2A.

6.4. References

1. Steinbusch, H. W. (1981) Neuroscience 6, 557-618.
2. Lindvall, O. & Bjorklund, A. (1984) in Handbook of Chemical Neuroanatomy, eds. Bjorklund, A. & Hokfelt, T. (Elsevier, Amsterdam), pp. 55-122.

3. Bhat, R. V. & Baraban, J. M. (1993) J. Pharmacol. Exp. Ther. 267, 496-505.
4. Genova, L. M. & Hyman, S. E. (1998) Synapse 30, 71-78.
5. White, F. J., Hu, X. & Henry, D. J. (1993) J. Pharmacol. Exp. Ther. 266, 1075-1084.
6. Barnes, N. M. & Sharp, T. (1999) Neuropharmacology 38, 1083-1152.
7. Fienberg, A. A., Hiroi, N., Mermelstein, P. G., Song, W. J., Snyder, G. L., Nishi, A., Cheramy, A., O'Callaghan, J. P., Miller, D. B., Cole, D. G., el al. (1998) Science 281, 838-842.
8. Greengard, P., Allen, P. B. & Nairn, A. C. (1999) Neuron 23, 435-447.
9. Greengard, P. (2001) Science 294, 1024-1030.
10. Hemmings, H. C., Jr., Greengard, P., Tung, H. Y. L. & Cohen, P. (1984) Nature (London) 310, 503-505.
11. Lindskog, M., Svenningsson, P., Fredholm, B. B., Greengard, P. & Fisone, G. (1998) Neuroscience 88, 1005-1008.
12. Nishi, A., Snyder, G. L. & Greengard, P. (1997) J. Neurosci. 17, 8147-8155.
13. Nishi, A., Bibb, J. A., Snyder, G. L., Higashi, H., Nairn, A. C. & Greengard, P. (2000) Proc. Natl. Acad. Sci. USA 97, 12840-12845.
14. Bibb, J. A., Snyder, G. L., Nishi, A., Yan, Z., Meijer, L., Fienberg, A. A., Tsai, L. H., Kwon, Y. T., Girault, J. A., Czernik, A. J., et al. (1999) Nature (London) 402, 669-671.
15. Desdouits, F. Siciliano, J. C. Greengard, P. & Girault, J.-A. (1995) Proc. Natl. Acad. Sci. USA 92, 2682-2685.
17. Leysen, J. E. (2000) in Atypical Antipsychotics, eds. Ellenbroek, B. A. & Cools, A. R. (Birkha user, Basel), pp. 57-81.
18. Rozas, G., Liste, I., Guerra, M. J. & Labandeira-Garcia, J. L. (1998) Neurosci. Lett. 245, 151-154.
19. Sora, I., Hall. S., Andrews, A. M., Itokawa, M., Li, X.-F., Wei, H.-B., Wichems, C., Lesch, K.-P., Murphy, D. L. & Uhl, G. R. (2001) Proc. Natl. Acad. Sci. USA 98, 5300-5305.
20. Zachariou, V., Benoit-Marandl, M., Allen, P. B., Ingrassia, P., Fienberg, A. A., Gonon, F., Greengard, P. & Picciotto, M. (2002) Biol. Psychiatry, in press.
21. Hagiwara, M., Alberts, A., Brindle, P., Meinkoth, J., Feramisco, J., Deng, T., Karin, M., Shenolikar, S. & Montminy, M. (1992) Cell 70, 105-113.
22. Liu, F.-C. & Graybiel, A. M. (1996) Neuron 17, 1133-1144.
23. Geyer, M. A. (1996) Behav. Brain Res. 73, 31-36.
24. Lipska, B. K., Jaskiw, G. E., Arya, A. & Weinberger, D. R. (1992) Pharmacol. Biochem. Behav. 43, 1247-1252.
25. Sasaki-Adams, D. M. & Kelley, A. E. (2001) Neuropsychopharmacology 25, 440-452.
26. Modigh, K. (1972) Psychopharmacology 23, 48-54.
27. Liu, F., Ma, X. H., Ule, J., Bibb, J. A., Nishi, A., DeMaggio, A. J., Yan, Z., Nairn, A. C. & Greengard, P. (2001) Proc. Natl. Acad. Sci. USA 98, 11062-11068.

7. EXAMPLE 2

Involvement of Striatal and Extrastriatal DARPP-32 in Biochemical and Behavioral Effects of Fluoxetine This example discloses the effects of acute and chronic administration of fluoxetine on the level and phosphorylation state of DARPP-32 at multiple sites in prefrontal cortex, hippocampus, and striatum. By using DARPP-32 knockout (KO) mice, the involvement of DARPP-32 in mediating the beneficial effects of fluoxetine and in regulating AMPA (AMPA, -amino-3-hydroxy-5-methyl-4-isoxazolepropionic acid) receptor phosphorylation was examined. A tail-suspension test was used as an experimental model to predict antidepressant efficacy.

7.1. Materials and Methods

7.1.1. Whole Animal Studies

In experiments examining acute effects of fluoxetine, adult male C57/Bl6 mice were given an i.p. injection with saline or fluoxetine (5, 10, or 20 mg/kg) and killed 15-min postinjection by focused microwave irradiation (4.5 5 kW for 1.4 sec), by using a small animal microwave (Muromachi Kikai, Tokyo, Japan). In experiments examining chronic effects of fluoxetine, adult male C57/Bl6, wild-type (WT), or DARPP-32 KO mice (16) were injected i.p. with saline or fluoxetine (10 mg/kg) for 19 days and then challenged with saline or fluoxetine (5 or 10 mg/kg) and killed 15-min postinjection. In all experiments, hippocampi, prefrontal cortices, and striata were rapidly dissected out and stored at −80° C. until assayed.

7.1.2. Preparation and Treatment of Slices from Hippocampus, Prefrontal Cortex, and Striatum Slices (300-m) were prepared from adult male C57/Bl6, WT, or DARPP-32 KO mice as described (17). The slices were preincubated in Krebs buffer at 30 C. under constant oxygenation (95% O2 5% CO2) for 60 min, with a change of buffer after 30 min. In all experiments with serotonin, the slices were pretreated with fluoxetine (10 M) for 2 min, and then serotonin (100 M) was added for an additional 2 min (for phospho-Thr-34 and phospho-Ser-137 DARPP-32) or 10 min (for phospho-Thr-75 DARPP-32 and phospho-Ser-831 and phospho-Ser-845 GluR1). Fluoxetine alone had no effect on DARPP-32 phosphorylation under any of the conditions tested. After drug treatment, the buffer was removed and the slices were rapidly frozen on dry ice and stored at −80 C until immunoblotted.

7.1.3. Immunoblotting

Frozen tissue samples from the in vitro and in vivo experiments were sonicated in 1% SDS and boiled for 10 min. Small aliquots of the homogenate were retained for protein determination by the bicinchoninic acid protein assay method (Pierce). Equal amounts of protein were processed by using 10% acrylamide gels as described (17). Immunoblotting was carried out with phosphorylation-state-specific antibodies against phospho-Thr-34 DARPP-32 (18), phospho-Thr-75 DARPP-32 (9), phospho-Ser-137 DARPP-32 (19), phospho-Ser-831 GluR1 (Upstate Biotechnology, Lake Placid, N.Y.), phospho-Ser-845 GluR1 (Upstate Biotechnology), or antibodies that are not phosphorylation-state-specific against total DARPP-32 (20) and total GluR1 (Upstate Biotechnology). Antibody binding was detected by enhanced chemiluminescence (ECL; Amersham Pharmacia) and quantified by densitometry, using National Institutes of Health IMAGE 1.61 software. Data on protein phosphorylation are expressed as percentage of control.

7.1.4. In situ Hybridization

WT and DARPP-32 KO mice were injected i.p. with saline or fluoxetine (10 mg/kg) for 19 days and killed 20 min after the last injection by decapitation. Brains were rapidly dissected out and frozen at −80° C. Cryostat sections (12-µm) were prepared and hybridized with [α-$^{35}$S]UTP-labeled riboprobes prepared by in vitro transcription from cDNA clones corresponding to full-length clones of DARPP-32 or inhibitor-1 as described (21). After hybridization, the sections were exposed to Biomax MR film (Kodak) for 2 14 days and analyzed with a Microcomputer Imaging Device system (M4, Imaging Research, St. Catherine's, ON, Canada).

7.1.5. Tail-Suspension Test

Mice were injected i.p. with saline or fluoxetine (5 or 10 mg/kg) 30 min before the tail-suspension test trial. Mice were suspended by their tails 80 cm above the floor by having their tails secured to the edge of a platform with adhesive tape placed 1 cm from the tip of the tail. The trial was conducted for a period of 5 min, during which the duration of immobility was recorded with the program PORSOLT (Infallible Software, Rockville, Md.). Mice were considered immobile when they hung passively and motionless (14).

7.2. Results

7.2.1. Regulation of DARPP-32 Phosphorylation in Vivo by Acute Treatment with Fluoxetine Mice were injected i.p. with saline or fluoxetine (5, 10, and 20 mg/kg) and killed 15 min later by focused microwave irradiation. The results shown in FIG. 6 demonstrate that fluoxetine caused an increased phosphorylation of DARPP-32 at Thr-34, the PKA site, and a decreased phosphorylation at Thr-75, the cyclin dependent kinase 5 (Cdk5) site, in hippocampus, frontal cortex, and striatum (FIG. 6). Because of a low signal in extrastriatal areas, the level of phosphorylation of DARPP-32 at Ser-137, the casein kinase-1 site, could be accurately assayed only in striatum. In this region, fluoxetine increased phosphorylation at Ser-137.

7.2.2. Regulation of DARPP-32 Phosphorylation in Vivo by Chronic Treatment with Fluoxetine The antidepressant actions of fluoxetine characteristically require 2 3 weeks to be manifested. To examine the effects of chronic administration of fluoxetine on DARPP-32 phosphorylation, mice were treated with saline or fluoxetine (10 mg/kg, i.p.) once daily for 19 days and then challenged with a single i.p. injection of saline or fluoxetine at 5 or 10 mg/kg and killed 15-min postinjection. Mice chronically treated with saline and challenged with fluoxetine exhibited patterns of DARPP-32 phosphorylation (FIG. 7 Upper) similar to those obtained in the acute dose response experiments (FIG. 6).

In mice chronically treated with fluoxetine, there was an increase in total DARPP-32 protein in hippocampus and frontal cortex, but not in striatum (see Section 7.2.3, Regulation of DARPP-32 mRNA and Protein Levels by Chronic Treatment with Fluoxetine). After normalization for these changes in the total levels of DARPP-32, there were no differences in the fraction of DARPP-32 phosphorylated at Thr-34, Thr-75, or Ser-137 between mice chronically treated with saline and challenged with saline and those chronically treated with fluoxetine and challenged with saline. A challenge with fluoxetine increased DARPP-32 phosphorylation at Thr-34 and decreased DARPP-32 phosphorylation at Thr-75 (FIG. 7 Lower) in mice chronically treated with fluoxetine to an extent similar to that seen in mice chronically treated with saline (FIG. 7 Upper) in all three regions examined. In contrast, the ability of a challenge with 10 mg/kg of fluoxetine to increase phosphorylation at Ser-137 in striatum (FIG. 7 Lower) was abolished in mice chronically treated with fluoxetine.

7.2.3. Regulation of DARPP-32 mRNA and Protein Levels by Chronic Treatment with Fluoxetine Mice treated chronically with fluoxetine (10 mg/kg, i.p.) exhibited increased levels of total DARPP-32 protein in prefrontal cortex (123 3%) and hippocampus (121 4%), but not striatum (102 4%), when compared with mice treated chronically with saline. The changes in the total levels of DARPP-32 protein were not paralleled by changes in the total levels of inhibitor-1 protein (102 2%, 98 3%, and 97 3%, for the three regions, respectively), a closely related homologue of DARPP-32. To determine whether effects of chronic fluoxetine on DARPP-32 protein levels in hippocampus and prefrontal cortex occurred at the transcriptional level, in situ hybridization experiments were carried out to study the effects of chronic administration (once daily for 19 days) of saline or fluoxetine (10 mg/kg, i.p.) on DARPP-32 mRNA levels. As illustrated in FIG. 8, chronic treatment with fluoxetine increased DARPP-32 mRNA expression in hippocampus and frontal cortex, but not in striatum (FIG. 8 Left). Chronic treatment with fluoxetine had no effects on inhibitor-1 mRNA expression in any of the examined regions (FIG. 8 Right).

7.2.4. Regulation by Serotonin of DARPP-32 Phosphorylation in Slices

To examine whether the effects of fluoxetine on DARPP-32 phosphorylation could be attributed to an action of serotonin on DARPP-32-containing neurons, slices were incubated with serotonin (100 M). The results presented in FIG. 9 demonstrate that serotonin increased DARPP-32 phosphorylation at Thr-34 (FIG. 9 Upper) and decreased DARPP-32 phosphorylation at Thr-75 (FIG. 9 Lower), in slices prepared from hippocampus, prefrontal cortex, and striatum (FIG. 9). Serotonin also increased DARPP-32 phosphorylation at Ser-137 in striatum (see Section 6).

7.2.5. Regulation by Serotonin of AMPA Receptor Phosphorylation in Slices Prepared from WT and DARPP-32 KO Mice DARPP-32 regulates phosphorylation of AMPA receptors and increases AMPA currents in striatal neurons (12, 13). Moreover, positive allosteric modulators of AMPA receptors have beneficial effects in animal models of depression (14, 15).We therefore investigated, using WT and DARPP-32 KO mice, whether serotonin can regulate the phosphorylation state of the GluR1 subunit of the AMPA receptor at two different phosphorylation sites known to affect the functional properties of AMPA receptors, namely Ser-831 GluR1, a PKC/calmodulin-dependent kinase II (CamKII) site, and Ser-845-GluR1, a PKA site. The results shown in FIG. 10 demonstrate that serotonin (100 µM) increased the phosphorylation at Ser-831 GluR1 as well as at Ser-845 GluR1 in slices from hippocampus, frontal cortex, and striatum in WT mice. The increased phosphorylation at Ser-845 GluR1 in WT mice was significantly reduced in slices prepared from DARPP-32 KO mice (FIG. 10), showing that the DARPP-32/PP-1 intracellular signaling pathway is involved in the serotonin mediated regulation of GluR1 phosphorylation at this site. The increased phosphorylation at Ser-831 GluR1 in WT mice was significantly reduced in striatal slices, but not in hippocampal or cortical slices, prepared from DARPP-32 KO mice (FIG. 10); the striatal data indicate that the DARPP-32/PP-1 intracellular signaling pathway may be involved in the serotonin-mediated regulation of phosphorylation at Ser-831 GluR1.

7.2.6. Regulation of AMPA Receptor Phosphorylation by Chronic Treatment with Saline or Fluoxetine in WT and DARPP-32 KO Mice WT mice that had been treated chronically with saline and challenged with fluoxetine exhibited an increased phosphorylation state at Ser-831 GluR1 and Ser-845 GluR1 in all three brain regions examined (Table 6).

TABLE 6

Regulation by chronic treatment with saline or fluoxetine (Fluo) of AMPA receptor phosphorylation in vivo

| Chronic treatment | Challenge | Ser-831-GluR1 | | Ser-845-GluR1 | |
|---|---|---|---|---|---|
| | | WT | D32 KO | WT | D32 KO |
| Hippocampus | | | | | |
| Saline | Saline | 100(2.0) | 97(5.9) | 100(0.9) | 104(2.4) |
| Saline | Fluo 5 mg/kg | 111(8.0) | 102(6.7) | 133(2.5)* | 115(4.2)# |
| Saline | Fluo 10 mg/kg | 127(6.1)* | 110(4.8)# | 143(7.8)** | 114(3.9)# |
| Fluo | Saline | 96(3.4) | 98(3.7) | 96(3.8) | 97(5.3) |
| Fluo | Fluo 5 mg/kg | 98(4.6) | 94(3.3) | 136(5.2)§ | 122(4.4) |
| Fluo | Fluo 10 mg/kg | 107(4.0)† | 105(5.5) | 133(5.9)§ | 110(5.2)# |
| Prefrontal cortex | | | | | |
| Saline | Saline | 100(5.2) | 88(10.2) | 100(2.2) | 91(3.4) |
| Saline | Fluo 5 mg/kg | 94(3.4) | 90(5.0) | 136(6.6)* | 118(4.1)# |
| Saline | Fluo 10 mg/kg | 115(2.8)* | 107(4.3) | 133(5.8)* | 110(9.7)# |
| Fluo | Saline | 90(10.0) | 88(4.7) | 88(8.8) | 84(4.5) |
| Fluo | Fluo 5 mg/kg | 98(6.7) | 88(6.6) | 128(8.6)§ | 107(6.6)# |
| Fluo | Fluo 10 mg/kg | 99(8.0)† | 94(4.4) | 129(8.2)§ | 109(9.4)# |
| Striatum | | | | | |
| Saline | Saline | 100(5.7) | 88(8.0) | 100(2.3) | 104(8.0) |
| Saline | Fluo 5 mg/kg | 123(1.1)* | 115(5.0) | 141(7.4)* | 116(9.1)# |
| Saline | Fluo 10 mg/kg | 135(4.9)* | 126(10.2) | 159(10.5)** | 128(4.9)# |
| Fluo | Saline | 97(8.2) | 86(15.6) | 111(8.1) | 109(7.9) |
| Fluo | Fluo 5 mg/kg | 110(2.8) | 112(4.8) | 142(7.9)§ | 123(4.0)# |
| Fluo | Fluo 10 mg/kg | 111(8.7)† | 109(5.2) | 160(7.4)§§ | 135(6.6)# |

Data are shown for phospho-Ser-831-GluR1 and Phospho-Ser-845-GluR1 in WT and DARPP-32 KO (D32 KO) mice treated for 19 days with saline or fluoxetine (10 mg/kg) and then challenged with silane or fluoxetine (5 or 10 mg/kg) and killed 15-min postinjection. Data represent means ±SEM for four to twelve mice per group.
*$P < 0.05$,
**$P < 0.01$ compared with saline/saline-treated mice; §, $P < 0.05$, §§, $P <$ compared with fluxetine/silane-treated WT mice
†$P < 0.05$ compared with coresponding saline/fluoxetine-treated WT mice;
$P < 0.05$ compared with corresponding WT mice, one-way ANOVA followed by Dunnett's test.

WT mice chronically treated with fluoxetine and challenged with fluoxetine exhibited higher levels of phosphorylation at Ser-845 GluR1 in all three brain regions than did WT mice chronically treated with fluoxetine and challenged with saline. In contrast, the ability of a challenge with fluoxetine to increase phosphorylation at Ser-831 GluR1 was abolished in WT mice chronically treated with fluoxetine. We also compared fluoxetine-induced phosphorylation of the AMPA receptor in WT and DARPP-32 KO mice to evaluate the possible involvement of DARPP-32 in mediating the effects of fluoxetine. Fluoxetine (5 and 10 mg/kg) was significantly less efficient in increasing phosphorylation at Ser-845 GluR1 in DARPP-32 KO mice than in WT mice (Table 6), regardless of whether the mice had received chronic treatment with saline or fluoxetine. The fluoxetine-mediated increase in phospho-Ser-831 GluR1 was significantly lower in hippocampus, but not in cortex or striatum, from DARPP-32 KO mice (Table 6, Hippocampus).

7.2.7. Involvement of DARPP-32 in Fluoxetine-Mediated Immobility in the Tail-Suspension Test for Antidepressant Efficacy Learned helplessness models, in which experimental animals are exposed to inescapable aversive situations, e.g., the tail-suspension test, are of utility for predicting antidepressant efficacy. During these tests, mice show alternate periods of agitation and immobility (23). It is well established that acute treatment with various antidepressant drugs reduces immobility in these tests. In particular, agents that selectively inhibit serotonin reuptake, including fluoxetine, invariably appear to be efficacious in the tail-suspension test (24). To evaluate the possible involvement of DARPP-32 in fluoxetine mediated antidepressant-like effects in the tail-suspension test, WT and DARPP-32 KO mice were injected with saline or fluoxetine (5 or 10 mg/kg) 30 min before the trial. Fluoxetine decreased immobility in WT animals (FIG. 11). This effect was strongly attenuated in DARPP-32 KO mice (FIG. 11). Nonspecific increases in activity could not account for the positive effect of fluoxetine in WT mice, because locomotion was not significantly affected by fluoxetine at the doses examined.

7.3. Discussion

This example demonstrates that fluoxetine regulates phosphorylation of DARPP-32 at multiple sites and that DARPP-32 mediates biochemical and behavioral actions of fluoxetine. Functional neuroimaging studies have shown that there is an altered activity in prefrontal cortex, hippocampus, amygdala, and striatum in depressed individuals that is, at least partly, reversible by antidepressant regimens (2). Moreover, adaptations in the cAMP/PKA pathway, together with morphological and electrophysiological changes, have been described in prefrontal cortex, hippocampus, amygdala, and striatum after administration of fluoxetine and other antidepressants in laboratory animals (1, 2). These regions receive a moderate to high serotonergic innervation (25) and contain DARPP-32 (6). In the present study, the ability of fluoxetine to regulate DARPP-32 phosphorylation was assessed in prefrontal cortex, hippocampus, and striatum.

In the present studies, it was found that acute administration of fluoxetine to whole animals or application of serotonin to slices, increased phosphorylation of DARPP-32 at Thr-34, decreased phosphorylation at Thr-75, and increased phosphorylation at Ser-137. The previous example (Section 6) demonstrates that the following cascades of the serotonergic intracellular signaling pathway account for these three effects: (i) activation of 5-HT4 and 5-HT6 receptors increased cAMP activation of PKA phosphorylation of Thr-34; (ii) activation of 5-HT4 and 5-HT6 receptors increased cAMP activation of PKA activation of protein phosphatase-2A (PP-2A) dephosphorylation of Thr-75; (iii) activation of 5-HT2 receptors increased activation of PLC, which in turn increased calcium activation of CK1 dependent phosphorylation of Ser-137. As is also discussed in the previous example, the changes at these three phosphorylation sites work synergistically, each contributing to the inhibition of PP-1. Moreover, these three cascades also can account for the observations that the ability of fluoxetine to regulate DARPP-32 phosphorylation at Thr-34 and Thr-75, but not at Ser-137, is preserved in mice chronically treated with this compound. Thus, there is evidence that serotonin-mediated responses via the cAMP/PKA pathway persist (1, 27), but that responses via the PLC pathway are reduced (27 30), after prolonged fluoxetine treatment.

Chronic treatment with fluoxetine caused a significant increase in the total levels of DARPP-32 protein and mRNA in prefrontal cortex and hippocampus, but not striatum. These data extend previous observations that chronic treatment with the tricyclic antidepressant, imipramine, or the mood-stabilizer, lithium, increases the level of total DARPP-32 protein in the rat frontal cortex (31). The mechanisms underlying the regulation of DARPP-32 levels in frontal cortex and hippocampus remain to be determined. However, brain-derived neurotrophic factor (BDNF) may be involved, because it has been shown that chronic treatment with several different antidepressants, including fluoxetine, increases the levels of BDNF in frontal cortex and hippocampus in experimental animals (32), and that the levels of DARPP-32 mRNA and protein are significantly reduced in BDNF KO mice (33).

Without wishing to be bound by any particular theory, these data indicate that phospho-Thr-34 DARPP-32 increases the phosphorylation state and efficacy of several ion channels and ionotropic receptors, such as AMPA receptors (10, 11). Activation of PKA in hippocampal (35) or striatal (12) neurons increases AMPA receptor currents and AMPA receptor-mediated synaptic plasticity. Phosphorylation by PKA at Ser-845 GluR1 is required for PKA-mediated potentiation of peak current carried by homomeric GluR1 channels (36). AMPA receptors also can be regulated by phosphorylation of Ser-831 GluR1 after activation of calcium/calmodulin-dependent kinase II (CaMKII) or protein kinase C (PKC) leading to potentiation of AMPA currents in hippocampal neurons (37).

LY392098 and LY404187, two allosteric potentiators of AMPA receptor function, are known to have robust antidepressant-like actions in two tests of "learned helplessness," the forced-swim test and the tail suspension test (14, 15). Based on these findings, we examined the effects of fluoxetine on AMPA receptor phosphorylation. It was found that acute administration of fluoxetine increased the phosphorylation of both Ser-831 GluR1 and Ser-845 GluR1 in frontal cortex, hippocampus, and striatum. The fluoxetine-mediated regulation at Ser-845 GluR1 was strongly and consistently attenuated in DARPP-32 KO mice. After chronic administration of fluoxetine, the ability of a challenge with fluoxetine to induce phosphorylation at Ser-845 GluR1, in a DARPP-32-dependent manner, was preserved. In contrast, the fluoxetine-mediated phosphorylation at Ser-831 GluR1 was found only in mice chronically treated with saline and not in mice chronically treated with fluoxetine. As a consequence, the ratio of the phosphorylation state between Ser-845 GluR1 and Ser-831 GluR1 was increased. Such a change may be associated with altered synaptic plasticity (38) and may underlie an adaptive response relevant to the delayed onset of the antidepressant action of fluoxetine.

To evaluate the behavioral relevance of the biochemical actions of fluoxetine on DARPP-32 phosphorylation, the effect of fluoxetine in the tail-suspension test was evaluated in WT and DARPP-32 KO mice. This test is among the most commonly used procedures to detect clinically effective antidepressant agents because of its high degree of predictive validity (23, 24). Several selective serotonin reuptake inhibitors, including fluoxetine, reduce immobility in this test. Indeed, in the present study, fluoxetine decreased immobility in WT mice. Nonspecific activation could not account for this effect, because fluoxetine did not affect locomotion in WT mice. Interestingly, the effect of fluoxetine in the tail-suspension test was significantly attenuated in DARPP-32 KO mice. The suppression in DARPP-32 KO mice of the fluoxetine-induced reduction in immobility time in the tail-suspension test strongly suggests that DARPP-32 participates in the antidepressant actions of fluoxetine. In conclusion, the data indicating that fluoxetine regulates the phosphorylation state of DARPP-32 and AMPA receptors, that DARPP-32 is involved in mediating the effect of fluoxetine on AMPA receptor phosphorylation and in the tail-suspension test, and that AMPA receptor potentiators mimic antidepressant agents in this behavioral test, suggest that a signaling pathway involving a DARPP-32-induced increase in AMPA receptor phosphorylation and conductance may play an important role in mediating the antidepressant actions of fluoxetine.

7.4. References

1. Duman, R. S., Heninger, G. R. & Nestler, E. J. (1997) Arch. Gen. Psychiatry 54, 597-606.
2. Manji, H. K., Drevets, W. C. & Charney, D. S. (2001) Nat. Med. 7, 541-547.
3. Horowski, R. & Sastre-Y-Hernandez, M. (1985) Curr. Ther. Res. 38, 23-29.
4. Fleischhacker, W. W., Hinterhuber, H., Bauer, H., Pflug, B., Berner, P., Simhandl, C., Wilf, R., Gerlach, W., Jaklitsch, H., Sastre-Y-Hemandez, M., et al. (1992) Neuropsychobiology 26, 59-64.
5. Walaas, S. I., Aswad, D. W. & Greengard, P. (1983) Nature (London) 301, 69-71.
6. Ouimet, C. C., Miller, P. E., Hemmings, H. C., Jr., Walaas, S. I. & Greengard, P. (1984) J. Neurosci. 4, 114-124.
7. Hemmings, H. C., Jr., Greengard, P., Tung, H. Y. L. & Cohen, P. (1984) Nature (London) 310, 503-505.
8. Desdouits, F., Siciliano, J. C., Greengard, P. & Girault, J.-A. (1995) Proc. Natl. Acad. Sci. USA 92, 2682-2685.
9. Bibb, J. A., Snyder, G. L., Nishi, A., Yan, Z., Meijer, L., Fienberg, A. A., Tsai, L. H., Kwon, Y. T., Girault, J. A., Czemik, A. J., et al. (1999) Nature (London) 402, 669-671.
10. Greengard, P., Allen, P. B. & Nairn, A. C. (1999) Neuron 23, 435-447.
11. Greengard, P. (2001) Science 294, 1024-1030.
12. Yan, Z., Hsien-Wilson, L., Feng, J., Tomizawa, K., Allen, P. B., Fienberg, A. A., Nairn, A. C. & Greengard, P. (1999) Nat. Neurosci. 2, 13-17.
13. Snyder, G. L., Allen, P. B., Fienberg, A. A., Valle, C. G., Huganir, R. L., Nairn, A. C. & Greengard, P. (2000) J. Neurosci. 20, 4480-4488.
14. Li, X., Tizzano, J. P., Griffey, K., Clay, M., Lindstrom, T. & Skolnick, P. (2001) Neuropharmacology 40, 1028-1033.

15. Skolnick, P. Legutko, B., Li, X.&Bymaster, F. P. (2001) Pharmacol. Res. 43, 411-422.
16. Fienberg, A. A., Hiroi, N., Mermelstein, P. G., Song, W. J., Snyder, G. L., Nishi, A., Cheramy, A., O'Callaghan, J. P., Miller, D. B., Cole, D. G., et al. (1998) Science 281, 838-842.
17. Nishi, A., Snyder, G. L. & Greengard, P. (1997) J. Neurosci. 17, 8147-8155.
18. Snyder, G. L., Girault, J. A., Chen, J. Y. C., Czernik, A. J., Kebabian, J. W., Nathanson, J. A. & Greengard, P. (1992) J. Neurosci. 12, 3071-3083.
19. Liu, F., Ma, X. H., Ule, J., Bibb, J. A., Nishi, A., DeMaggio, A. J., Yan, Z., Nairn, A. C. & Greengard, P. (2001) Proc. Natl. Acad. Sci. USA 98, 11062-11068.
20. Hemmings, H. C., Jr. & Greengard, P. (1986) J. Neurosci. 6, 1469-1481.
21. LeMoine, C. & Bloch, B. (1995) J. Comp. Neurol. 355, 418-426.
23. Steru, L., Chermat, R., Thierry, B. & Simon, P. (1985) Psychopharmacology 85, 367-370.
24. Porsolt, R. D. & Lenegre, A. (1992) in Experimental Approaches to Anxiety and Depression, eds. Elliott, J., Heal, D. J. & Marsden, C. A. (Wiley, London), pp.73-85.
25. Steinbusch, H. W. (1981) Neuroscience 6, 557-618.
26. Barnes, N. M. & Sharp, T. (1999) Neuropharmacology 38, 1083-1152.
27. Beasley, C. M., Masica, D. N. & Potvin, J. H. (1992) Psychopharmacology 107, 1-10.
28. Peroutka, S. L. & Snyder, S. H. (1980) Science 21, 88-90.
29. Sanders-Bush, E., Breeding, M., Knoth, K. & Tsutsumi, M. (1989) Psychopharmacology 99, 64-69.
30. Bristow, L. J., O'Connor, D., Watts, R., Duxon, M. S. & Hutson, P. H. (2000) Neuropharmacology 39, 1222-1236.
31. Guitart, X. & Nestler, E. J. (1992) J. Neurochem. 59, 1164-1167.
32. Nibuya, M., Morinobu, S. & Duman, R. S. (1995) J. Neurosci. 15, 7539-7547.
33. Ivkovic, S., Polonskaia, O., Farinas, I.&Ehrlich, M. (1999) Neuroscience 79, 509-516.
34. Siucack, J. A., Lewis, D. R., Wiegand, S. J. & Lindsay, R. M. (1997) Pharmacol. Biochem. Behav. 56, 131-137.
35. Greengard, P., Jen, J., Nairn, A. C. & Stevens, C. F. (1991) Science 253, 1135-1138.
36. Roche, K. W., O'Brien, R. J., Mammen, A. L., Bernhardt, J. & Huganir, R. L. (1996) Neuron 16, 1179-1188.
37. Barria, A., Muller, D., Derkach, V., Griffith, L. C. & Soderling, T. R. (1997) Science 276, 2042-2045.
38. Lee, H. K., Barbarosie, M., Kameyama, K., Bear, M. F. & Huganir, R. L. (2000) Nature (London) 405, 955-959.

8. EXAMPLE 3

Characterization of Protein Phosphatase PP2C Isoforms from Rat Brain

Protein phosphatase 2C (PP2C) is a major Ser/Thr phosphatase expressed in brain. This example exemplifies the cloning of the alpha ("a" or "α"), beta ("b" or "β"), gamma ("g" or "γ") and delta ("d" or "δ") isoforms of PP2C from striatum. Recombinant PP2C isoforms were expressed in vitro, and their distribution in the brain, ion specificity, and phosphatase activity towards phospho-Ser137 residue of DARPP 32 were compared. The data indicate that three of the isoforms are involved in dopamine- and glutamate-regulated signaling in the brain and that PP2Ca and g are predominant isoforms, highly expressed in cortex, hippocampus, cerebellum and striatum, whereas PP2Cb and d isoforms exhibited low to moderate expression in cerebral cortex and striatum. Recombinant PP2Ca, b, and g isoforms dephosphorylated DARPP-32 at Ser137 with Km values of 13, 25, and 7 mM respectively. In contrast, PP2Cd did not dephosphorylate DARPP-32.

8.1. Materials and Methods

8.1.1. Materials p-Nitrophenylphosphate (pNPP) was obtained from Sigma. CK1 was obtained from New England BioLabs. Recombinant DARPP-32 was purified and phosphorylated in vitro at Ser137 by CK1 using [g-$^{32}$P]ATP (stoichiometry of 1 mol/mol ) as previously described (Desdouits et al., 1998).

8.1.2. Cloning and Expression of Recombinant PP2C Isoforms

Full-length cDNAs for PP2Ca, b, g, and d isoforms, PP2B, and neurite extension-regulated protein phosphatase (NERPP) were amplified with Pfu polymerase from a library that was a mixture of rat striatal oligo-dT- and random-primed cDNA (a gift from Dr. Zhen Yan, SUNY Buffalo) using the following primers:

```
PP2Ca forward: 5'-GCGTCGACGATGGGAGCATTTTTAGACAAG-3';      (SEQ ID NO: 7)

PP2Ca reverse: 5'-TATTCATGCGGCCGCTTACCACATATCATCAGTTG-3'; (SEQ ID NO: 8)

PP2Cb forward: 5'-GCGTCGTCGACGATGGGTGCATTTTTGGATAA-3';    (SEQ ID NO: 9)

PP2Cb reverse: 5'-TATTCATGCGGCCGCTTATAAGGCTACCAATGAGTC-3'; (SEQ ID NO: 10)

PP2Cg forward: 5'-ACGCGTCGACAAATGGGTGCCTACCTCTCTCAGCC-3'; (SEQ ID NO: 11)

PP2Cg reverse: 5'-ATAAGAATGCGGCCGCCTGCTAGTCCCGCTTGGCCTTCTT-3'; (SEQ ID NO: 12)

PP2Cd forward: 5'-GCGTCGACGATGGACCTATTCGGGGACTTG-3';      (SEQ ID NO: 13)

PP2Cd reverse: 5'-TATTCATGCGGCCGCGTGTCCTATCCTCACCACC-3';  (SEQ ID NO: 14)

PP2B forward:  5'-GCGTCGACGATGGCCGCCCCGGAGCCGGC-3';       (SEQ ID NO: 15)

PP2B reverse:  5'-TATTCATGCGGCCGCTCACTTGTTCCTGATGACCTC-3'; (SEQ ID NO: 16)
```

```
NERPP forward:  5'-GCGTCGACGATGGGGAAGAGCACACACAATGAAG-3'; and    (SEQ ID NO: 17)

NERPP REVERSE:  5'-TATTCATGCGGCCGCTCATGACAGCTTGTTTCCATGTAT-3'.   (SEQ ID NO: 18)
```

The protocol for amplification included 2 cycles of denaturation at 94° C. for 1 min, annealing at 55° C. for 1 min, and elongation at 72° C. for 1 min, followed by 25 cycles of denaturation at 94° C. for 1 min, annealing at 60° C. for 1 min, and elongation at 72° C. for 1 min. The resulting PCR fragments were separated in 1% agarose gel. DNA bands of expected sizes of 1200-1600 bp were extracted from the gel and cloned into NotI-SalI sites of the pET28a expression vector (Novagene). Cloned cDNA nucleotide sequences were verified by direct sequencing of at least two independently produced clones.

*Escherichia coli* BL21(DE3) cells were transformed with the obtained DNA constructs and grown in 1 l of LB medium (containing 300 mg/ml kanamycin) at 37° C. At an OD600 of 0.5, protein expression was induced by addition of 1 mM isopropyl b-thiogalactopyranoside (IPTG), and cultures were incubated for 4 h. Cells were harvested by centrifugation, resuspended in 10 ml of ice-cold lysis buffer containing 20 mM Tris-HCl, pH 8.0, 30 mM imidazole, 300 mM NaCl, and EDTA-free protease inhibitor cocktail (Hoffman-La Roche). Cells were lysed using a French press and cell debris was removed by centrifugation at 30,000 g for 40 min. The supernatant was incubated with 2 ml of Ni-NTA-agarose (Qiagen) for 30 min at 4 C. Recombinant proteins were eluted with lysis buffer containing 400 mM imidazole, dialyzed against 25 mM Tris-HCl, pH 7.5, and stored at –80° C.

8.1.3. In Situ Hybridization $^{35}$S-labeled cRNA probes were prepared by in vitro transcription from cDNA clones corresponding to the following fragments of the various PP2C genes: PP2Ca -452 bp N-terminal fragment; PP2Cb and PP2Cg-310 bp C-terminal fragments starting from the HindIII site; PP2Cd-300 bp N-terminal fragment. Transcription reactions were performed using 50 ng of linearized plasmid, $^{35}$S-UTP (>1000 Ci/mmol, NEN Life Science) and either SP6 or T7 RNA polymerases as described (LeMoine et al., 1995). After alkaline hydrolysis to obtain approximately 250 bp cRNA fragments, the $^{35}$S-labeled probes were purified on G50-Sephadex and precipitated with 3 M sodium acetate, pH 5.0 (0.1 vol)/absolute ethanol (2.5 vol).

Brain sections from rat were hybridized as previously described (Le Moine et al., 1995). Cryostat sections were post-fixed in 4% paraformaldehyde for 5 min at room temperature, rinsed twice in 4×standard sodium citrate (SSC), and placed into 0.25% acetic anhydride in 0.1 M triethanolamine/4×SSC, pH 8.0 for 10 min at room temperature. After dehydration, the sections were hybridized overnight at 55 C. with 106 cpm of $^{35}$S-labeled cRNA probe in 50 µl of hybridization solution (20 mM Tris-HCl, pH 7.4, 1 mM EDTA, 300 mM NaCl, 50% formamide, 10% dextran sulfate, 1× Denhardt's solution, 250 µg/ml yeast tRNA, 100 µg/ml salmon sperm DNA, 100 mM DTT, 0.1% SDS, 0.1% sodium thiosulfate). After 20 min of RNAse A treatment (20 µg/ml), the sections were subsequently washed at room temperature with 2×SSC twice for 5 min, 1×SSC for 5 min, 0.5×SSC for 5 min, and rinsed in 0.1×SSC at 65 C. twice for 30 min before dehydration (the latter SSC washes contained 1 mM DTT). Sections were exposed on X-ray films (Kodak BIOMAX) for 6 days.

8.1.4. Phosphatase Assays

The activity of PP2C isoforms using pNPP as substrate was assayed as previously described (Brumel et al., 1997). Reaction mixtures (0.1 ml) containing 25 mM HEPES, pH 7.0, 20 mM MnCl$_2$ or 20 mM MgCl$_2$, and 0.125-20 mM substrate, was incubated with the enzyme at 37° C. for 10 min. The reaction was stopped by addition of 1 ml of 0.1 M NaOH, and the initial rate of p-nitrophenol release was determined spectrophotometrically at 405 nm (using a molar extinction coefficient of 18 000 M-1 cm-1).

The activity of PP2C isoforms using $^{32}$P-DARPP (phosphorylated at Ser137) was assayed at 37° C. in a reaction mixture containing 25 mM Tris-HCl, pH 7.5, 10 mM MnCl$_2$, 1% BSA, and 0.5-20 mM substrate, in a total volume of 40 ml. Reactions were stopped by addition of 200 ml of 50% trichloroacetic acid. Samples were then incubated on ice for 30 min and centrifuged at 10,000 g for 10 min at 4° C. Radioactivity recovered in the supernatant was measured by Cerenkov counting in a scintillation counter (Beckman).

Kinetic parameters (Km and Vmax) were determined from Lineweaver-Burk plots.

8.2. Results

Figure 13B:
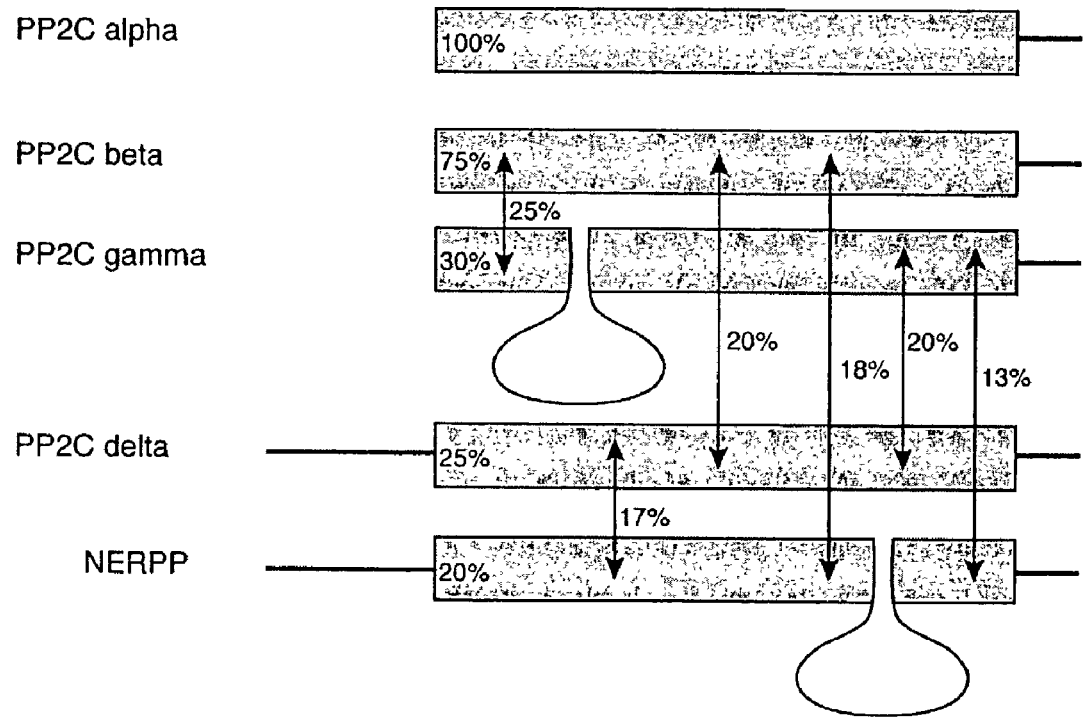

8.2.1. Cloning and Sequence Analysis of PP2C Isoforms Expressed in Rat Striatum PCR fragments, corresponding to the entire open-reading frames of PP2Ca, b, g and d isoforms were amplified from a rat striatal oligo-dT/random primed, reverse transcribed cDNA library (FIG. 12). Full-length calcineurin (PP2B) cDNA was also amplified from the same template as a positive control. As a negative control, we failed to isolate DNA for NERPP, a brain-specific PP2C analog, that is not apparently expressed in striatum (Labes et al., 1998). At least two cDNAs for each PP2C isoform were independently cloned, and sequenced. The deduced amino acid sequences of the clones are presented in FIG. 13A (PP2Cg sequence submitted to GenBank, Accession number AF525687). They are, respectively, at least 99% identical to the previously published cDNA sequence of PP2Ca from kidney (Tamura et al., 1989), b from liver (Marley et al., 1998), g from skeletal muscle (Travis and Welsh, 1997), and d from hypothalamus (Tong et al., 1998). The minor differences in DNA sequences that were obtained in the present study are likely attributable to genomic polymorphism. Comparison of amino acid sequences of striatal PP2C isoforms revealed that the a and b isoforms are most closely related (75% identity), whereas PP2Cg, PP2Cd, and NERPP share relatively low identity with PP2Ca (30, 23, and 20%, respectively) and with each other (FIG. 13B). Despite low identity between the different isoforms, residues involved in metal and phosphate binding (Das et al, 1996) are conserved.

8.2.2. Expression of PP2Ca, b, g, and d mRNA in Rat Brain

There is wide-spread and generally high expression of PP2Ca mRNA throughout the brain (FIG. 14). In particular, very high levels were found in all hippocampal subregions, CA1, CA2, CA3 and dentate gyrus, the granule cell layer of the cerebellum, and in layers 2 and 3 of the cerebral cortex. High levels of PP2Ca mRNA were also found in layers 1, 4 and 6 of the cerebral cortex, in most thalamic and hypothalamic nuclei, the septal nuclei and in striatum (i.e., caudate-putamen and nucleus accumbens).

Moderate levels of PP2Cb mRNA were found in the CA3 and dentate gyrus subregions of hippocampus and in the granule cell layer in the cerebellum. Otherwise, a low but specific level of expression of PP2Cb mRNA was detectable in cerebral cortex, striatum, and thalamus. PP2Cg mRNA was also widely expressed, with the highest levels in frontal cortex. Moderate levels were found in striatum and hippocampus.

The levels of PP2Cd mRNA were found to be low to moderate in most brain regions.

Higher levels of PP2Cd mRNA were found in the periventricular nucleus of thalamus and in the granule cell layer of the cerebellum. Moderate levels were found in all subfields of hippocampus (CA1, CA2, CA3 and dentate gyrus), and in all layers of cerebral cortex. A low, but specific, signal was detected in striatum.

Taken together, the results indicate that PP2Ca and g mRNA are most abundant in brain, while PP2Cb and d mRNA are expressed at moderate to low levels.

8.2.3. Characterization of Recombinant PP2C Isoforms

To further characterize their enzymatic activity, his-tagged PP2Ca, b, g and d isoforms were expressed in *E. coli* and purified on Ni-NTA-agarose, each to greater than approximately 90% homogeneity (FIG. 15). Recombinant PP2Ca, b, and d migrated with apparent molecular masses of approximately 45 kDa on SDS-PAGE, which corresponds to their deduced molecular masses of 42, 43, and 44 kDa, respectively. In contrast, recombinant PP2Cg migrated with a molecular mass of 80 kDa, which is significantly higher than the predicted size of 59 kDa. This is likely caused by the extremely acidic nature of the protein, which will affect SDS binding (aspartic and glutamic acids comprise over 25% of all amino acids in PP2Cg) (FIG. 13A; see also Travis and Welsh, 1997).

Several previous studies have shown that in vitro PP2C activity is dependent on the nature of the divalent metal cation (Pato and Kerc, 1991; Fjeld and Denu, 1999). Both $Mg^{2+}$ and $Mn^{2+}$ have been shown to activate recombinant PP2Ca (Cohen, 1997; Fjeld and Denu, 1999). Other studies have found that recombinant PP2Cd activity is strictly dependent on addition of only $Mn^{2+}$ (Tong et al., 1998). The phosphatase activity of the recombinant PP2C isoforms was initially assayed using pNPP as substrate. A very low level of activity was measured for PP2Ca, b and g in the absence of any divalent cation, and enzyme activity was stimulated by addition of 20 mM $Mg^{2+}$ or $Mn^{2+}$. In contrast, PP2Cd displayed catalytic activity only in the presence of $Mn^{2+}$.

In general, PP2Ca, b and g exhibited similar KM values for pNPP and differed only in their Vmax values for substrate dephosphorylation (Table 7). The Vmax values were 50-100-fold higher in the presence of 20 mM $Mn^{2+}$ compared to 20 mM $Mg^{2+}$. Similarly, their catalytic efficiencies (Kcat/Km) were 2-3 orders of magnitude higher in the presence of $Mn^{2+}$ compared to $Mg^{2+}$. A notable feature of PP2Cg was the high Km observed in the presence of $Mn^{2+}$. PP2Cd was the least efficient enzyme, due largely to the much higher Km for pNPP.

TABLE 7

Kinetic parameters of pNPP hydrolysis by PP2C isoforms

| Enzyme | $K_M$, mM | Vmax, μmol $mg^{-1} min^{-1}$ | kcat, $s^{-1}$ | kcat/$K_M$, $μM^{-1} s^{-1}$ |
|---|---|---|---|---|
| in the presence of 20 mM $Mn^{2+}$ | | | | |
| PP2Ca | 1.53 | 7.49 | 5.83 | $3.8 \times 10^{-3}$ |
| PP2Cb | 2.29 | 10.72 | 8.42 | $3.6 \times 10^{-3}$ |
| PP2Cg | 0.52 | 1.29 | 1.35 | $2.6 \times 10^{-3}$ |
| PP2Cd | 39.95 | 1.21 | $9.4 \times 10^{-1}$ | $2.4 \times 10^{-5}$ |
| in the presence of 20 mM $Mg^{2+}$ | | | | |
| PP2Ca | 3.10 | 0.20 | $1.6 \times 10^{-1}$ | $5.2 \times 10^{-5}$ |
| PP2Cb | 3.20 | 0.20 | $1.6 \times 10^{-1}$ | $5.0 \times 10^{-5}$ |
| PP2Cg | 12.81 | 0.09 | $9.4 \times 10^{-2}$ | $7.3 \times 10^{-6}$ |
| PP2Cd | — | — | — | — |

Legend Table 7. Enzymatic activities of PP2C isoforms assayed using pNPP as substrate. Phosphatase activity was measured using pNPP as substrate by the change in absorbance at 405 nm. Km and Vmax values were calculated from Lineweaver-Burk plots of the data.

8.2.4. Phospho-DARPP-32 Specificity of PP2C Isoforms

Our previous studies have indicated that DARPP-32 phosphorylated at Ser137 by casein kinase 1 CK1) is a physiological substrate for a PP2C-like activity (Desdouits et al., 1998). PP2Ca, b, g and d are expressed in striatum. Therefore, we compared the activities of the PP2C isoforms toward phospho-Ser137-DARPP-32. PP2Cd did not dephosphorylate phospho-Ser137-DARPP-32, whereas the PP2Ca, b and g demonstrated similar initial rates of dephosphorylation (FIG. 16).

We next analyzed the metal-dependence of PP2Ca, b and g using phospho-Ser137-DARPP-32 as a substrate (FIG. 17). Within a concentration range of 0-30 mM, all three isoforms of PP2C dephosphorylated phospho-Ser137-DARPP-32 from 1.2-4-fold more efficiently in the presence of $Mn^{2+}$ compared with in the presence of $Mg^{2+}$. PP2Ca was most sensitive to $Mn^{2+}$ or $Mg^{2+}$, with maximal activities being observed at 4-5 mM divalent cation. PP2Cb and g required higher concentrations (10-20 mM $Mn^{2+}$ or $Mg^{2+}$) for maximal activity. Very high concentrations (up to 50 mM $Mn^{2+}$ or $Mg^{2+}$) resulted in lower phosphatase activities.

Using phospho-Ser 137 DARPP 32 as substrate, we compared the kinetic parameters of PP2Ca, b, and g activity (FIG. 18). All three isoforms exhibited similar Km values of 7-25 mM, and similar Vmax values of 0.3-1.0 mmol/min/mg, with PP2Cg exhibiting the highest catalytic efficiency (Table 8).

TABLE 8

DARPP-S-137-P dephosphorylation by PP2C a, b, and g.
in the presence of 10 mM $Mn^{2+}$

| Enzyme | $K_M$, μM | Vmax, μmol $mg^{-1} min^{-1}$ | kcat, $s^{-1}$ | kcat/$K_M$, $μM^{-1} s^{-1}$ |
|---|---|---|---|---|
| PP2Ca | 13.1 | 0.39 | $3.1 \times 10^{-1}$ | $2.3 \times 10^{-2}$ |
| PP2Cb | 25.3 | 0.99 | $7.8 \times 10^{-1}$ | $3.1 \times 10^{-2}$ |
| PP2Cg | 7.0 | 0.31 | $3.2 \times 10^{-1}$ | $4.5 \times 10^{-2}$ |

Legend Table 8. Enzymatic activities of PP2C isoforms assayed using [$^{32}$P]phospho-Ser137 DARPP-32 as substrate. Phosphatase activity was measured by the release of $^{32}$P, and Km and Vmax values were calculated from Lineweaver-Burk plots of the data.

8.3. Discussion

We have cloned and characterized several of the most diverse neuronal PP2C isoforms that are expressed in striatum, and that are implicated in dephosphorylation of DARPP 32, which is highly enriched in striatum. The state of DARPP 32 phosphorylation, in turn, affects activity of both PP1 and PKA, and plays a key role in dopaminergic and serotonergic neurotransmission (Greengard, 2001). PP2C is also involved in regulation of glutamatergic signaling in brain, since DARPP 32 Ser137 is phosphorylated by CK1, which is activated by metabotropic glutamate receptors (Liu et al., 2001). Thus, it is important to assess role of each individual PP2C isoform in dephosphorylation of the DARPP 32 Ser137 residue.

Prior studies have disclosed that PP2C mRNA is expressed in brain at a relatively low level, with only faint expression in the caudate putamen (Abe et al., 1992). By contrast, our data clearly demonstrate that both PP2C alpha and gamma mRNAs are highly abundant in cortex, cerebellum, and striatum. PP2C beta and delta mRNAs are also expressed throughout the brain, including striatum, at much lower levels.

Lack of specific inhibitors and isoform-specific antibodies explains poor progress in studies of PP2C both in vitro and in vivo. So far PP2C specificity has been identified by a relative resistance to okadaic acid treatment and dependence upon divalent ions, such as $Mg^{2+}$ or $Mn^{2+}$. Since it remains unknown which metal ion(s) catalyzes phosphatase reactions at the PP2C catalytic site in vivo, the metal dependence of PP2C isoforms is of a particular interest.

Our data show that replacement of $Mg^{2+}$ with $Mn^{2+}$ increases Vmax of pNPP hydrolysis in vitro approximately 50 times for both alpha and beta isoforms without a significant effect on the Km of the reaction. PP2Cgamma, in contrast, has 24-fold lower Km and 15-fold higher Vmax when $Mn^{2+}$ substitutes $Mg^{2+}$. These data indicate that the PP2C family may be directly regulated by $Mn^{2+}$.

The similarity of kinetic parameters of DARPP 32 dephosphorylation by PP2C alpha, beta, and, gamma indicates that all three PP2C isoforms are capable of dephosphorylating the Ser137 residue of DARPP 32. Without wishing to be bound by any particular theory, since PP2C alpha is most abundant in the striatum, this isoform may have the largest role of the PPC2C isoforms in dopaminergic and serotonergic intracellular signaling pathways.

8.4. References

Abe H., Tamura S. and Kondo H. (1992) Localization of mRNA for protein phosphatase 2C in the brain of adult rats. Brain Res. Mol. Brain Res. 13, 283-288.

Bialojan C. and Takai A. (1988) Inhibitory effect of a marine-sponge toxin, okadaic acid, on protein phosphatases. Specificity and kinetics. Biochem. J. 256, 283-290.

Bibb J. A., Snyder G. L., Nishi A., Yan Z., Meijer L., Fienberg A. A., Tsai L. H., Kwon Y. T., Girault J. A., Czernik A. J., Huganir R. L., Hemmings H. C., Jr., Nairn A. C. and Greengard P. (1999) Phosphorylation of DARPP-32 by Cdk5 modulates dopamine signaling in neurons. Nature 402, 669-671.

Brumell J. H., Chan C. K., Butler J., Borregaard N., Siminovitch K. A., Grinstein S. and Downey G. P. (1997) Regulation of Src homology 2-containing tyrosine phosphatase 1 during activation of human neutrophils. Role of protein kinase C. J. Biol. Chem. 272, 875-882.

Cheng A., Ross K. E., Kaldis P. and Solomon M. J. (1999) Dephosphorylation of cyclin-dependent kinases by type 2C protein phosphatases. Genes Dev. 13, 2946-2957. Cohen P. T. (1997) Novel protein serine/threonine phosphatases: variety is the spice of life. Trends Biochem. Sci. 22, 245-251.

Das A. K., Helps N. R., Cohen P. T. W. and Barford D. (1996) Crystal structure of the protein serine/threonine phosphatase 2C at 2.0 A resolution. EMBO J. 15, 6798-6809.

Desdouits F., Siciliano J. C., Nairn A. C., Greengard P. and Girault J. A. (1998) Dephosphorylation of Ser-137 in DARPP-32 by protein phosphatases 2A and 2C: different roles in vitro and in striatonigral neurons. Biochem. J. 330, 211-216.

Endo S., Connor J. H., Forney B., Zhang L., Ingebritsen T. S., Lee E. Y. and Shenolikar S. (1997) Conversion of protein phosphatase 1 catalytic subunit to a Mn($^{2+}$)-dependent enzyme impairs its regulation by inhibitor 1. Biochemistry 36, 6986-6992.

Fjeld C. C. and Denu J. M. (1999) Kinetic analysis of human serine/threonine phosphatase 2C. J. Biol. Chem. 274, 20336-20343.

Fukunaga K., Kobayashi T., Tamura S. and Miyamoto E. (1993) Dephosphorylation of autophosphorylated $Ca^{2+}$/calmodulin-dependent protein kinase II by protein phosphatase 2C. J. Biol. Chem. 268, 133-137.

Greengard P. (2001) The neurobiology of slow synaptic transmission. Science 294, 1024-1030.

Hanada M., Ninomiya-Tsuji J., Komaki K., Ohnishi M., Katsura K., Kanamaru R., Matsumoto K. and Tamura S. (2001) Regulation of the TAK1 signaling pathway by protein phosphatase 2C. J. Biol. Chem. 276, 5753-5759.

Hemmings H. C., Jr., Greengard P., Tung H. Y. and Cohen P. (1984) DARPP-32, a dopamine-regulated neuronal phosphoprotein, is a potent inhibitor of protein phosphatase-1. Nature 310, 503-505.

Hishiya A., Ohnishi M., Tamura S. and Nakamura F. (1999) Protein phosphatase 2C inactivates F-actin binding of human platelet moesin. J. Bio.l Chem. 274, 26705-26712.

Labes M., Roder J. and Roach A. (1998) A novel phosphatase regulating neurite extension on CNS inhibitors. Mol. Cell. Neurosci. 12, 29-47.

Le Moine C., Normand E. and Bloch B. (1995) Use of non-radioactive probes for mRNA detection by in situ hybridization: interests and applications in the central nervous system. Cell. Mol. Biol. (Noisy-le-grand) 41, 917-923.

Liu F., Ma X. H., Ule J., Bibb J. A., Nishi A., DeMaggio A. J., Yan Z., Nairn A. C. and Greengard P. (2001) Regulation of cyclin-dependent kinase 5 and casein kinase 1 by metabotropic glutamate receptors. Proc. Natl. Acad. Sci. USA 98, 11062-11068.

Mackintosh C., Beattie K. A., Klumpp S., Cohen P. and Codd G. A. (1990) Cyanobacterial microcystin-LR is a potent and specific inhibitor of protein phosphatases 1 and 2A from both mammals and higher plants. FEBS Lett. 264, 187-192.

Marley A. E., Kline A., Crabtree G., Sullivan J. E. and Beri R. K. (1998) The cloning expression and tissue distribution of human PP2Cbeta. FEBS Lett. 431, 121-124.

Pato M. D. and Kerc E. (1991) Regulation of smooth muscle phosphatase-II by divalent cations. Mol. Cell. Biochem. 101, 31-41.

Price N. E. and Mumby M. C. (1999) Brain protein serine/threonine phosphatases. Curr. Opin. Neurobiol. 9, 336-342.

Seroussi E., Shani N., Ben-Meir D., Chajut A., Divinski I., Faier S., Gery S., Karby S., Kariv-Inbal Z., Sella O., Smorodinsky N. I. and Lavi S. (2001) Uniquely conserved non-translated regions are involved in generation of the two major transcripts of protein phosphatase 2Cbeta. J. Mol. Biol. 312, 439-451.

Strack S., Choi S., Lovinger D. M. and Colbran R. J. (1997) Translocation of autophosphorylated calcium/calmodulin-dependent protein kinase II to the postsynaptic density. J. Biol. Chem. 272, 13467-13470.

Takekawa M., Adachi M., Nakahata A., Nakayama I., Itoh F., Tsukuda H., Taya Y. and Imai K. (2000) p53-inducible wip1 phosphatase mediates a negative feedback regulation of p38 MAPK-p53 signaling in response to UV radiation. EMBO J. 19, 6517-6526.

Takekawa M., MaedaT. and Saito H. (1998) Protein phosphatase 2Calpha inhibits the human stress-responsive p38 and JNK MAPK pathways. EMBO J. 17, 4744-4752.

Tamura S., Lynch K. R., Lamer J., Fox J., Yasui A., Kikuchi K., Suzuki Y. and Tsuiki S. (1989) Molecular cloning of rat type 2C (IA) protein phosphatase mRNA. Proc. Natl. Acad. Sci. USA 86, 1796-1800.

Tong Y., Quirion R. and Shen S. H. (1998) Cloning and characterization of a novel mammalian PP2C isozyme. J. Biol. Chem. 273, 35282-35290.

Travis S. M. and Welsh M. J. (1997) PP2Cgamma: a human protein phosphatase with a unique acidic domain. FEBS Lett. 412, 415-419.

Wenk J., Trompeter H. I., Pettrich K. G., Cohen P. T., Campbell D. G. and Mieskes G. (1992) Molecular cloning and primary structure of a protein phosphatase 2C isoform. FEBS Lett. 297, 135-138.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for identifying an agent for use in treating depression in a patient in need thereof, comprising:
   (a) contacting an agent with phosphatase 2C ("PP2C") and Ser137-phosphorylated Dopamine- and cyclic-AMP-Regulated PhosphoProtein of molecular weight 32,000 Dalton ("DARPP-32");
   (b) detecting the amount of dephosphorylation of Ser137-phosphorylated DARPP-32; and
   (c) testing the agent in an animal model of depression, wherein the agent is identified as an agent for use in treating depression if a decrease in the dephosphorylation of Ser137-phosphorylated DARPP-32 is detected in the presence of the agent in step (b) and if the agent is effective in the animal model tested in step (c).

2. The method of claim 1, wherein the animal model is a rodent learned helplessness model.

3. The method of claim 2, wherein the rodent learned helplessness animal model is a tail suspension test, and wherein a reduction in immobility indicates that the agent is useful for treatment of depression.

4. The method of claim 2, wherein the rodent learned helplessness animal model is a forced swim test, and wherein an increase in swimming indicates that the agent is useful for treatment of depression.

* * * * *

SEQUENCE LISTING

<160> NUMBER OF SEQ ID NOS: 23

<210> SEQ ID NO 1
<211> LENGTH: 204
<212> TYPE: PRT
<213> ORGANISM: Homo sapiens

<400> SEQUENCE: 1

```
Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Asn Glu Asn Gln Ala Ser Glu Glu Asp Glu Leu Gly Glu Leu Arg
            100                 105                 110

Glu Leu Gly Tyr Pro Arg Glu Glu Asp Glu Glu Glu Glu Asp Asp
        115                 120                 125

Glu Glu Glu Glu Glu Glu Asp Ser Gln Ala Glu Val Leu Lys Val
    130                 135                 140
```

```
Ile Arg Gln Ser Ala Gly Gln Lys Thr Thr Arg Gly Leu Gly Leu Glu
145                 150                 155                 160

Gly Pro Trp Glu Arg Pro Pro Leu Asp Glu Ser Glu Arg Asp Gly
                165                 170                 175

Gly Ser Glu Asp Gln Val Glu Asp Pro Ala Leu Ser Glu Pro Gly Glu
                180                 185                 190

Glu Pro Gln Arg Pro Ser Pro Ser Glu Pro Gly Arg
            195                 200

<210> SEQ ID NO 2
<211> LENGTH: 201
<212> TYPE: PRT
<213> ORGANISM: Mus musculus

<400> SEQUENCE: 2

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
                20                  25                  30

Pro Thr Pro Ala Leu Leu Phe Arg Val Ser Glu His Ser Ser Pro Glu
            35                  40                  45

Glu Glu Glu Glu Glu Ala Ser Pro His Gln Arg Thr Ser Gly Glu Gly
        50                  55                  60

His His Pro Lys Ser Lys Arg Pro Asn Pro Cys Ala Tyr Thr Pro Pro
65                  70                  75                  80

Ser Leu Lys Ala Val Arg Arg Leu Gln Thr Ile Ser Asn Leu Ser Glu
                85                  90                  95

Asn Gln Ala Ser Glu Glu Glu Asp Glu Leu Gly Glu Leu Arg Glu Leu
            100                 105                 110

Gly Tyr Pro Gln Glu Asp Asp Glu Asp Glu Asp Glu Glu Glu Asp
        115                 120                 125

Glu Glu Glu Asp Ser Gln Ala Glu Val Leu Lys Gly Ser Arg Gly Thr
130                 135                 140

Val Gly Gln Lys Leu Leu Val Ala Gly Val Trp Arg Gly Pro Gly Ser
145                 150                 155                 160

Ala His Leu Leu Trp Met Ser Pro Arg Glu Met Glu Thr Leu Arg Thr
                165                 170                 175

Lys Trp Lys Ala Glu Gln His Glx Val Ser Leu Glu Arg Asn Leu Ser
                180                 185                 190

Ile Pro Ala Pro Pro Glu Pro Gly Thr
            195                 200

<210> SEQ ID NO 3
<211> LENGTH: 205
<212> TYPE: PRT
<213> ORGANISM: Rattus sp.

<400> SEQUENCE: 3

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
                20                  25                  30

Pro Thr Pro Ala Leu Leu Phe Arg Val Ser Glu His Ser Ser Pro Glu
            35                  40                  45

Glu Glu Ser Ser Pro His Gln Arg Thr Ser Gly Glu Gly His His Pro
        50                  55                  60
```

```
Lys Ser Lys Arg Pro Asn Pro Cys Ala Tyr Thr Pro Pro Ser Leu Lys
 65                  70                  75                  80

Ala Val Gln Arg Ile Ala Glu Ser His Leu Gln Thr Ile Ser Asn Leu
                 85                  90                  95

Ser Glu Asn Gln Ala Ser Glu Glu Asp Glu Leu Gly Glu Leu Arg
                100                 105                 110

Glu Leu Gly Tyr Pro Asn Glu Asp Glu Glu Asp Glu Asp Glu Asp
            115                 120                 125

Glu Glu Glu Asp Glu Glu Asp Ser Gln Ala Glu Val Leu Lys Gly
        130                 135                 140

Ser Arg Gly Thr Ala Gly Asn Lys Leu Thr Ser Gly Gln Gly Leu Glu
145                 150                 155                 160

Gly Pro Trp Glu Arg Pro Pro Leu Asp Glu Pro Gln Arg Asp Gly
                165                 170                 175

Asn Ser Glu Asp Gln Gly Glu Gly Arg Ala Thr Gln Ser Glu Pro Gly
                180                 185                 190

Glu Glu Pro Arg His Pro Thr Pro Pro Glu Ser Gly Thr
            195                 200                 205

<210> SEQ ID NO 4
<211> LENGTH: 203
<212> TYPE: PRT
<213> ORGANISM: bovine

<400> SEQUENCE: 4

Met Asp Pro Lys Asp Arg Lys Lys Ile Gln Phe Ser Val Pro Ala Pro
 1               5                  10                  15

Pro Ser Gln Leu Asp Pro Arg Gln Val Glu Met Ile Arg Arg Arg Arg
                 20                  25                  30

Pro Thr Pro Ala Met Leu Phe Arg Leu Ser Glu His Ser Ser Pro Glu
             35                  40                  45

Glu Glu Ala Ser Pro His Gln Arg Ala Ser Gly Glu Gly His His Leu
 50                  55                  60

Lys Ser Lys Arg Pro Asn Pro Cys Ala Tyr Thr Pro Pro Ser Leu Lys
 65                  70                  75                  80

Ala Val Gln Arg Ile Ala Glu Ser His Leu Gln Ser Ile Ser Asn Leu
                 85                  90                  95

Gly Glu Asn Gln Ala Ser Glu Glu Asp Glu Leu Gly Glu Leu Arg
                100                 105                 110

Glu Leu Gly Tyr Pro Arg Glu Glu Glu Glu Glu Glu Glu Glu Asp
            115                 120                 125

Glu Glu Glu Glu Glu Asp Ser Gln Ala Glu Val Leu Lys Gly Ser Arg
        130                 135                 140

Gly Ser Ala Gly Gln Lys Thr Thr Tyr Gly Gln Gly Leu Glu Gly Pro
145                 150                 155                 160

Trp Glu Arg Pro Pro Leu Asp Gly Pro Gln Arg Asp Gly Ser Ser
                165                 170                 175

Glu Asp Gln Val Glu Asp Pro Ala Leu Asn Glu Pro Gly Glu Glu Pro
            180                 185                 190

Gln Arg Met Pro Ala His Pro Glu Pro Gly Thr
            195                 200

<210> SEQ ID NO 5
<211> LENGTH: 16
<212> TYPE: PRT
```

```
<213> ORGANISM: Homo sapiens

<400> SEQUENCE: 5

Lys Arg Pro Asn Pro Cys Ala Tyr Thr Pro Pro Ser Leu Lys Ala Val
1               5                   10                  15

<210> SEQ ID NO 6
<211> LENGTH: 11
<212> TYPE: PRT
<213> ORGANISM: Homo sapiens

<400> SEQUENCE: 6

Glu Glu Glu Asp Ser Gln Ala Glu Val Leu Lys
1               5                   10

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gcgtcgacga tgggagcatt tttagacaag                                    30

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
tattcatgcg gccgcttacc acatatcatc agttg                              35

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
gcgtcgtcga cgatgggtgc atttttggat aa                                 32

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
tattcatgcg gccgcttata aggctaccaa tgagtc                             36

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
acgcgtcgac aaatgggtgc ctacctctct cagcc                              35
```

```
<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
ataagaatgc ggccgcctgc tagtcccgct tggccttctt                     40

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
gcgtcgacga tggacctatt cggggacttg                                30

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
tattcatgcg gccgcgtgtc ctatcctcac cacc                           34

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
gcgtcgacga tggccgcccc ggagccggc                                 29

<210> SEQ ID NO 16
<211> LENGTH: 36
<212> TYPE: DNA
<213> ORGANISM: Artificial Sequence
<220> FEATURE:
<223> OTHER INFORMATION: primer

<400> SEQUENCE: 16
tattcatgcg gccgctcact tgttcctgat gacctc                         36

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
gcgtcgacga tggggaagag cacacacaat gaag                           34

<210> SEQ ID NO 18
<211> LENGTH: 39
<212> TYPE: DNA
<213> ORGANISM: Artificial Sequence
<220> FEATURE:
<223> OTHER INFORMATION: primer
```

-continued

<400> SEQUENCE: 18
tattcatgcg gccgctcatg acagcttgtt tccatgtat         39

<210> SEQ ID NO 19
<211> LENGTH: 382
<212> TYPE: PRT
<213> ORGANISM: Rattus sp.

<400> SEQUENCE: 19

```
Met Gly Ala Phe Leu Asp Lys Pro Lys Met Glu Lys His Asn Ala Gln
1               5                   10                  15

Gly Gln Gly Asn Gly Leu Arg Tyr Gly Leu Ser Ser Met Gln Gly Trp
                20                  25                  30

Arg Val Glu Met Glu Asp Ala His Thr Ala Val Ile Gly Leu Pro Asn
            35                  40                  45

Gly Leu Glu Thr Trp Ser Phe Phe Ala Val Tyr Asp Gly His Ala Gly
        50                  55                  60

Ser Gln Val Ala Lys Tyr Cys Cys Glu His Leu Leu Asp His Ile Thr
65                  70                  75                  80

Asn Asn Gln Asp Phe Lys Gly Ser Ala Gly Ala Pro Ser Val Glu Asn
                85                  90                  95

Val Lys Asn Gly Ile Arg Thr Gly Phe Leu Glu Ile Asp Glu His Met
            100                 105                 110

Arg Val Met Ser Glu Lys Lys His Gly Ala Asp Arg Ser Gly Ser Thr
        115                 120                 125

Ala Val Gly Val Leu Ile Ser Pro Gln His Thr Tyr Phe Ile Asn Cys
    130                 135                 140

Gly Asp Ser Arg Gly Leu Leu Cys Arg Asn Arg Lys Val His Phe Phe
145                 150                 155                 160

Thr Gln Asp His Lys Pro Ser Asn Pro Leu Glu Lys Glu Arg Ile Gln
                165                 170                 175

Asn Ala Gly Gly Ser Val Met Ile Gln Arg Val Asn Gly Ser Leu Ala
            180                 185                 190

Val Ser Arg Ala Leu Gly Asp Phe Asp Tyr Lys Cys Val His Gly Lys
        195                 200                 205

Gly Pro Thr Glu Gln Leu Val Ser Pro Glu Pro Glu Val His Asp Ile
    210                 215                 220

Glu Arg Ser Glu Glu Asp Asp Gln Phe Ile Ile Leu Ala Cys Asp Gly
225                 230                 235                 240

Ile Trp Asp Val Met Gly Asn Glu Glu Leu Cys Asp Phe Val Arg Ser
                245                 250                 255

Arg Leu Glu Val Thr Asp Asp Leu Glu Lys Val Cys Asn Glu Val Val
            260                 265                 270

Asp Thr Cys Leu Tyr Lys Gly Ser Arg Asp Asn Met Ser Val Ile Leu
        275                 280                 285

Ile Cys Phe Pro Asn Ala Pro Lys Val Ser Ala Glu Ala Val Lys Lys
    290                 295                 300

Glu Ala Glu Leu Asp Lys Tyr Leu Glu Asn Arg Val Glu Glu Ile Ile
305                 310                 315                 320

Lys Lys Gln Gly Glu Gly Val Pro Asp Leu Val His Val Met Arg Thr
                325                 330                 335

Leu Ala Ser Glu Asn Ile Pro Ser Leu Pro Pro Gly Gly Glu Leu Ala
            340                 345                 350

Ser Lys Arg Asn Val Ile Glu Ala Val Tyr Asn Arg Leu Asn Pro Tyr
```

```
                355                 360                 365
Lys Asn Asp Asp Thr Asp Ser Ala Ser Thr Asp Met Trp
        370                 375                 380

<210> SEQ ID NO 20
<211> LENGTH: 390
<212> TYPE: PRT
<213> ORGANISM: Rattus sp.

<400> SEQUENCE: 20

Met Gly Ala Phe Leu Asp Glu Pro Lys Thr Glu Lys His Asn Ala His
1               5                   10                  15

Gly Ala Gly Asn Gly Leu Arg Tyr Gly Leu Ser Ser Met Gln Gly Trp
            20                  25                  30

Arg Val Glu Met Glu Asp Ala His Thr Ala Val Val Gly Ile Pro His
        35                  40                  45

Gly Leu Glu Asp Trp Ser Phe Phe Ala Val Tyr Asp Gly His Ala Gly
    50                  55                  60

Ser Arg Val Ala Asn Tyr Cys Ser Thr His Leu Leu Glu His Ile Thr
65                  70                  75                  80

Thr Asn Glu Asp Phe Arg Ala Ala Asp Lys Ser Gly Phe Ala Leu Glu
                85                  90                  95

Pro Ser Val Glu Asn Val Lys Thr Gly Ile Arg Thr Gly Phe Leu Lys
            100                 105                 110

Ile Asp Glu Tyr Met Arg Asn Phe Ser Asp Leu Arg Asn Gly Met Asp
        115                 120                 125

Arg Ser Gly Ser Thr Ala Val Gly Val Met Ile Ser Pro Thr His Ile
    130                 135                 140

Tyr Phe Ile Asn Cys Gly Asp Ser Arg Ala Val Leu Cys Arg Asn Gly
145                 150                 155                 160

Gln Val Cys Phe Ser Thr Gln Asp His Lys Pro Cys Asn Pro Met Glu
                165                 170                 175

Lys Glu Arg Ile Gln Asn Ala Gly Gly Ser Val Met Ile Gln Arg Val
            180                 185                 190

Asn Gly Ser Leu Ala Val Ser Arg Ala Leu Gly Asp Tyr Asp Tyr Lys
        195                 200                 205

Cys Val Asp Gly Lys Gly Pro Thr Glu Gln Leu Val Ser Pro Glu Pro
    210                 215                 220

Glu Val Tyr Glu Ile Leu Arg Ala Glu Glu Asp Glu Phe Val Val Leu
225                 230                 235                 240

Ala Cys Asp Gly Ile Trp Asp Val Met Ser Asn Glu Glu Leu Cys Glu
                245                 250                 255

Phe Val Asn Ser Arg Leu Glu Val Ser Asp Asp Leu Glu Asn Val Cys
            260                 265                 270

Asn Trp Val Val Asp Thr Cys Leu His Lys Gly Ser Arg Asp Asn Met
        275                 280                 285

Ser Ile Val Leu Val Cys Phe Ala Asn Ala Pro Lys Val Ser Asp Glu
    290                 295                 300

Ala Val Lys Arg Asp Leu Glu Leu Asp Lys His Leu Glu Ser Arg Val
305                 310                 315                 320

Glu Glu Ile Met Gln Lys Ser Gly Glu Glu Gly Met Pro Asp Leu Ala
                325                 330                 335

His Val Met Arg Ile Leu Ser Ala Glu Asn Ile Pro Asn Leu Pro Pro
            340                 345                 350
```

```
Gly Gly Gly Leu Ala Gly Lys Ser Asn Val Ile Glu Ala Val Tyr Ser
            355                 360                 365

Arg Leu Asn Pro Asn Lys Asp Asn Gly Gly Ala Gly Asp Leu Glu
        370                 375                 380

Asp Ser Leu Val Ala Leu
385                 390

<210> SEQ ID NO 21
<211> LENGTH: 542
<212> TYPE: PRT
<213> ORGANISM: Rattus sp.

<400> SEQUENCE: 21

Met Gly Ala Tyr Leu Ser Gln Pro Asn Thr Val Lys Cys Ser Gly Asp
1               5                   10                  15

Gly Val Gly Ala Pro Arg Leu Pro Leu Pro Tyr Gly Phe Ser Ala Met
            20                  25                  30

Gln Gly Trp Arg Val Ser Met Glu Asp Ala His Asn Cys Ile Pro Glu
        35                  40                  45

Leu Asp Asn Glu Thr Ala Met Phe Ser Val Tyr Asp Gly His Gly Gly
    50                  55                  60

Glu Glu Val Ala Leu Tyr Cys Ala Lys Tyr Leu Pro Asp Ile Ile Lys
65                  70                  75                  80

Asp Gln Lys Ala Tyr Lys Glu Gly Lys Leu Gln Lys Ala Leu Gly Asp
                85                  90                  95

Ala Phe Leu Ala Ile Asp Ala Lys Leu Thr Thr Glu Val Ile Lys
            100                 105                 110

Glu Leu Ala Gln Ile Ala Gly Arg Pro Thr Glu Asp Glu Asp Asp Lys
        115                 120                 125

Glu Lys Val Ala Asp Glu Asp Val Asp Asn Glu Glu Ala Ala Leu
    130                 135                 140

Leu His Glu Glu Ala Thr Met Thr Ile Glu Glu Leu Leu Thr Arg Tyr
145                 150                 155                 160

Gly Gln Asn Cys Gln Lys Gly Pro Pro His Thr Lys Ser Gly Thr Gly
                165                 170                 175

Ile Gly Glu Asp Pro Glu Pro Gln Gly Leu Asn Gly Glu Ala Gly Pro
            180                 185                 190

Glu Asp Pro Ser Arg Glu Thr Pro Ser Gln Glu Asn Gly Pro Thr Ala
        195                 200                 205

Lys Gly Tyr Thr Gly Pro Ser Ser Asn Ser Asp His Gly Thr Glu Ala
    210                 215                 220

Gly Gln Ile Gly Glu Pro Gly Thr Ala Thr Gly Glu Ala Gly Pro Ser
225                 230                 235                 240

Cys Ser Ser Ala Ser Asp Lys Leu Pro Arg Val Ala Lys Ser Lys Phe
                245                 250                 255

Phe Glu Asp Ser Glu Asp Glu Ser Asp Glu Val Glu Glu Glu Asp
            260                 265                 270

Asp Ser Glu Glu Cys Ser Glu Asp Glu Asp Gly Tyr Ser Ser Glu Glu
        275                 280                 285

Ala Glu Asn Glu Glu Asp Glu Asp Thr Glu Glu Ala Glu Glu Asp
    290                 295                 300

Asp Asp Glu Glu Met Met Val Pro Gly Met Glu Gly Lys Glu Glu Pro
305                 310                 315                 320

Gly Ser Asp Ser Gly Thr Thr Ala Val Val Ala Leu Ile Arg Gly Lys
                325                 330                 335
```

-continued

```
Gln Leu Ile Val Ala Asn Ala Gly Asp Ser Arg Cys Val Val Ser Glu
            340                 345                 350

Ala Gly Lys Ala Leu Asp Met Ser Tyr Asp His Lys Pro Glu Asp Glu
        355                 360                 365

Val Glu Leu Ala Arg Ile Lys Asn Ala Gly Lys Val Thr Met Asp
    370                 375                 380

Gly Arg Val Asn Gly Leu Asn Leu Ser Arg Ala Ile Gly Asp His
385                 390                 395                 400

Phe Tyr Lys Arg Asn Lys Asn Leu Pro Pro Gln Glu Gln Met Ile Ser
                405                 410                 415

Ala Leu Pro Asp Ile Lys Val Leu Thr Leu Thr Asp Asp His Glu Phe
            420                 425                 430

Met Val Ile Ala Cys Asp Gly Ile Trp Asn Val Met Ser Ser Gln Glu
        435                 440                 445

Val Val Asp Phe Ile Gln Ser Lys Ile Ser Gln Arg Asp Glu Asn Gly
    450                 455                 460

Glu Leu Arg Leu Leu Ser Ser Ile Val Glu Glu Leu Leu Asp Gln Cys
465                 470                 475                 480

Leu Ala Pro Asp Thr Ser Gly Asp Gly Thr Gly Cys Asp Asn Met Thr
                485                 490                 495

Cys Ile Ile Ile Cys Phe Lys Pro Arg Asn Thr Val Glu Leu Gln Pro
            500                 505                 510

Glu Ser Gly Lys Arg Lys Leu Glu Glu Val Leu Ser Thr Glu Gly Ala
        515                 520                 525

Glu Glu Asn Gly Asn Ser Asp Lys Lys Lys Ala Lys Arg Asp
    530                 535                 540

<210> SEQ ID NO 22
<211> LENGTH: 392
<212> TYPE: PRT
<213> ORGANISM: Rattus sp.

<400> SEQUENCE: 22

Met Asp Leu Phe Gly Asp Leu Pro Glu Pro Glu Arg Ala Pro Arg Pro
1               5                   10                  15

Ser Ala Gly Lys Glu Ala Gln Glu Gly Pro Val Leu Phe Glu Asp Leu
            20                  25                  30

Pro Pro Thr Ser Ser Thr Asp Ser Gly Ser Gly Gly Pro Leu Leu Phe
        35                  40                  45

Asp Gly Leu Pro Pro Ala Gly Ser Gly Asn Ser Gly Ser Leu Ala Thr
    50                  55                  60

Ser Gly Ser Gln Val Val Lys Asn Glu Gly Lys Gly Ala Lys Arg Lys
65                  70                  75                  80

Ala Pro Glu Glu Glu Asp Asn Gly Gly Glu Glu Leu Val Glu Lys Lys
                85                  90                  95

Val Cys Lys Ala Ser Ser Val Ile Phe Gly Leu Lys Gly Tyr Val Ala
            100                 105                 110

Glu Arg Lys Gly Glu Arg Glu Met Gln Asp Ala His Val Ile Leu
        115                 120                 125

Asn Asp Ile Thr Gln Glu Cys Asn Pro Pro Ser Ser Leu Ile Thr Arg
    130                 135                 140

Val Ser Tyr Phe Ala Val Phe Asp Gly His Gly Gly Ile Arg Ala Ser
145                 150                 155                 160

Lys Phe Ala Ala Gln Asn Leu His Gln Asn Leu Ile Arg Lys Phe Pro
```

-continued

```
                165                 170                 175
Lys Gly Asp Val Ile Ser Val Glu Lys Thr Val Lys Arg Cys Leu Leu
                180                 185                 190

Asp Thr Phe Lys His Thr Asp Glu Glu Phe Leu Lys Gln Ala Ser Ser
            195                 200                 205

Gln Lys Pro Ala Trp Lys Asp Gly Ser Thr Ala Thr Cys Val Leu Ala
        210                 215                 220

Val Asp Asn Ile Leu Tyr Ile Ala Asn Leu Gly Asp Ser Arg Ala Ile
225                 230                 235                 240

Leu Cys Arg Tyr Asn Glu Glu Ser Gln Lys His Ala Ala Leu Ser Leu
                245                 250                 255

Ser Lys Glu His Asn Pro Thr Gln Tyr Glu Glu Arg Met Arg Ile Gln
            260                 265                 270

Lys Ala Gly Gly Asn Val Arg Asp Gly Arg Val Leu Gly Val Leu Glu
        275                 280                 285

Val Ser Arg Ser Ile Gly Asp Gly Gln Tyr Lys Arg Cys Gly Val Thr
    290                 295                 300

Ser Val Pro Asp Ile Arg Arg Cys Gln Leu Thr Pro Asn Asp Arg Phe
305                 310                 315                 320

Ile Leu Leu Ala Cys Asp Gly Leu Phe Lys Val Phe Thr Pro Glu Glu
                325                 330                 335

Ala Val Asn Phe Ile Leu Ser Cys Leu Glu Asp Glu Lys Ile Gln Thr
            340                 345                 350

Arg Glu Gly Lys Pro Ala Val Asp Ala Arg Tyr Glu Ala Ala Cys Asn
        355                 360                 365

Arg Leu Ala Asn Lys Ala Val Gln Arg Gly Ser Ala Asp Asn Val Thr
    370                 375                 380

Val Met Val Val Arg Ile Gly His
385                 390

<210> SEQ ID NO 23
<211> LENGTH: 513
<212> TYPE: PRT
<213> ORGANISM: Rattus sp.

<400> SEQUENCE: 23

Met Leu Thr Arg Val Lys Ser Ala Val Ala Asn Phe Met Gly Gly Ile
1               5                   10                  15

Met Ala Gly Ser Ser Gly Ser Glu His Gly Gly Ser Gly Cys Gly Gly
            20                  25                  30

Ser Asp Leu Pro Leu Arg Phe Pro Tyr Gly Arg Pro Glu Phe Leu Gly
        35                  40                  45

Leu Ser Gln Asp Glu Val Glu Cys Ser Ala Asp His Ile Ala Arg Pro
    50                  55                  60

Ile Leu Ile Leu Lys Glu Thr Arg Arg Leu Pro Trp Ala Thr Gly Tyr
65                  70                  75                  80

Ala Glu Val Ile Asn Ala Gly Lys Ser Thr His Asn Glu Asp Gln Ala
                85                  90                  95

Ser Cys Glu Val Leu Thr Val Lys Lys Val Gly Thr Ile Thr Ser
            100                 105                 110

Thr Pro Asn Arg Asn Ser Lys Arg Ser Ser Leu Pro Asn Gly Glu
        115                 120                 125

Gly Leu Gln Leu Lys Glu Asn Ser Glu Ser Glu Gly Ile Ser Cys His
    130                 135                 140
```

-continued

```
Tyr Trp Ser Leu Phe Asp Gly His Ala Gly Ser Gly Ala Ala Val Val
145                 150                 155                 160

Arg Ser Arg Leu Leu Gln His His Ile Thr Gln Gln Leu Gln Asp Ile
                165                 170                 175

Val Glu Ile Leu Lys Asn Ser Ala Ile Leu Pro Pro Thr Cys Leu Gly
            180                 185                 190

Glu Glu Pro Glu Ser Thr Pro Ala His Gly Arg Thr Leu Thr Arg Ala
        195                 200                 205

Ala Ser Leu Arg Gly Gly Val Gly Ala Pro Gly Ser Pro Ser Thr Pro
    210                 215                 220

Pro Thr Arg Phe Phe Thr Glu Lys Lys Ile Pro His Glu Cys Leu Val
225                 230                 235                 240

Ile Gly Ala Leu Glu Ser Ala Phe Lys Glu Met Asp Leu Gln Ile Glu
                245                 250                 255

Arg Glu Arg Ser Arg Tyr Asn Ile Ser Gly Gly Cys Thr Ala Leu Ile
                260                 265                 270

Val Val Cys Leu Leu Gly Lys Leu Tyr Val Ala Asn Ala Gly Asp Ser
            275                 280                 285

Arg Ala Ile Ile Ile Arg Asn Gly Glu Ile Ile Pro Met Ser Ser Glu
    290                 295                 300

Phe Thr Pro Glu Thr Glu Arg Gln Arg Leu Gln Tyr Leu Ala Phe Met
305                 310                 315                 320

Gln Pro His Leu Leu Gly Asn Glu Phe Thr His Leu Glu Phe Pro Arg
                325                 330                 335

Arg Val Gln Arg Lys Glu Leu Gly Lys Lys Met Leu Tyr Arg Asp Phe
                340                 345                 350

Asn Met Thr Gly Trp Ala Tyr Lys Thr Ile Glu Asp Asp Asp Leu Lys
            355                 360                 365

Phe Pro Leu Ile Tyr Gly Glu Gly Lys Lys Ala Arg Val Met Ala Thr
370                 375                 380

Ile Gly Val Thr Arg Gly Leu Gly Asp His Asp Leu Lys Val His Asp
385                 390                 395                 400

Ser Asn Ile Tyr Ile Lys Pro Phe Leu Ser Ser Ala Pro Glu Val Arg
                405                 410                 415

Val Tyr Asp Leu Ser Lys Tyr Glu His Gly Ala Asp Val Leu Ile
            420                 425                 430

Leu Ala Thr Asp Gly Leu Trp Asp Val Leu Ser Asn Glu Glu Val Ala
        435                 440                 445

Glu Ala Ile Thr Gln Phe Leu Pro Asn Cys Asp Pro Asp Asp Pro His
    450                 455                 460

Arg Tyr Thr Leu Ala Ala Gln Asp Leu Val Met Arg Ala Arg Gly Val
465                 470                 475                 480

Leu Lys Asp Arg Gly Trp Arg Ile Ser Asn Asp Arg Leu Asp Ser Gly
                485                 490                 495

Asp Asp Ile Ser Val Tyr Val Ile Pro Leu Ile His Gly Asn Lys Leu
            500                 505                 510

Ser
```